(12) United States Patent
Stroup et al.

(10) Patent No.: US 7,512,541 B2
(45) Date of Patent: Mar. 31, 2009

(54) SYSTEM AND METHOD FOR COLLECTING, ORGANIZING AND PRESENTING RESEARCH-ORIENTED MEDICAL INFORMATION

(75) Inventors: Richard Stroup, Overland Park, KS (US); Marcy L. Tarrants, Oak Grove, MO (US); Gary K. Lofland, Kansas City, MO (US); James E. O'Brien, Jr., Leawood, KS (US); Gary E. Grist, Blue Springs, MO (US); Pamela A. Dennis, Olathe, KS (US)

(73) Assignee: Children's Mercy Hospital, Kansas City, MO (US)

( * ) Notice: Subject to any disclaimer, the term of this patent is extended or adjusted under 35 U.S.C. 154(b) by 529 days.

(21) Appl. No.: 11/340,351

(22) Filed: Jan. 26, 2006

(65) Prior Publication Data

US 2007/0016440 A1    Jan. 18, 2007

Related U.S. Application Data

(60) Provisional application No. 60/694,160, filed on Jun. 27, 2005.

(51) Int. Cl.
*G06F 17/30* (2006.01)
*G06F 7/00* (2006.01)
*G06F 17/00* (2006.01)
*G06Q 10/00* (2006.01)
*G06Q 50/00* (2006.01)
*G06F 19/00* (2006.01)
*A61B 5/00* (2006.01)

(52) U.S. Cl. .................... 705/2; 705/3; 707/104.1; 707/3

(58) Field of Classification Search .............. None
See application file for complete search history.

(56) References Cited

U.S. PATENT DOCUMENTS

| | | | |
|---|---|---|---|
| 6,611,846 B1 * | 8/2003 | Stoodley | 707/104.1 |
| 6,820,235 B1 * | 11/2004 | Bleicher et al. | 715/236 |
| 6,839,678 B1 * | 1/2005 | Schmidt et al. | 705/3 |
| 7,353,238 B1 * | 4/2008 | Gliklich | 707/104.1 |
| 2003/0140043 A1 * | 7/2003 | Hotchkiss et al. | 707/10 |
| 2003/0208378 A1 * | 11/2003 | Thangaraj et al. | 705/2 |
| 2004/0078216 A1 * | 4/2004 | Toto | 705/2 |
| 2004/0093240 A1 * | 5/2004 | Shah | 705/2 |
| 2004/0210457 A1 * | 10/2004 | Sameh | 705/2 |
| 2005/0021361 A1 * | 1/2005 | Huang et al. | 705/1 |
| 2005/0096540 A1 * | 5/2005 | Ooshima | 600/437 |

* cited by examiner

*Primary Examiner*—Charles Rones
*Assistant Examiner*—Alicia M Lewis
(74) *Attorney, Agent, or Firm*—Hovey Williams LLP

(57) ABSTRACT

A method and computer program manages medical research study information and laboratory test result information. The program generates an interactive user interface with elements for setting up a study (702), managing study member information (704), managing patient information (706), receiving and displaying comments (708), and configuring data to be stored in a database associated with the research study (710). The program also receives medical event information from a user and laboratory test result information from a laboratory information system (20*d*), and generates a chart (934) that correlates the test results and the medical events. The program also receives a normal range pertaining to a test result from the laboratory information system (20*d*) and provides a normal range indicator (952) for the test result.

4 Claims, 57 Drawing Sheets

| | Snyapse/Synapse/All Patients/Unruh, Tatro Jay 0987883 M | | | | | | | | |
|---|---|---|---|---|---|---|---|---|---|
| | Patient Name | Accession No | Patient ID | Proc Description | Study Date Time | Mod... | Status | Ima... | Proc C... | Last Modified Time... |
| | Doe, Baby | 495481.001 | | OUTSIDE COPI... | 4/4/2005 10:59... | OT | Final... | 3 | RAD_C... | 4/4/2005 10:59:5... |
| | Doe, Baby | 484219.001 | | Chest AP & Lat... | 3/8/2005 5:38... | CR | Final... | 2 | RAD_CH2 | 3/8/2005 6:10:23... |
| | Doe, Baby | 484217.00 | | Chest AP & Lat... | 3/7/2005 12:0... | CR | Final... | 2 | RAD_CH2 | 3/7/2005 12:0... |
| | Doe, Baby | 484076.001 | | Chest AP & Lat... | 3/7/2005 5:37... | CR | Final... | 2 | RAD_CH2 | 3/7/2005 5:37... |
| | Doe, Baby | 483696.001 | | Chest AP & Lat... | 3/6/2005 6:14... | CR | Final... | 2 | RAD_CH2 | 3/6/2005 6:14... |
| | Doe, Baby | 483550.001 | | Chest AP & Lat... | 3/5/2005 6:05... | CR | Final... | 2 | RAD_CH2 | 3/5/2005 6:05... |
| | Doe, Baby | 483435.001 | | Chest AP- 1 Vi... | 3/4/2005 2:44... | CR | Final... | 1 | RAD_C... | 3/4/2005 2:44... |
| | Doe, Baby | 483150.001 | | Chest AP- 1 Vi... | 3/4/2005 6:19... | CR | Final... | 1 | RAD_C... | 3/4/2005 6:19... |
| | Doe, Baby | 482677.001 | | Chest AP- 1 Vi... | 3/3/2005 9:16... | CR | Final... | 1 | RAD_C... | 3/3/2005 9:16... |
| | Doe, Baby | 482620.001 | | Chest AP- 1 Vi... | 3/3/2005 5:43... | CR | Final... | 1 | RAD_C... | 3/3/2005 5:43... |
| | Doe, Baby | 482435.001 | | Chest AP- 1 Vi... | 3/2/2005 1:51... | CR | Final... | 1 | RAD_CH2 | 3/2/2005 1:51... |
| | Doe, Baby | 481912.001 | | Chest AP & Lat... | 3/1/2005 1:53... | CR | Final... | 2 | RAD_C... | 3/1/2005 1:53... |
| | Doe, Baby | 481067.001 | | Chest AP- 1 Vi... | 2/28/2005 4:27.. | CR | Final... | 1 | RAD_C... | 2/28/2005 4:27... |
| | Doe, Baby | 480898.001 | | Chest AP- 1 Vi... | 2/27/2005 12:5... | CR | Final... | 1 | RAD_C... | 2/27/2005 12:5... |
| | Doe, Baby | 480286.001 | | Chest AP- 1 Vi... | 2/25/2005 9:57... | CR | Final... | 1 | RAD_C... | 2/25/2005 9:57... |
| | Doe, Baby | 479653.001 | | Chest AP- 1 Vi... | 2/24/2005 5:49... | CR | Final... | 1 | RAD_A... | 2/24/2005 5:49... |
| | Doe, Baby | 479333.001 | | Abdomen Supin... | 2/23/2005 10:2... | CR | Final... | 1 | RAD_C... | 2/23/2005 10:2... |
| | Doe, Baby | 479236.001 | | Chest AP- 1 Vi... | 2/23/2005 5:55.. | CR | Final... | 1 | RAD_U... | 2/23/2005 5:55... |
| | Doe, Baby | 479016.001 | | US Abdomen-C... | 2/22/2005 3:22.. | US | Final... | 54 | RAD_U... | 2/22/2005 3:22... |
| | Doe, Baby | 479014.001 | | US Head | 2/22/2005 3:09... | US | Final... | 45 | RAD_U... | 2/22/2005 3:09... |
| | Doe, Baby | 479015.001 | | US Abdomen-D... | 2/22/2005 2:02... | US | Final... | 0 | RAD_C... | 2/22/2005 2:02... |
| | Doe, Baby | 478769.001 | | Chest Abdomen... | 2/22/2005 6:36... | CR | Final... | 1 | RAD_C... | 2/22/2005 6:36... |
| | Doe, Baby | 478768.001 | | Chest AP- 1 Vi... | 2/22/2005 6:06... | CR | Cancel | 0 | RAD_C... | 2/22/2005 6:06... |
| | Doe, Baby | 478756.001 | | Chest AP- 1 Vi... | 2/22/2005 4:15... | CR | Final... | 1 | RAD_C... | 2/22/2005 4:15... |

MRN: 0000000
Last: Doe
First: Baby
DOB: 9/15/2002
Sex: M
Race: CAUCAISIAN/WHI
Age: 2y 3m 3d

| Column | Description | Indicator |
|---|---|---|
| Collected | Date and time sample was collected | N |
| BGS | | N |
| PH | | Y |
| PCO2 | Partial $CO_2$ | Y |
| HCO3 | Bicarbonate | Y |
| TCO2 | Total $CO_2$ | Y |
| Base Excess | | Y |
| FIO2 | | Y |
| Ca Ion | Calcium Ion | Y |
| O2 50 | | Y |
| Alv/ArtO2 Grad | | Y |
| AlvO2 Tension | | Y |
| AlvO2 Part Pre | | Y |
| Oxy Hgb | | Y |
| DeOxy Hgb | | Y |
| VO2 | | Y |
| Tot Hgb | | Y |
| Hgb BGS | | Y |
| O2 Sat | $O_2$ Saturation | Y |
| Sample | | N |
| VPH | Venous Ph | Y |
| VPCO2 | Venous Partial $CO_2$ | Y |
| VPO2 | Venous Partial $O_2$ | Y |
| VHCO3 | Venous Bicarbonate | Y |
| VTCO2 | Venous Total $CO_2$ | Y |
| VBase Excess | Venous Base Excess | Y |
| VFIO2 | | Y |

Figure 24:
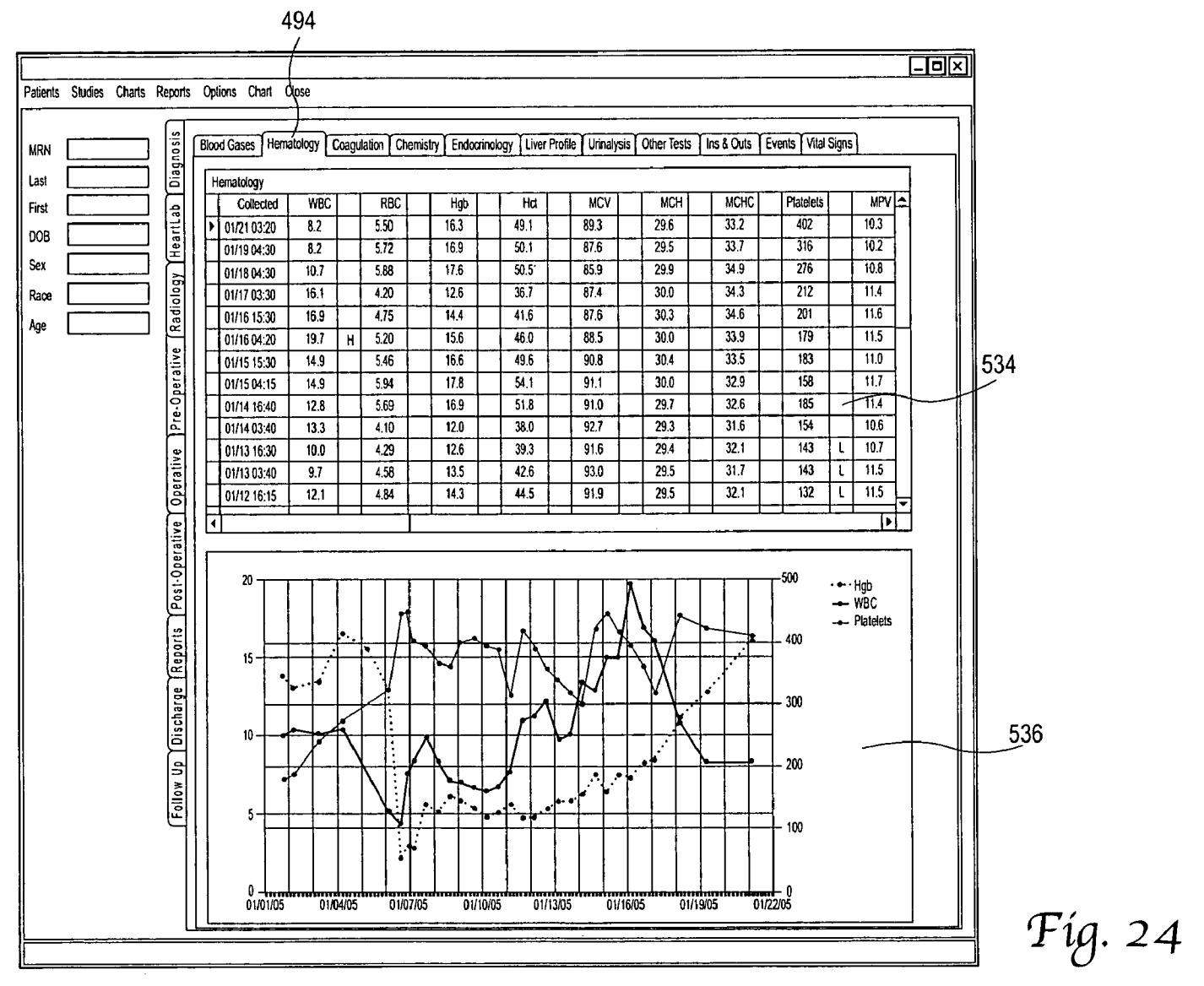

| Hematology | | | | | | | | | |
|---|---|---|---|---|---|---|---|---|---|
| Collected | WBC | RBC | Hgb | Hct | MCV | MCH | MCHC | Platelets | MPV |
| 01/21 03:20 | 8.2 | 5.50 | 16.3 | 49.1 | 89.3 | 29.6 | 33.2 | 402 | 10.3 |
| 01/19 04:30 | 8.2 | 5.72 | 16.9 | 50.1 | 87.6 | 29.5 | 33.7 | 316 | 10.2 |
| 01/18 04:30 | 10.7 | 5.88 | 17.6 | 50.5 | 85.9 | 29.9 | 34.9 | 276 | 10.8 |
| 01/17 03:30 | 16.1 | 4.20 | 12.6 | 36.7 | 87.4 | 30.0 | 34.3 | 212 | 11.4 |
| 01/16 15:30 | 16.9 | 4.75 | 14.4 | 41.6 | 87.6 | 30.3 | 34.6 | 201 | 11.6 |
| 01/16 04:20 | 19.7 H | 5.20 | 15.6 | 46.0 | 88.5 | 30.0 | 33.9 | 179 | 11.5 |
| 01/15 15:30 | 14.9 | 5.46 | 16.6 | 49.6 | 90.8 | 30.4 | 33.5 | 183 | 11.0 |
| 01/15 04:15 | 14.9 | 5.94 | 17.8 | 54.1 | 91.1 | 30.0 | 32.9 | 158 | 11.7 |
| 01/14 16:40 | 12.8 | 5.69 | 16.9 | 51.8 | 91.0 | 29.7 | 32.6 | 185 L | 11.4 |
| 01/14 03:40 | 13.3 | 4.10 | 12.0 | 38.0 | 92.7 | 29.3 | 31.6 | 154 | 10.6 |
| 01/13 16:30 | 10.0 | 4.29 | 12.6 | 39.3 | 91.6 | 29.4 | 32.1 | 143 L | 10.7 |
| 01/13 03:40 | 9.7 | 4.58 | 13.5 | 42.6 | 93.0 | 29.5 | 31.7 | 143 L | 11.5 |
| 01/12 16:15 | 12.1 | 4.84 | 14.3 | 44.5 | 91.9 | 29.5 | 32.1 | 132 | 11.5 |

| Column | Description | Indicator |
|---|---|---|
| Collec[]d | Date and time sample was collected | N |
| WBC | White Blood Count | Y |
| RBC | Red Blood Count | Y |
| Hgb | Hemoglobin | Y |
| Hct | Hematocrit | Y |
| MCV | | Y |
| MCH | | Y |
| MCHC | | Y |
| Platelets | Platelets | Y |
| MPV | | Y |
| RDW-CV | | Y |
| RDW-SD | | Y |
| NRBC | | Y |
| Abs NRBC | | Y |
| Neut | | Y |
| Lymph | | Y |
| Mono | | Y |
| Baso | | Y |
| Seg | | Y |
| Band | | Y |
| Lymph | | Y |
| Mono | | Y |
| EOS | | Y |
| Baso | | Y |
| Meta | | Y |
| ANC | | Y |
| ALC | | Y |
| AMC | | Y |
| AEC | | Y |
| ABC | | Y |
| Plt Est | | Y |
| Aniso | | Y |
| Polk | | Y |
| Poly | | Y |

*Fig. 25*

| Column | Description | Indicator |
|---|---|---|
| Collected | Date and time sample was collected | N |
| Protime | | Y |
| aPTT | | Y |
| PT Cor Heparin | | Y |
| PTT Cor Heparin | | Y |
| Fibrinogen | | Y |
| D Dimer | | Y |
| INR | | Y |

*Fig. 27*

| Column | Description | Indicator |
|---|---|---|
| Collected | Date and time sample was collected | N |
| Na | Sodium | N |
| K | Potassium | Y |
| Cl | | Y |
| CO2 | | Y |
| Anion Gap | | Y |
| Glucose | | Y |
| BUN | | Y |
| Creatinine | | Y |
| Ca | | Y |
| Phos | | Y |
| Mg | | Y |
| Albumin | | Y |
| Lactic Acid | | Y |

| Endocrinology | | | |
|---|---|---|---|
| Collected | T4 | TSH | Free T4 |
| 01/24 13:00 | 12.6 | 0.341 | |
| 01/13 03:40 | 2.6 L | 4.170 L | 0.7 L |
| 01/06 03:29 | 6.1 L | 7.860 H | |
| 01/05 18:30 | TNP | TNP | |

Fig. 31

| Liver Profile | | | | | | | |
|---|---|---|---|---|---|---|---|
| Collected | T Prot | T Bili | Conjug 6 | Unconj 8 | AST(SGO | AST(SGP | Alk Phos |
| 01/14 11:05 | | 3.7 | 0.4 | 3.3 | 31 | 18 | 95 L |
| 01/08 04:50 | 5.1 L | 9.5 | 0.2 | 9.3 | 55 | 18 | 52 L |
| 01/03 05:30 | | 9.2 | <0.1 | 9.2 | | | |
| 01/02 05:00 | | 7.3 | <0.1 | 7.3 | | | |

Fig. 32

| Column | Description | Indicator |
|---|---|---|
| Collected | Date and time sample was collected | N |
| T Port | | Y |
| T Bili | | Y |
| Conjug Bili | | Y |
| Unconj Bili | | Y |
| AST(SGOT) | | Y |
| ALT(SGPT) | | Y |
| Alk Phos | | Y |

Fig. 34

| Column | Description | Indicator |
|---|---|---|
| Collected | Date and time sample was collected | N |
| Volume | | Y |
| Color | | Y |
| Clarity | | Y |
| Protein | | Y |
| PH | | Y |
| Glucose | | Y |
| Ketone | | Y |
| Bilirubin | | Y |
| Blood | | Y |
| Urobln Dpstk | | Y |
| Leukocytes | | Y |
| Nitrite | | Y |
| WBC | | Y |
| RBC | | Y |

| Other Tests | | | | | | |
|---|---|---|---|---|---|---|
| Collected | Category | Result Type | Result | Abnormal | Units | Normal Range |
| 02/03 16:40 | LAB | BIRTHWT | NOT PROVID | | grams | |
| 02/03 16:40 | LAB | GSTAGE | NOT PROVID | | weeks | |
| 02/03 16:40 | LAB | FEEDSTAT | MILK BASE | | | |
| 02/03 16:40 | LAB | HEALTHST | SICK | | | |
| 02/03 16:40 | LAB | SPECTYPE | REPEAT | | | |
| 02/03 16:40 | LAB | COLLAGE | 34 | | days | |
| 02/03 16:40 | LAB | PKUSC | NORMAL | | | |
| 02/03 16:40 | LAB | CH | NORMAL | | | |
| 02/03 16:40 | LAB | CAH | NORMAL | | | |
| 02/03 16:40 | LAB | HGBMOP | NORMAL | | | |
| 02/03 16:40 | LAB | NBSGALTS | NORMAL | | | |
| 02/01 00:05 | LAB | HEPL | 0.68 | | IU/mL | 0.5-1.0 |
| 01/31 13:15 | LAB | HEPL | TNP | | IU/mL | 0.5-1.0 |
| 01/28 12:00 | LAB | HEPL | 1.17 | H | IU/mL | 0.5-1.0 |

Fig. 36

| Column | Description |
|---|---|
| Collected | Date and time of ins & outs summarization |
| Total Ins | Calculated field - sum of all inputs |
| Total Outs | Calculated field - sum of all outputs |
| PRBC | Packed red blood cells input |
| FFP | Fresh frozen plasma input |
| Plts | Platelets input |
| Cryo | Cryoprecipitate input |
| Sequ | Sequestered blood input |
| Cell Svr | Cell saver blood input |
| Alb 5% | 5% Albumin input |
| Alb 25% | 25% Albumin input |
| TPN | Total parenteral nutrition input |
| IV Meds | Intravenous medications input |
| IV Fluids | Intravenous fluids input |
| PG | By gastric tube input |
| PO | By mouth input |
| Other Ins | All other inputs |
| Mediastinal | Mediastinal chest tube output |
| Pl Left | Pleural left chest tube output |
| Pl Right | Pleural right chest tube output |
| Urine | Urine output |
| UF | Ultrafiltration output |
| Emesis | Emesis output |
| Blood | Blood output |
| Other Outs | All other outputs |

Study Patients Report

MainReport

Friday, June 10, 2005
1:17:26PM
Marcy Torrams at desk 1627

Children's Mercy
HOSPITALS & CLINICS
www.childrens-mercy.org

Study Patients Information

Project Name: CHSS Amendment I (Tricuspid Atresia)
IRB #: 03 03-033E

| Patient ID | Med Rec No | Patient Name | Enroll Date |
|---|---|---|---|
| 21878 | | | 04/07/2000 |
| 18784 | | | 05/18/2000 |
| 39540 | | | 06/08/2000 |
| 51529 | | | 09/27/2000 |
| 53295 | | | 11/04/2000 |
| 18781 | | | 07/13/2001 |
| 21879 | | | 09/20/2001 |
| 18780 | | | 10/03/2001 |
| 53244 | | | 03/10/2003 |
| 20730 | | | 07/01/2003 |
| 41101 | | | 05/18/2004 |
| | | | 07/16/2004 |
| 53530 | | | 06/09/2005 |

752
778
780
782
776

Current Page No: 1    Total Page No: 1    Zoom Factor: 100%

| Lab Result Name | Test Type | Range Chart | Run Chart |
| --- | --- | --- | --- |
| Creatinine | Chemistry | Y | Y |
| Glucose | Chemistry | Y | Y |
| K | Chemistry | Y | Y |
| Lactic Acid | Chemistry | Y | Y |
| Mg | Chemistry | Y | Y |
| Na | Chemistry | Y | Y |
| Phos | Chemistry | Y | Y |
| aPTT | Coagulation | Y | Y |
| Fibrinogen | Coagulation | Y | Y |
| HaPTT | Coagulation | N | Y |
| HPT | Coagulation | N | Y |
| INR | Coagulation | N | Y |
| Protime | Coagulation | Y | Y |
| Free T4 | Endocrinology | Y | Y |
| T4 | Endocrinology | Y | Y |
| TSH | Endocrinology | Y | Y |
| ABC | Hematology | Y | Y |
| Abs NRBC | Hematology | N | Y |
| AEC | Hematology | Y | Y |
| ALC | Hematology | Y | Y |
| AMC | Hematology | Y | Y |
| ANC | Hematology | Y | Y |
| Band | Hematology | N | Y |
| Baso | Hematology | N | Y |
| Baso | Hematology | N | Y |
| EOS | Hematology | N | Y |
| Hct | Hematology | Y | Y |
| Hgb | Hematology | Y | Y |
| Lymph | Hematology | N | Y |
| MCH | Hematology | Y | Y |
| MCHC | Hematology | Y | Y |
| MCV | Hematology | Y | Y |
| Meta | Hematology | N | Y |
| Mono | Hematology | N | Y |
| MPV | Hematology | Y | Y |
| Neut | Hematology | N | Y |
| NRBC | Hematology | N | Y |
| Platelets | Hematology | Y | Y |
| RBC | Hematology | Y | Y |
| RDW-CV | Hematology | Y | Y |
| RDW-SD | Hematology | Y | Y |
| Seg | Hematology | N | Y |
| WBC | Hematology | Y | Y |
| Alk Phos | Liver Profile | Y | Y |
| ALT(SGPT) | Liver Profile | Y | Y |
| AST(SGOT) | Liver Profile | Y | Y |
| Conjug Bili | Liver Profile | Y | Y |
| T Bili | Liver Profile | Y | Y |
| T Prot | Liver Profile | Y | Y |
| Unconj Bili | Liver Profile | Y | Y |

*Fig. 63*

SYSTEM AND METHOD FOR COLLECTING, ORGANIZING AND PRESENTING RESEARCH-ORIENTED MEDICAL INFORMATION

RELATED APPLICATIONS

The present application is a nonprovisional patent application and claims priority benefit, with regard to all common subject matter, of earlier-filed U.S. provisional patent application titled "SYSTEM AND METHOD OF COLLECTING, ORGANIZING, AND ANALYZING MEDICAL INFORMATION", Ser. No. 60/694,160, filed Jun. 27, 2005. The identified earlier-filed application is hereby incorporated by reference into the present application.

BACKGROUND OF THE INVENTION

1. Field of the Invention

The present invention relates to the field of computer-assisted medical research. More particularly, the invention relates to a method and computer program for electronically collecting, organizing, and presenting medical research study information and laboratory test information.

2. Description of the Prior Art

Doctors, nurses, and other care givers often work with large groups of patients and collect a large amount of information relating to each patient. It is not only important that such information be accurate and up to date, but the information must be managed efficiently to enable caregivers to quickly access the information they need without sifting through the entire body of information.

Computer programs have been developed to assist in the collection and storage of patient medical information. For example, hospital information systems (HIS) are currently used by hospitals to store and retrieve information relating to the administrative and clinical aspects of the hospital's services. Furthermore, various computer-based imaging systems are used to store, retrieve, view, and manipulate images that are created for patient treatment, research, or both.

Prior art systems of managing medical information enable caregivers to quickly store and retrieve information relating to a particular patient. Unfortunately, however, these systems suffer from various problems and limitations. For example, users must use several different systems to obtain the information created by each system, and are limited to retrieving and viewing information relating to a single patient at a time.

Accordingly, there is a need for an improved system and method of collecting, organizing, and presenting patient information.

SUMMARY OF THE INVENTION

The present invention solves the above-described problems and provides a distinct advance in the art of medical information software. More particularly, the present invention involves a method and computer program for electronically collecting, organizing, and presenting medical research study information and laboratory test information.

According to a first embodiment of the invention, the computer program runs on a standard personal computer (PC) or similar device, and comprises code segments for electronically managing medical research studies as well as laboratory test results. A study setup code segment presents a user interface that receives new study information from a user and sets up a new study, and a study comments code segment receives comments from members of the study, stores the comments, enables users to edit the comments, and presents the comments for review. A view user studies code segment determines a current program user, presents for review a list of all studies of which the user is a member, and presents detailed information relating to a study selected by the user from the list of studies.

The program further comprises an events code segment for receiving event information from the user, wherein the event information includes a date of the event, and a laboratory communications code segment for maintaining a communications link with a laboratory information system. The laboratory communications code segment further electronically receives a laboratory test result from the laboratory information system, wherein the test result includes a date of the test and a value of the result. A chart code segment creates a laboratory test results chart, wherein the chart includes a visual indication of the value of the test result and a visual indication of the date of the event relative to the date of the test.

A second embodiment of the invention comprises an events code segment, a laboratory communications code segment, and a chart code segment. The events code segment receives information from a user relating to a plurality of medical complications and a plurality of medical procedures, wherein the information includes a date and a description of each complication and each procedure.

The laboratory communications code segment maintains a communications link with a laboratory information system and electronically receives a plurality of laboratory test results from the laboratory information system, wherein each of the test results includes a plurality of values each taken at a different time. The chart code segment creates a laboratory test results chart including a timeline, a graph for each laboratory test result, and a milestone indicator for each complication and each procedure. Each graph is plotted so that it corresponds to the timeline and each milestone indicator is placed to correspond to a time of the timeline, and the description of each complication and each procedure is selectively visible and is associated with the milestone corresponding to the complication or procedure.

A third embodiment of the invention comprises a study setup code segment for presenting a user interface that receives new study information from a user and sets up the new study in a computer system, wherein the new study information includes study type, study status, enrollment status, IRB information, a project description, project goals, inclusion criteria, and exclusion criteria. A members code segment adds members to a study, removes members from the study, and indicates a role for each member, wherein member roles are chosen from the group consisting of primary investigator, study coordinator, sub-investigator, and inactive.

A patients code segment adds new patients to a study, presents study patient information for review, removes patients from the study, and indicates a status of each patient, wherein each patient's status is chosen from the group consisting of inactive, excluded, and expired, and wherein each patient is assigned an non-traceable patient identification number and identified by the identification number in study. A study comments code segment receives comments from members of the study, stores the comments, edits the comments, and presents the comments for review, wherein each comment is assigned a receiving date, a status, a responsible member, and a priority.

A study parameters code segment configures data to be stored in a database associated with the research study. A view user studies code segment determines a current program user, presents for review a list of all studies of which the user is a member, and presents detailed information relating to a study selected by the user from the list of studies. A view all studies code segment presents for review a list of all studies maintained by the program and prevents the user from viewing detailed information relating to a study.

These and other important aspects of the present invention are described more fully in the detailed description below.

BRIEF DESCRIPTION OF THE DRAWING FIGURES

A preferred embodiment of the present invention is described in detail below with reference to the attached drawing figures, wherein:

FIG. 5 is a procedure form presented when the user selects a view procedure menu item of a context menu associated with a procedures activity window;

FIG. 6 is an add patient form presented when the user selects an add patient to rounds menu item of a context menu associated with a rounds activity window;

FIG. 9 is a rounds report created when the user selects a create rounds report menu item of the context menu associated with the rounds activity window;

FIG. 14 is an exemplary heart lab tab of the user interface of FIG. 11;

FIG. 16 is an exemplary radiology tab of the user interface of FIG. 11;

FIG. 19 is an exemplary studies tab of the user interface of FIG. 11;

FIG. 21 is the interface of FIG. 20 illustrating another aspect of the operative tab;

FIG. 23 is an exemplary table of laboratory test results that may be presented in the blood gases element of the post-operative tab of FIG. 22;

FIG. 24 is the interface of FIG. 22, illustrating a hematology element of the post-operative tab;

FIG. 25 is a table of exemplary laboratory test results that may be presented in the hematology element of the post-operative tab of FIG. 24;

FIG. 27 is a table of exemplary laboratory test results that may be presented in the coagulation element of the post-operative tab of FIG. 26;

FIG. 29 is a table of exemplary laboratory test results that may be presented in the chemistry element of the post-operative tab of FIG. 28;

FIG. 30 is the interface of FIG. 22 illustrating an endocrinology element of the post-operative tab;

FIG. 31 is the interface of FIG. 22 illustrating a liver profile element of the post-operative tab;

FIG. 32 is a table of exemplary laboratory test results that may be presented in the liver profile element of the post-operative tab of FIG. 31;

FIG. 33 is the interface of FIG. 22 illustrating a urinalysis element of the post-operative tab;

FIG. 34 is a table of exemplary laboratory test results that may be presented in the urinalysis element of the post-operative tab of FIG. 33;

FIG. 35 is the interface of FIG. 22 illustrating an "other tests" element of the post-operative tab;

FIG. 36 is the interface of FIG. 22 illustrating an "ins & outs" element of the post-operative tab of the interface;

FIG. 37 is a table of exemplary laboratory test results that may be presented in the ins & outs element of the post-operative tab of FIG. 36;

FIG. 38 is an exemplary data entry form for submitting intake and output information associated with the ins & outs element of FIG. 36;

FIG. 39 is the interface of FIG. 22 illustrating an events element of the post-operative tab;

FIG. 40 is an exemplary data entry form for submitting event information associated with the events element of FIG. 39;

FIG. 41 is the interface of FIG. 22 illustrating a vital signs element of the post-operative tab;

FIG. 45 is the interface of FIG. 20 illustrating a reports tab of the user interface;

FIG. 46 is the interface of FIG. 45 illustrating a report generated by the program and presented via the reports tab;

FIG. 48 is the interface of FIG. 47 illustrating a members tab of the interface;

FIG. 50 is the interface of FIG. 47 illustrating a patients tab of the interface;

FIG. 52 is an exemplary form that presents identification information about patients participating in a study associated with the interface of FIG. 47;

FIG. 63 is a table of exemplary lab tests and lab test types associated with the form of FIG. 62;

DETAILED DESCRIPTION OF THE PREFERRED EMBODIMENTS

Figure 1:
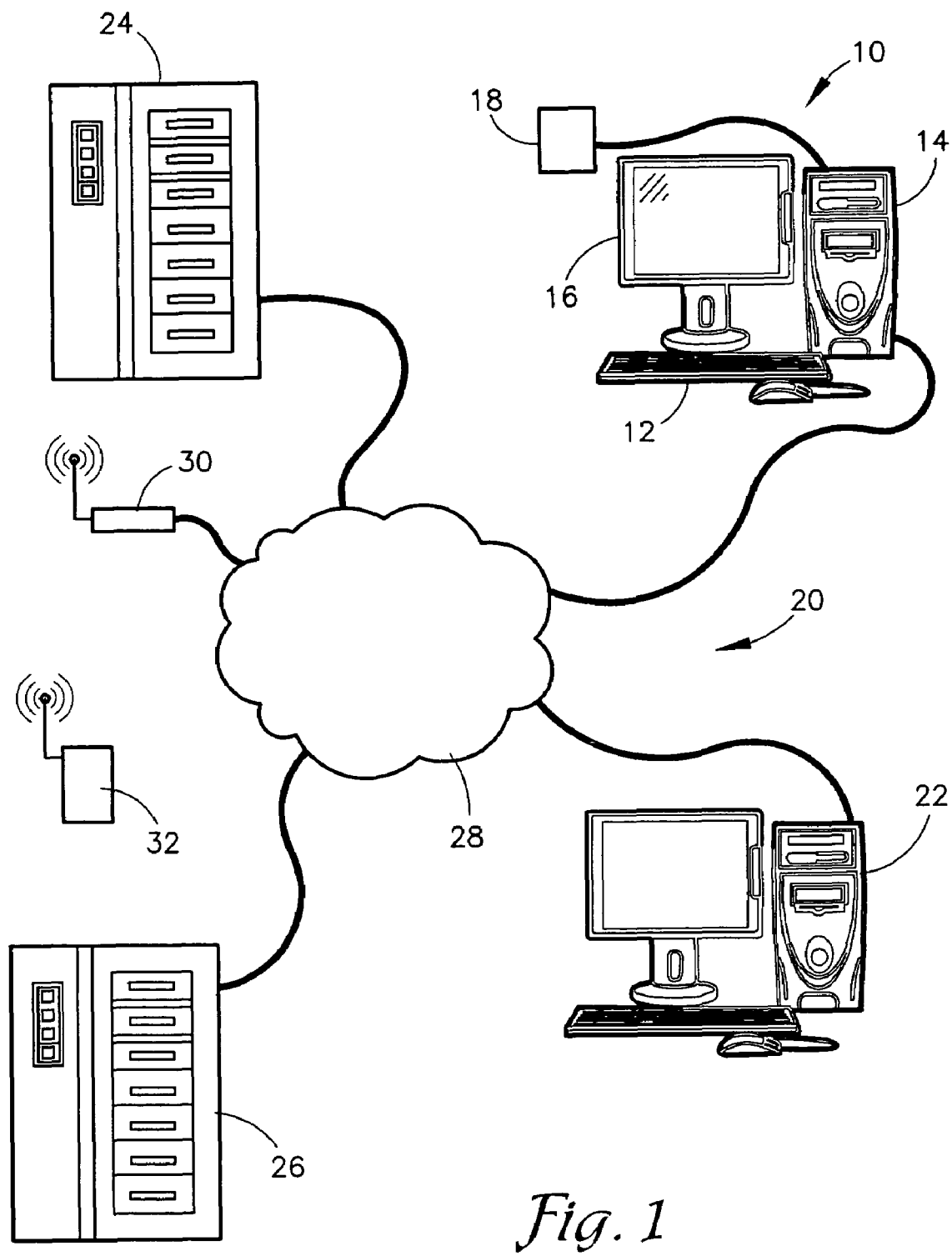
FIG. 1 is a schematic view of an exemplary computer network for implementing the present invention.

The present invention relates to a system and method of collecting, organizing, and presenting patients' medical information. The method of the present invention is especially well-suited for implementation on a computer or computer network, such as the computer 10 illustrated in FIG. 1 that includes a keyboard 12, a processor console 14, a display 16, and one or more peripheral devices 18, such as a scanner or printer. The computer 10 may be a part of a computer network, such as the computer network 20 that includes one or more client computers 10,22 and one or more server computers 24,26 and interconnected via a communications system 28. The present invention may also be implemented, in whole or in part, on a wireless communications system including, for example, a network-based wireless transmitter 30 and one or more wireless receiving devices, such as a hand-held computing device 32 with wireless communication capabilities. The present invention will thus be generally described herein as a computer program. It will be appreciated, however, that the principles of the present invention are useful independently of a particular implementation, and that one or more of the steps described herein may be implemented without the assistance of a computing device.

The present invention can be implemented in hardware, software, firmware, or a combination thereof. In a preferred embodiment, however, the invention is implemented with a computer program. The computer program and equipment described herein are merely examples of a program and equipment that may be used to implement the present invention and may be replaced with other software and computer equipment without departing from the scope of the present invention.

The computer program of the present invention is stored in or on a computer-readable medium residing on or accessible by a host computer for instructing the host computer to implement the method of the present invention as described herein. The host computer may be a server computer, such as server computer 24, or a network client computer, such as computer 10. The computer program preferably comprises an ordered listing of executable instructions for implementing logical functions in the host computer and other computing devices coupled with the host computer. The computer program can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions.

The ordered listing of executable instructions comprising the computer program of the present invention will hereinafter be referred to simply as "the program" or "the computer program." It will be understood by those skilled in the art that the program may comprise a single list of executable instructions or two or more separate lists, and may be stored on a single computer-readable medium or multiple distinct media. The program will also be described as comprising various "code segments," which may include one or more lists, or portions of lists, of executable instructions. Code segments may include overlapping lists of executable instructions—that is, a first code segment may include instruction lists A and B, and a second code segment may include instruction lists B and C.

In the context of this application, a "computer-readable medium" can be any means that can contain or store the program for use by or in connection with the instruction execution system, apparatus, or device. The computer-readable medium can be, for example, but not limited to, an electronic, magnetic, optical, electro-magnetic, or semi-conductor system, apparatus, or device. More specific, although not inclusive, examples of the computer-readable medium would include the following: a portable computer diskette, a random access memory (RAM), a read-only memory (ROM), an erasable, programmable, read-only memory (EPROM or Flash memory), an optical fiber, and a portable compact disk read-only memory (CDROM).

Figure 2:
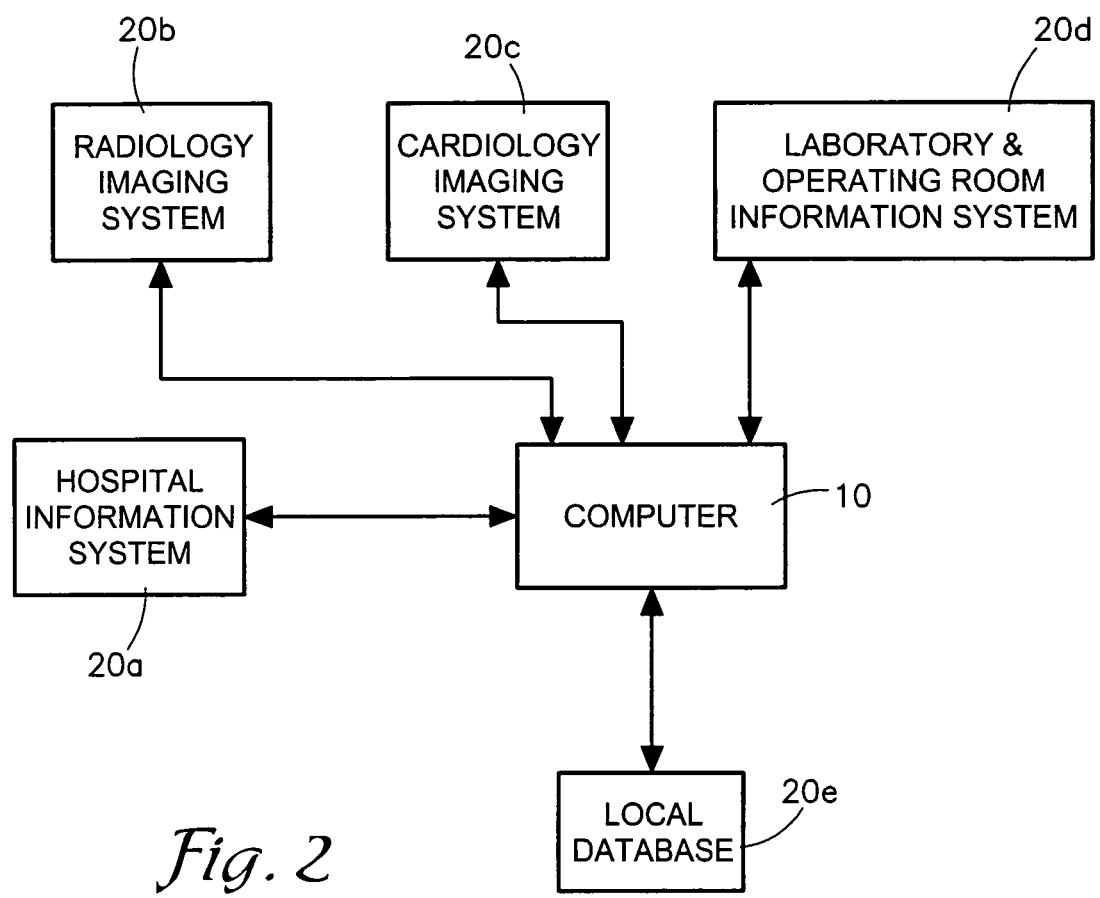
FIG. 2 is a schematic view of the interconnection between a computer of the network of FIG. 1 and various databases and systems of the network.

Referring to FIG. 2, the program is operable to communicate with various pre-existing, computer-based hospital information and imaging systems to request and receive patient-related and other medical and research information and present the information on the host computer as a single point of information access. The computer 10 may communicate, for example, with a hospital information system (HIS) 20a; a radiology imaging system 20b; a cardiology imaging system 20c; a laboratory and operating room information system 20d; and a local database 20e. The HIS 20a is a computer-assisted system designed to store, manipulate and retrieve information concerned with the administrative and clinical aspects of providing services within the hospital. An exemplary HIS is sold by MEDICAL INFORMATION TECHNOLOGY, INC.™ The radiology imaging system 20b manages radiological images, and an exemplary radiology imaging system is SYNAPSE™ sold by FUJIFILM MEDICAL SYSTEMS USA, INC.™ The cardiology imaging system 20c is similar to the radiology imaging system 20b, except that the cardiology imaging system 20c manages cardiology images. The laboratory and operating room information system 20d manages laboratory operating room data, and an exemplary system 20d is sold by MEDITECH™.

If the program of the present invention is implemented on the first server 24, for example, one or more of the hospital information and imaging systems may be running on the server 26, wherein the program communicates with the server 26 via the communications network 28. The program may also receive all or a portion of the information directly from users. The program creates a series of interactive user interfaces for presenting the information in a user-viewable form and for enabling users to communicate directly with one or more of the hospital information and imaging systems. The interactive user interfaces can generally be classified according to the information presented by each interface. A group of interfaces that present related information are collectively referred to herein as a "view." The program generally presents a department view, a patient view, a visit view, and a research view, as explained below.

The Department View

Figure 3:
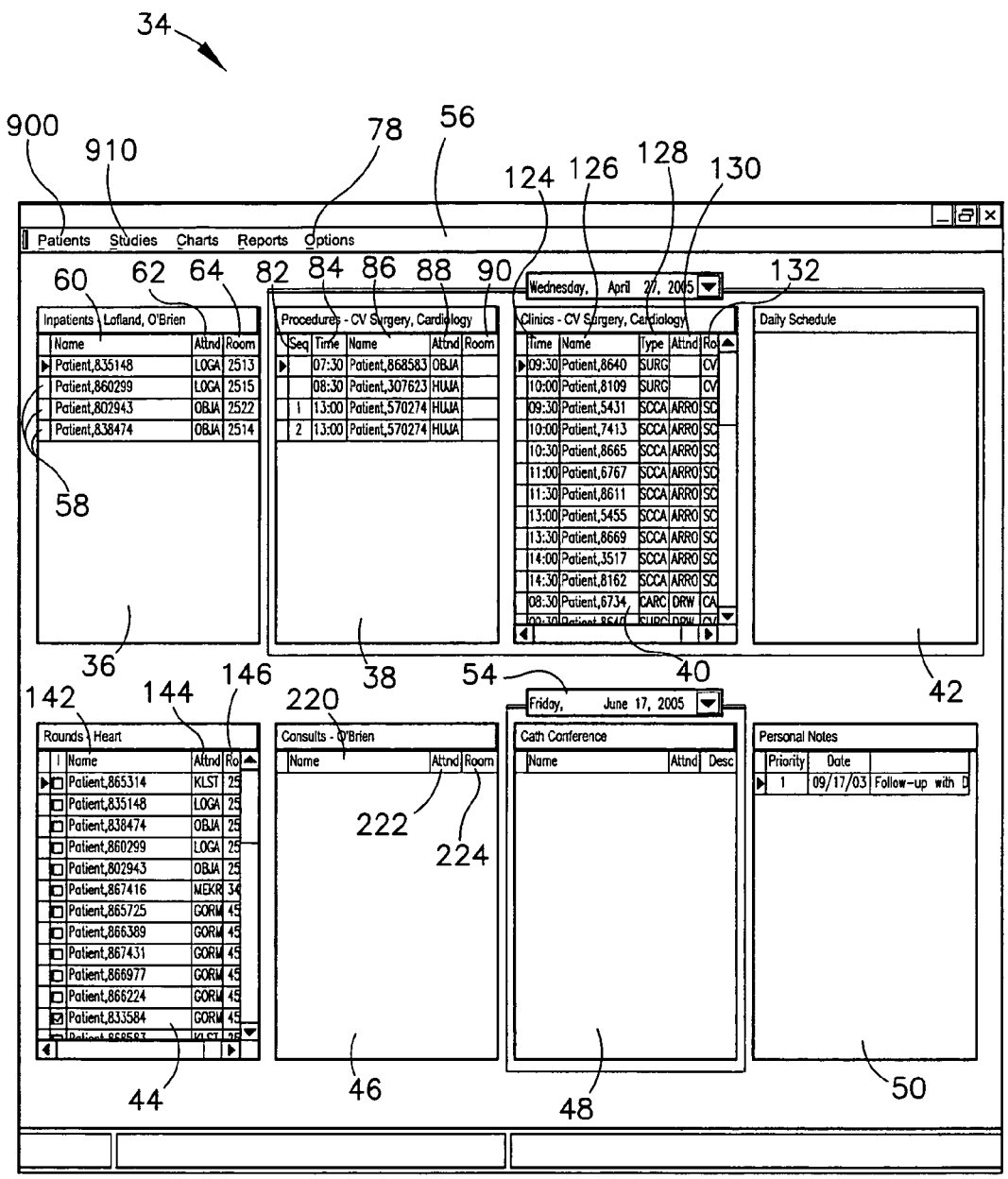
FIG. 3 is a top-level user interface associated with a department view of the present invention presenting a plurality of activity windows.

Referring to FIG. 3, the department view presents a top-level interface 34 that enables physicians, nurses, clinical care givers and other users to view activities and information associated with patients and particular groups of patients for a particular day. The illustrated department view interface 34 includes eight activity windows, wherein each window presents information according to certain parameters. The illustrated activity windows include inpatients 36, procedures 38, clinics 40, daily schedule 42, rounds 44, consults 46, cath conference 48, and personal notes 50 activity windows. The program preferably presents the activity windows simultaneously, so that the user can quickly and easily scan the information presented in each window without having to navigate multiple user interface pages.

The department view interface 34 also includes one or more date selectors 52,54, wherein each date selector enables the user to quickly choose a date associated with one or more of the activity windows. The illustrated interface 34 includes two drop-down calendar date selectors 52,54. A first date selector 52 enables a user to select a date pertaining to the procedures 38, clinics 40, and daily schedule 42 activity windows. A second drop-down date selector 54 enables the user to select a date pertaining to the cath conference activity window 48. When the department view interface 34 is first presented, the default value for the first date selector 52 is the current date. The default value for the second date selector 54 is a pre-determined day of the week. If catheterization conferences are held on Friday mornings, for example, the default value for the second date selector 54 is the Friday following the current date. The user may then choose another date from either date selector 52,54 to view events associated with that particular day. The date selectors 52,54 are also presented simultaneously with the activity windows.

Figure 4:
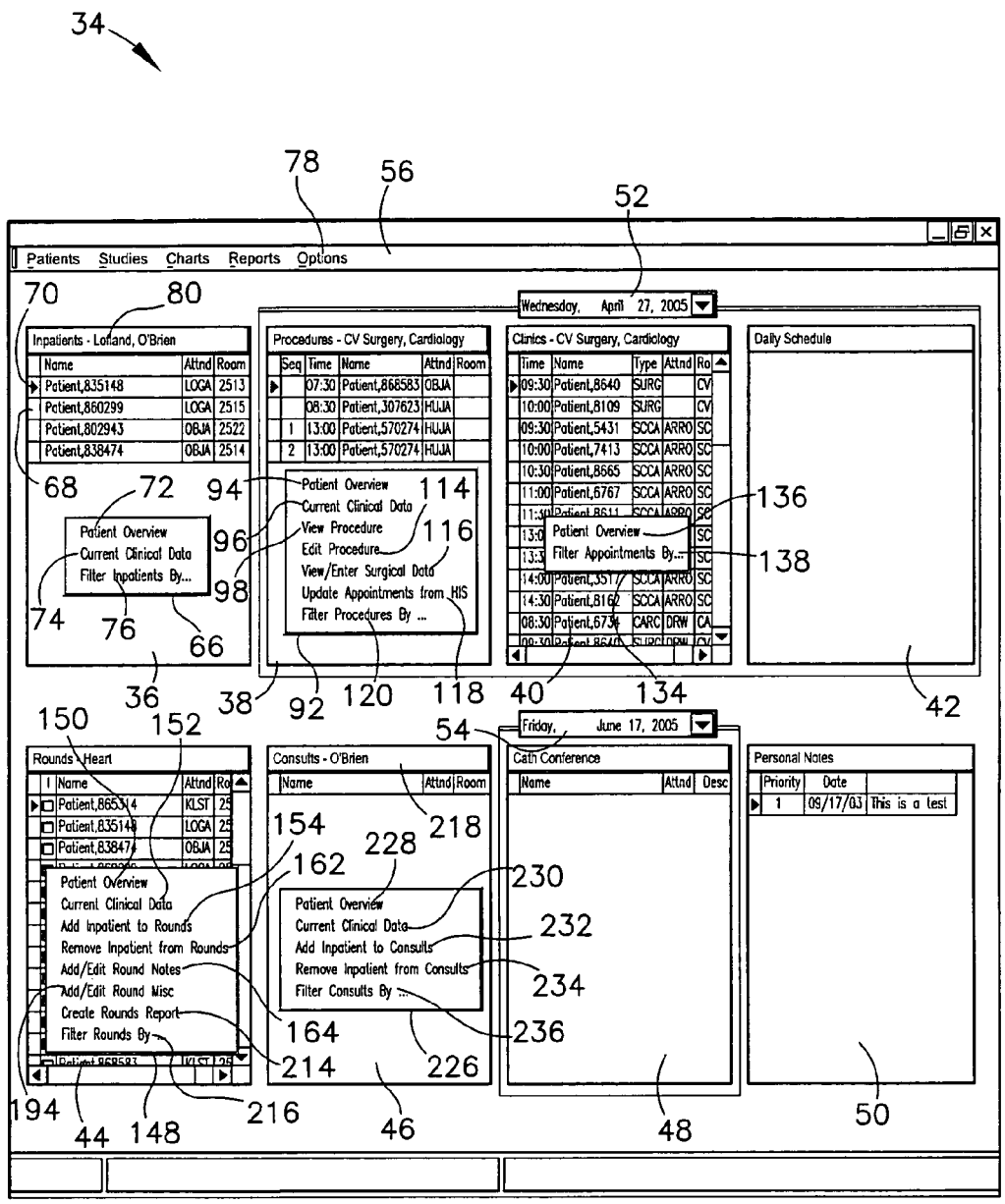
FIG. 4 is the user interface of FIG. 3 illustrated with context menus that are associated with various of the activity windows.

A menu toolbar 56 is located near a top of the interface 34, and a specific context menu is associated with each activity window (see FIG. 4). The menu toolbar 56 enables the user to perform functions and select items and options that are global in nature and thus pertain to the department view generally as well as one or more other views of the program, and are not associated with a specific activity window. The context menus enable the user to perform functions and select parameters and options that are associated with a specific activity window, and to "drill down" to obtain more detailed information about a selected patient or activity that is located within a specific activity window. The context menu associated with each activity window is preferably a "pop-up" menu activated when the user positions an on-screen pointer or arrow over the specific activity window and selects a designated input button, such as a computer mouse button.

The Inpatients Activity Window

The inpatients activity window 36 presents information about patients currently admitted to the hospital or to one or more departments or services of the hospital. Upon admission to the hospital, each inpatient is assigned a service, a team, and an attending physician. Patients may be included in the inpatients activity window 36 while they are admitted to any service of the hospital, or may be included in the inpatients activity window 36 only upon being assigned to a designated hospital service, group of services, physician, or group of physicians. Inpatients are automatically included in the illustrated inpatients activity window 36 when they are assigned to a particular service or services, such as cardiovascular surgery or cardiology services, or are assigned to a physician associated with these services. The program also automatically removes patients from the window 36 when they are no longer assigned to one of these services or associated physicians.

The program automatically updates the inpatients activity window 36 by adding patients who are assigned to one of the designated services or physicians, and by removing patients who are no longer assigned to one of the designated services or physicians. These automatic updates occur at a predefined or user-defined interval, such as every five minutes. The program determines patients' status by communicating with a hospital information system, or "HIS," to receive the information as recorded in the HIS.

As illustrated, the inpatient activity window 36 presents a plurality of rows 58 of information, wherein each row 58 pertains to a particular patient. The illustrated information includes each patient's full name 60, an attending physician identifier 62 indicating which physician is currently attending the patient, and a current location 64 of the patient. The physician identifier 62 may be the first four characters of the physician's last name, and the location information may be a room number.

An inpatients context menu 66 is illustrated in FIG. 4, wherein the context menu 66 appears when the user positions the on-screen pointer over the inpatient activity window 36 and presses the designated input button, as explained above. The context menu 66 enables users to perform functions and select parameters and options that are associated with the inpatients activity window 36, and to drill down to obtain more detailed information about a selected patient.

The context menu 66 generally presents two types of menu items: 1) patient-specific items and 2) items that are not patient-specific. Patient-specific items reveal more detailed information about a selected patient, therefore the user must select a specific patient in the inpatient activity window 36 prior to activating the context menu 66 and selecting a patient-specific menu item. The user selects a specific patient within the inpatients activity window 36 by positioning the on-screen pointer over a small box 68 just to the left of the name 60 of the patient to be selected and pressing the designated mouse button. If the patient has been properly selected a pointer 70 will appear within the gray box 68 and the entire row corresponding to the patient will change color to highlight the row. The user may then activate the context menu 66 and select a patient-specific menu item relating to the selected patient.

The inpatient activity window context menu 66 presents three menu items, including patient overview 72, current clinical data 74, and filter patients by 76. The patient overview 72 and current clinical data 74 menu items are patient specific, while the filter patients by 76 menu item is not patient specific. Selecting the patient overview menu item 72 causes the program to present more information about the selected patient. In one embodiment, the program launches a patient view user interface for the corresponding patient when the user selects the patient overview menu item 72. The patient view is explained below, and therefore will not be described here.

Selecting the current clinical data menu item 74 causes the program to present more clinical information about the selected patient. In one embodiment, the program launches a visit view user interface (see FIG. 7-1) for the corresponding patient when the user selects the current clinical data menu item 74. The visit that is displayed in the visit view user interface is the current patient visit, wherein clinical data is displayed beginning with the date and time the visit view is opened. The amount of clinical data displayed will depend on the user-defined value of a lab "lookback" period. Clinical data is displayed even if it spans multiple visits as long as it is within the lookback period. The default lab lookback period is seven days, but may be user-defined via an options menu 78 of the menu toolbar 56. The visit view is discussed in greater detail below.

Selecting the filter inpatients by menu item 76 enables the user to determine how the patients listed in the inpatient activity window 36 are filtered, or presented. The user may designate, for example, filter parameters such as one or more services, teams, or attending physicians to use in selecting patients to include in the inpatients activity window 36. A current filter parameter 80 is indicated at a top of the inpatients activity window 36, wherein the parameter includes two physicians—Lofland and O'Brien—so that the patients listed in the inpatients activity window are all of the patients with Lofland and O'Brien as attending physicians.

The Procedures Activity Window

The procedures activity window 38 presents information relating to patients who have had, or are scheduled to have, one or more medical procedures performed on the date designated by the first date selector 52. In the illustrated embodiment, the medical procedures are surgical procedures performed by one or more designated departments, including procedures performed by the cardiovascular surgery department and catheterization procedures performed by the cardiology department. As illustrated in FIG. 3, the department or departments are indicated at a top of the procedures activity window.

The procedures activity window 38 presents one row of information pertaining to each patient. The information includes a sequence 82, which is the sequence in which multiple procedures will be done by one physician; a time 84, which is the date and time of the corresponding procedure; the full name 86 of the patient; attending physician 88, which is an identifier of the physician who will be performing the procedure; and a room 90, which is the location where the procedure is to be performed.

A procedures context menu 92 is associated with the procedures activity window 38, and is similar in form and function to the inpatients context menu 66 described above. Patient overview 94 and current clinical data 96 menu items function substantially identically to the patient overview 72 and current clinical data 74 menu items, respectively, described above in relation to the inpatients context menu 66 and therefore will not be discussed in detail here.

Figures 5, 6:
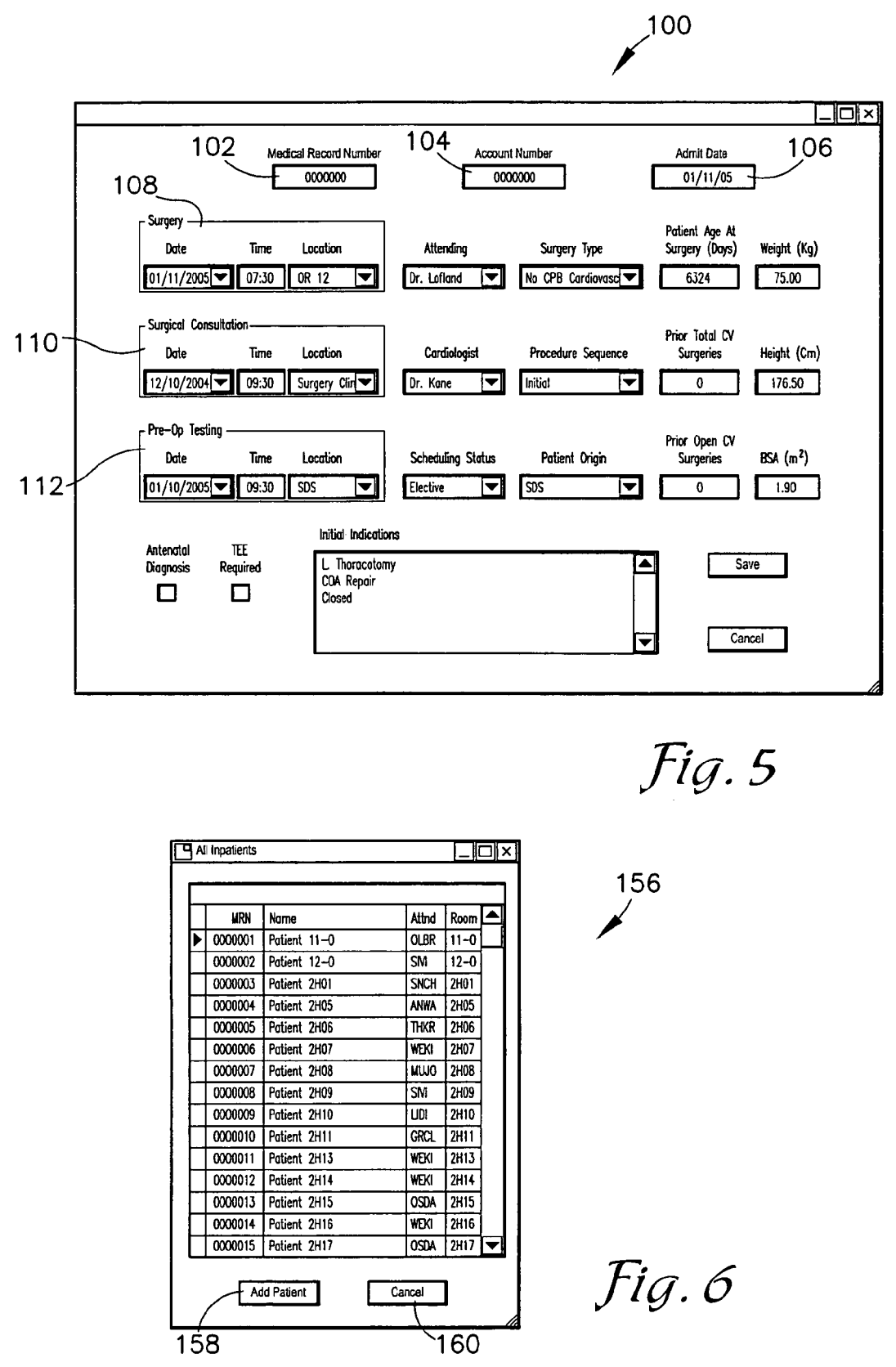

A view procedure 98 menu item is a patient specific menu item that presents procedure information relating to a selected patient. An exemplary procedure form 100 is illustrated in FIG. 5, wherein the procedure form 100 presents surgical procedure information. The information presented as part of the illustrated form 100 includes the patient's medical record number 102, account number 104, admission date 106, surgery information 108, surgical consultation information 110, pre-operation testing information 112, as well as various other pieces of information understood by those skilled in the art. When invoked via the view procedure menu item 98, the program presents the patient procedure form 100 in a protected mode so that the form data cannot be altered by the user. The form information relates to the scheduled procedure of the patient selected in the procedures activity window 38.

The edit procedure 114 menu item is similar to the view procedure 98 menu item, except that selecting the edit procedure 114 menu item enables the user to add, change, or remove information relating to a particular procedure. When selected, the edit procedure 114 menu item opens the procedure form 100 in an unprotected mode so that one or more of the data fields may be altered by the user. To avoid unauthorized users from altering the procedure information, the program only allows designated users to select this menu item, such as users with the role of system administrator, administrator, or doctor.

Figure 20:
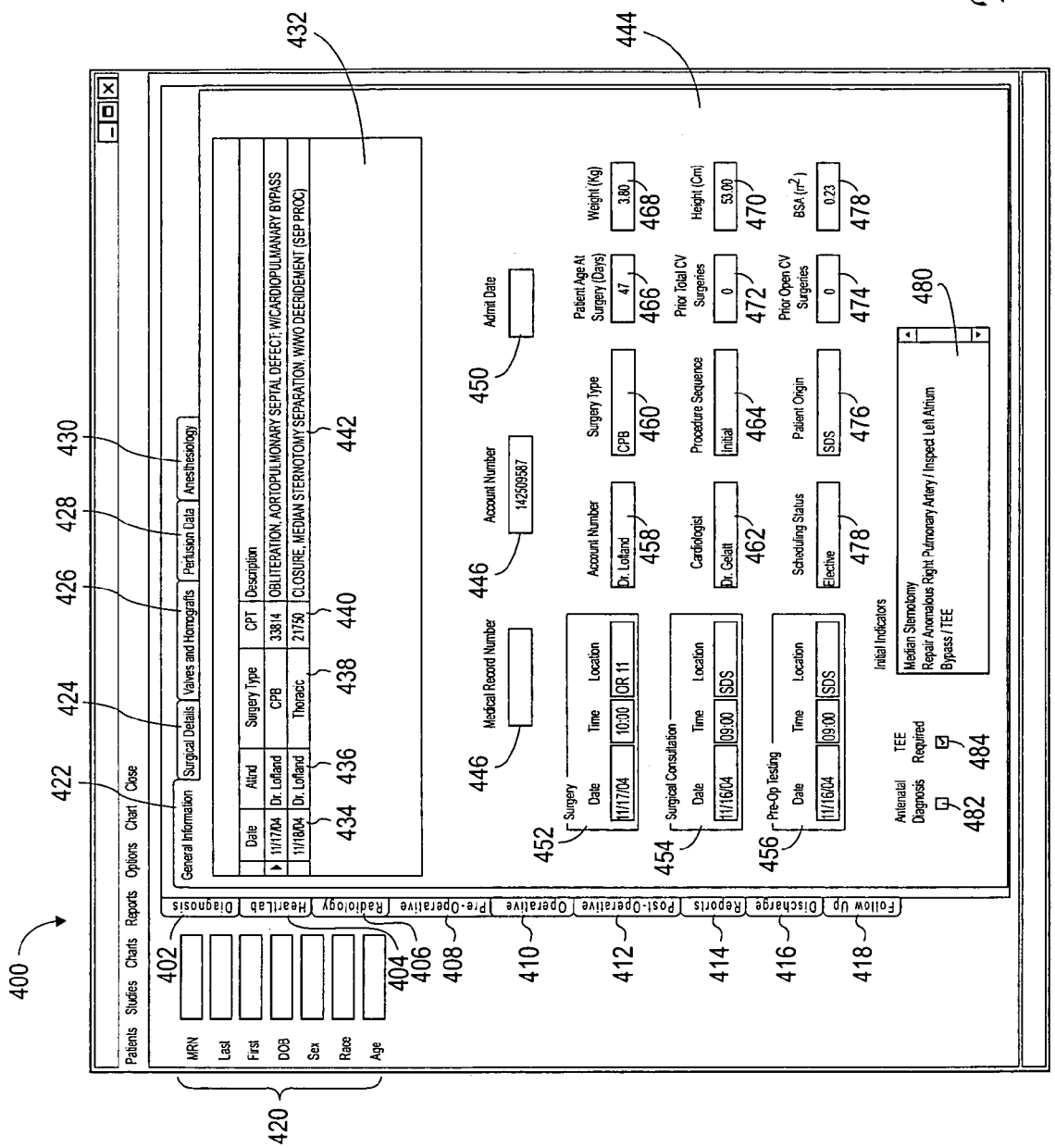
FIG. 20 is an exemplary top-level user interface associated with a visit view of the present invention and illustrating an operative tab of the interface.

The view/enter surgical data 116 menu item is also a patient specific menu item that can be selected only be designated users, such as those with the role of system administrator, administrator, or doctor. When selected, the view/enter surgical data 116 menu item opens the visit view to the operative tab (410) as illustrated in FIG. 20. The patient's visit associated with the selected procedure in the procedures activity window 38 will be opened and the operative tab will display all surgical procedures that occurred during that visit. As illustrated in FIG. 20, the operative tab presents procedure information in substantially the same format as the procedure form 100. The visit view is described in greater detail below.

Selecting the update appointments from HIS 118 menu item causes the program to update the scheduled appointments and surgical procedures of the program with any cardiovascular surgery or cardiology appointments that have recently been added, changed, or deleted by or through the hospital information system (HIS). The update appointments from HIS 118 menu item is a non-specific context menu item that can be selected only by designated users, such as those with the role of system administrator and administrator. If a new cardiovascular surgery appointment is received, the program will also automatically create a minimal dataset of surgical information and associate the dataset with that particular surgical appointment. A user can thus add more detailed information relating to the new appointment as the information becomes available. The program is operable to automatically go through this process of updating appointments at predefined or user-defined intervals, such as every ten minutes, to ensure that all appointment data is updated on a timely basis.

The filter procedures by 120 menu item is similar to the filter inpatients by 76 menu item of the inpatient context menu 66, described above. Selecting the filter procedures by 120 menu item of the procedures context menu 92 enables the user to determine how the patients listed in the procedures activity window 38 are filtered, or presented. The user may designate, for example, filter parameters such as one or more services, teams, or attending physicians to use in selecting patients to include in the procedures activity window 38. The filter function is discussed in greater detail below. A current filter parameter 122 is indicated at a top of the procedures activity window 38.

The Clinics Activity Window

The clinics activity window 40 presents information relating to clinical appointments on a date determined by the first date selector 52. The illustrated activity window 40 presents a list of patients who have had, or are scheduled to have, one or more non-surgical or non-catheterization appointments on the date indicated by the first date selector 52. The clinics activity window 40 includes appointments at, for example, cardiology clinics, as well as surgery pre-operation, and surgery follow-up appointments at one or more hospital locations. As illustrated in FIG. 4, the specific groups or individuals displayed in the clinics activity window 40 is indicated at a top of the window 40.

The clinics activity window 40 presents one row of information pertaining to each patient. The information includes a time 124 of the clinic appointment; full name 126 of the patient; type of appointment 128; attending physician identifier 130, identifying the physician with whom the appointment is scheduled; and room 132 where the clinic appointment will be held.

A clinics context menu 134 associated with the clinics activity window 40 is also illustrated in FIG. 4. The clinics context menu 134 is similar in form and function to the inpatients context menu 66 described above. The patient overview 136 and filter appointments by 138 menu items function substantially identically to the patient overview 72 and filter inpatients by 76 menu items described above in relation to the inpatients context menu 66, and therefore will not be described in detail here.

The Daily Schedule Activity Window

The daily schedule activity window 42 displays the user's daily schedule for the date corresponding to the first date selector 52. The user may view today's schedule, for example, or the schedule of another day by changing the first date selector 52.

The Rounds Activity Window

The rounds activity window 44 presents patient information oriented toward one or more teams, such as a heart team, perfusion team, and so forth. A team typically includes two or more doctors, but may include a single doctor in some circumstances. Teams transcend the boundaries of services or attending physicians, and often include patients until they are discharged from the hospital, regardless of changes in attending physician, services, or both. As illustrated in FIG. 3, a title bar 140 of the rounds activity window 44 displays which team the listed patients are associated with.

The rounds activity window 44 presents information that is similar to that of the inpatients activity window 36, including each patient's full name 142, an identifier 144 of a physician currently attending the patient, and a current location 146 of the patient. The rounds activity window 44 also functions similarly to the inpatients activity window 36. The program automatically adds patients to the rounds activity window 44, for example, when the patients are assigned to a team. A difference between the rounds activity window 44 and the inpatients activity window 36 is that team members add patients to the rounds activity window 44, and the patients are only removed if a team member removes them or the patient is discharged from the hospital. Furthermore, if an inpatient is transferred to another hospital service or attending physician, his or her information will be removed from the inpatients activity window 36 but will remain in the rounds activity window 44 until a team member removes the information or the patient is discharged from the hospital.

A rounds context menu 148 associated with the rounds activity window 44 is illustrated in FIG. 4. The rounds context menu 148 is similar in form and function to the inpatients context menu 66 described above. Patient overview 150 and current clinical data 152 menu items of the rounds context menu 148 function substantially identically to corresponding inpatient context menu items described above in relation to the inpatients context menu 66, and therefore will not be described in detail here.

An add inpatient to rounds menu item 154 enables the user to add a patient to the rounds of a particular team. To add a patient to the rounds activity window 44, the user must be a member of the team to which the patient will be added, and must also be a system administrator, administrator, doctor, or advanced practice nurse (APN). When an authorized user selects the add inpatient to rounds menu item 154, the program presents a form for assisting the user in adding an inpatient to the rounds activity window 44. An exemplary form 156 is illustrated in FIG. 6, wherein the form 156 lists all of the current inpatients, as indicated by the HIS, and includes an add patient button 158 and a cancel button 160. The user adds an inpatient to the rounds activity window 44 by selecting a patient from the list of patients presented in the form 156 and then selecting the add patient button 158. The user may cancel the transaction without adding a new patient to the rounds activity window 44 by selecting the cancel button 160.

The remove inpatient from rounds menu item 162 enables the user to remove a patient from the rounds of a particular team. To remove a patient from the rounds activity window 44, the user must be a member of the team from which the patient will be removed, and must also be a system administrator, administrator, doctor, or advanced practice nurse (APN). The remove inpatient from rounds menu item 162 is a patient-specific menu item, therefore the user must select a specific patient from the rounds activity window 44 prior to activating the rounds context menu 148 and selecting this context menu item.

Figure 7:
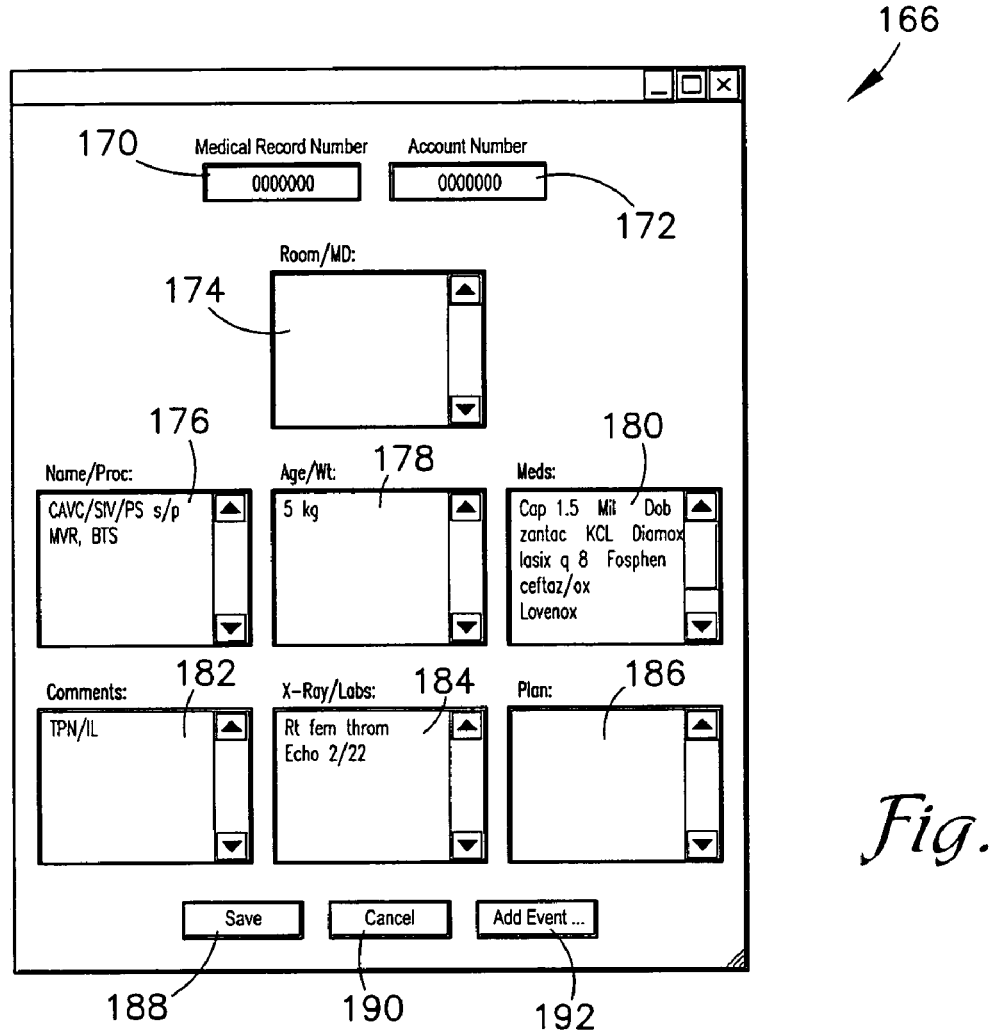
FIG. 7 is an add notes form presented when the user selects an add/edit round notes menu item of the context menu associated with the rounds activity window.

The add/edit round notes menu item 164 enables the user to add or edit notes pertaining to a particular patient. To select this menu item the user must be a system administrator or an APN. The add/edit round notes menu item 164 is a patient-specific menu item, therefore the user must select a specific patient from the rounds activity window 44 prior to activating the rounds context menu 148 and selecting this context menu item. When this menu item is selected, the program presents a rounds notes form 166 as illustrated in FIG. 7. The rounds notes form 166 enables the user to submit notes pertaining to the selected patient, which notes will be available in a rounds report 168, illustrated in FIG. 9 and described in more detail below.

The rounds notes form 166 includes various data entry elements for receiving information from the user. The illustrated form 166 includes text boxes for receiving a medical record number 170, account number 172, room and doctor 174, patient name and procedure 176, patient age and weight 178, medications 180, comments 182, X-ray and lab information 184, and plan information 186. Each text entry box represents one column of the rounds report 168, and the data entered in each column will appear in the proper column of the rounds report 168 pertaining to the selected patient.

The rounds notes form 166 also includes a save button 188, a cancel button 190, and an add event button 192. Selecting the save button 188 stores the data entered in the text boxes and closes the form 166. Selecting the cancel button 190 closes the form 166 without saving any data. Selecting the add event button 192 opens an event form (described below) so that the user can enter a special event associated with this patient.

Figure 8:
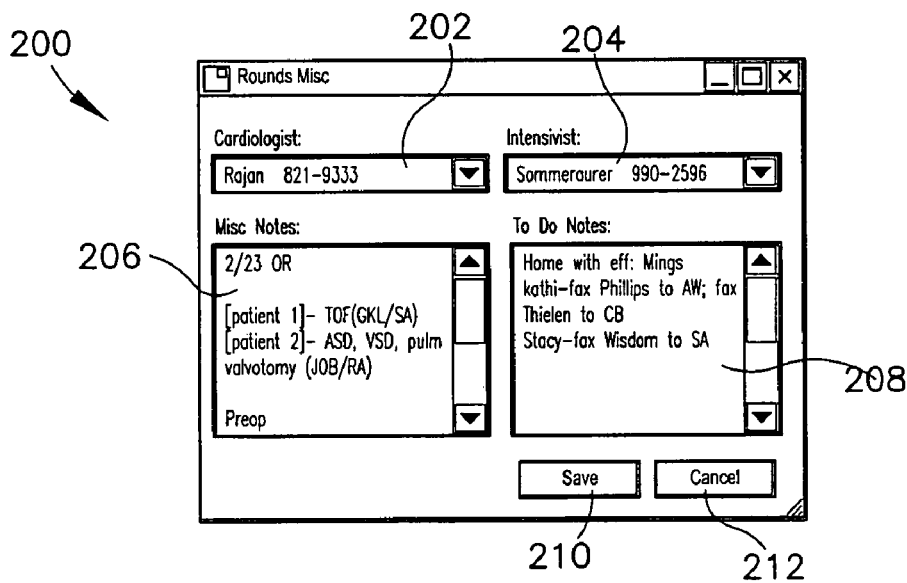
FIG. 8 is an add rounds miscellaneous form presented when the user selects an add/edit round miscellaneous menu item of the context menu associated with the rounds activity window.

The add/edit round miscellaneous menu item 194 of the rounds context menu 148 is a non-patient specific menu item that enables the user to submit information that will appear in a top section 196 or a bottom section 198 of the rounds report 168. Only users with designated roles can select this menu item, such as users with the role of system administrator and APN. Selecting the add/edit rounds miscellaneous menu item 194 causes the program to present the add/edit rounds miscellaneous form 200 illustrated in FIG. 8. The user selects an on-service cardiologist from a cardiologist drop down menu 202, and the name and phone number of the on-service cardiologist is placed in the top section 196 of the rounds report 168. The user selects an on-service intensivist from an intensivist drop down menu 204, and the name and phone number of the on-service intensivist is also placed in the top section 196 of the rounds report 168.

The user may submit information in a miscellaneous notes section 206 and a to do notes section 208, which information is placed in the bottom section 198 of the rounds report 168. If the user selects a save button 210, the program stores the data in the form 200 and closes the form 200. If the user selects a cancel button 212, the program closes the form 200 without storing any data.

The create rounds report menu item 214 of the rounds context menu 148 is a non-patient specific menu item that enables the user to quickly view information about each patient listed in the rounds activity window 44. When the user selects the create rounds report menu item 214, the program gathers information about each patient listed in the rounds activity window 44 and presents the information in the rounds report 168 illustrated in FIG. 9. The rounds report 168 can then be printed and used by, for example, doctors or nurses who are performing rounds on the patients. The rounds report 168 is a conventional report including information readily understood by those skilled in the art, and therefore will be described herein in greater detail.

The filter rounds by menu item 216 is similar to the filter inpatients by menu item 76 of the inpatient context menu 66, described above. Selecting the filter rounds by menu item 216 of the rounds context menu 148 enables the user to determine how the patients listed in the rounds activity window 44 are filtered, or presented. The user may designate, for example, filter parameters such as one or more services, teams, or attending physicians to use in selecting patients to include in the rounds activity window 44.

The Consults Activity Window

The consults activity window 46 presents information about patients who are associated with a physician or a team of physicians in a consultation relationship. As illustrated in FIG. 4, a title bar 218 of the consults activity window 46 displays which team or physician the listed patients are associated with.

The consults activity window 46 presents information that is similar to that of the inpatients activity window 36, including each patient's full name 220, a physician identifier 222 of a physician currently attending the patient, and a current location 224 of the patient. The consults activity window 46 also functions similarly to the inpatients activity window 36. A difference between the consults activity window 46 and the inpatients activity window 36 is that team members and physicians add patients to the consults activity window 46, and the patients are only removed if a team member or physician removes them or the patient is discharged from the hospital. Furthermore, if an inpatient is transferred to another hospital service or attending physician, the program removes his or her information from the inpatients activity window 36 but does not remove the information from the consults activity window 46 until a team member specifically requests removal of the information or the patient is discharged from the hospital.

A consults context menu 226 associated with the consults activity window 46 is also illustrated in FIG. 4. The consults context menu 226 is similar in form and function to the inpatients context menu 66 described above. Patient overview 228 and current clinical data 230 menu items of the rounds context menu 226 function substantially identically to corresponding inpatient context menu items described above in relation to the inpatients context menu 66.

An add inpatient to consults menu item 232 enables the user to add a patient to the consults of a particular team. To add a patient to the consults activity window 46, the user must be a member of the team to which the patient will be added or a physician, and must also be a system administrator, administrator, doctor, advanced practice nurse (APN), or perfusionist. When an authorized user selects the add inpatient to consults menu item 232, the program presents a form for assisting the user in adding an inpatient to the consults activity window 46. An exemplary form 156 is illustrated in FIG. 6 and described above.

A remove inpatient from consults menu item 234 enables the user to remove a patient from the consults activity window 46. To remove a patient from the consults activity window 46, the user must be a member of a team if the patient will be removed from that team, and must also be a system administrator, administrator, doctor, APN, or perfusionist. If a patient is included in the consults of an individual physician, only that physician can remove the patient from his or her consults list. The remove inpatient from rounds menu item 234 is a patient-specific menu item, therefore the user must select a specific patient from the consults activity window 46 prior to activating the consults context menu 226 and selecting this context menu item.

The filter consults by 236 menu item is similar to the filter inpatients by menu item 76 of the inpatient context menu 66, described above. Selecting the filter consults by menu item 236 of the consults context menu 226 enables the user to determine how the patients listed in the consults activity window 46 are filtered, or presented. The user may designate, for example, filter parameters such as one or more services, teams, or attending physicians to use in selecting patients to include in the consults activity window 46.

The Cath Conference and Personal Notes Activity Windows

The cath conference activity window 48 contains a list of all patients that are scheduled to be presented to or have been presented to the catheterization conference on date indicated by the second date selector 54. The personal notes activity window 50 contains notes that can be written and responded to by user, attending physician, team, or department.

The Filter Function

Figure 10:
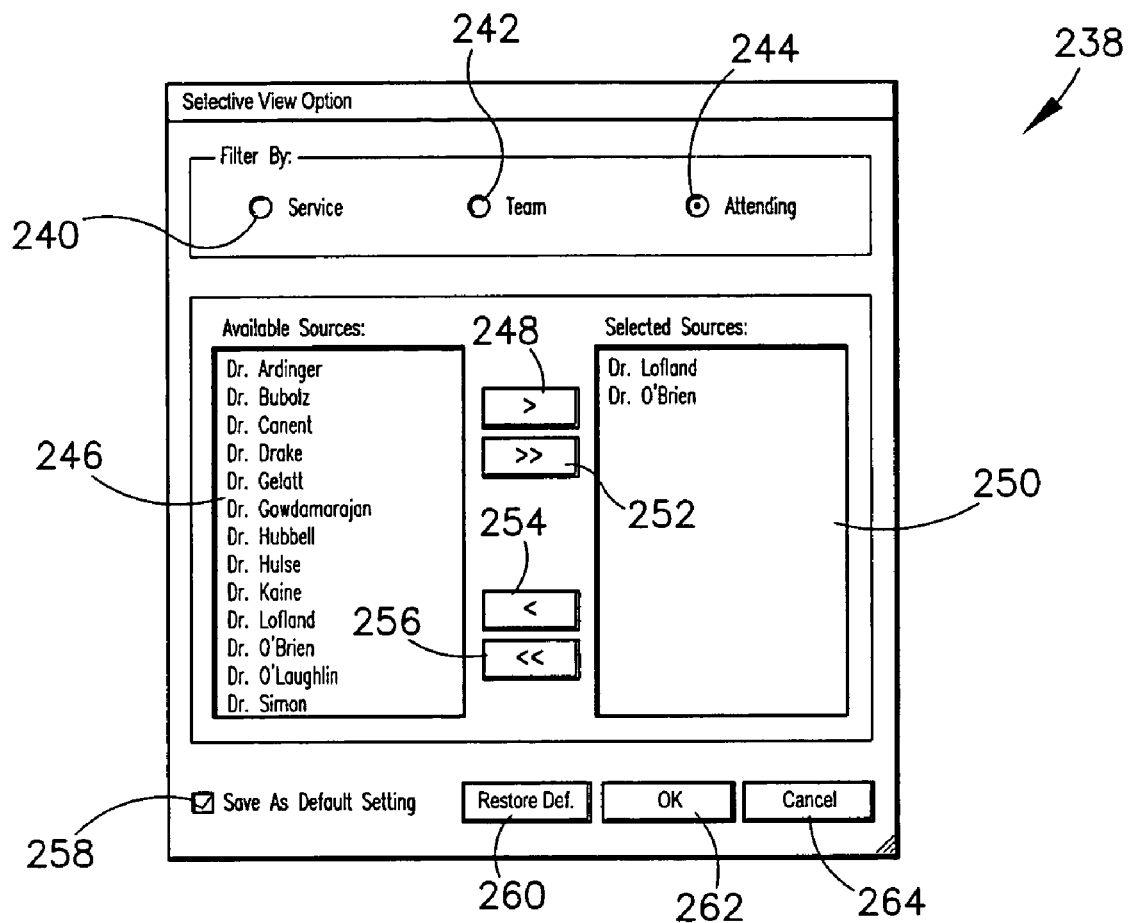
FIG. 10 is a filter by form presented when the user selects a filter by menu item from any of the activity windows of the interface of FIG. 3.

When the user selects a "filter by" context menu item from any of the context menus described above, the program presents a filter by form 238 illustrated in FIG. 10. A "filter by" set of radio buttons includes a service button 240, team button 242, and attending physician button 244. If the user selects the service radio button 240, for example, the program presents patients that are scheduled to receive, or have received, a particular service. An available sources window 246 presents the available filter parameters for each filter option. As illustrated, for example, if the attending physician radio button 244 is selected, the available sources window 246 presents all possible attending physicians for the user to choose from. A single add button 248 enables the user to add the selected physician to a selected sources window 250, and an add all button 252 enables the user to add all sources to the selected sources window 250. A single remove button 254 and a remove all button 256 similarly function to move sources from the selected sources window 250 to the available sources window 246.

A save as default setting checkbox 258 enables the user to save the current settings as default settings, and a restore default button 260 enables the user to abandon any current settings and revert to the previously-saved default settings. Selecting an ok button 262 stores and applies the current settings and closes the window, and selecting a cancel button 264 closes the window without storing or applying any settings.

The Patient View

Figure 11:
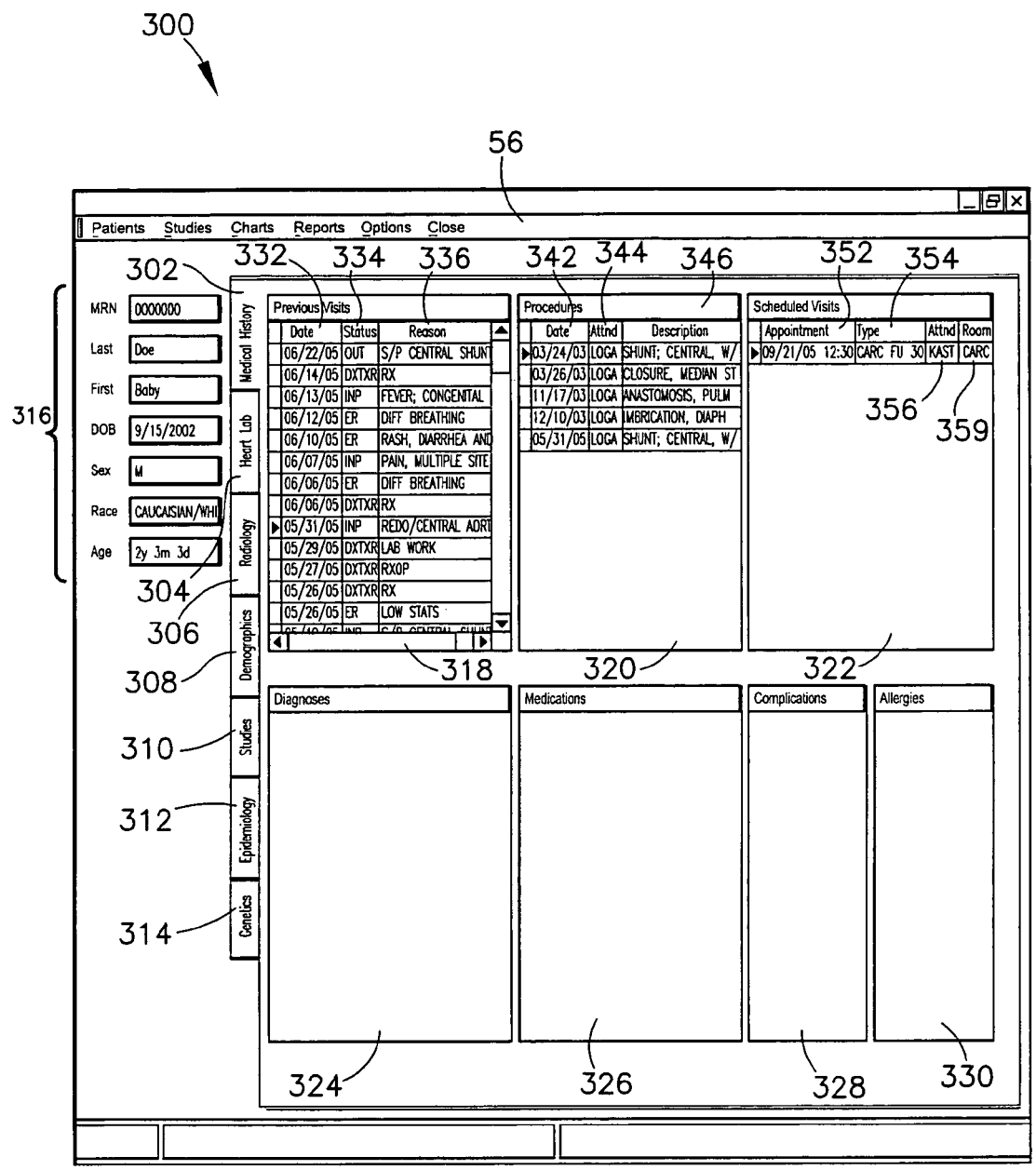
FIG. 11 is a top-level user interface associated with a patient view of the present invention and illustrating a medical history tab of the interface.

Referring to FIG. 11, the patient view presents a top-level interface 300 that enables physicians, nurses, clinical care givers or other users to view detailed information associated with a particular patient. The illustrated patient view interface 300 includes various information tabs, wherein each tab relates to a separate interface element. In the illustrated interface 300, selecting a tab presents an interface element with various information windows. The tabs include medical history 302, heart lab 304, radiology 306, demographics 308, studies 310, epidemiology 312, and genetics 314. The interface 300 also presents a plurality of patient identifier fields 316 that provide identification information about the current patient.

The menu toolbar 56 is located near a top of the interface 300 and enables the user to select items and options that apply universally and are not associated with a specific tab or information window. The interface 300 also provides context menus that enable the user to select items and options that are associated with a specific information window, and enable the user to drill down to view more detailed information about a selected piece of information that is presented in an information window. As explained above in relation to the department view interface 34, a context menu associated with each information window is activated when the user positions an on-screen pointer or arrow over the specific activity window and selects a designated input button, such as the right mouse button.

The patient identifier fields 316 remain at the illustrated location to the left of the patient tabs regardless of which patient identifier tab the user is viewing. The patient identifier fields 316 include the patient's medical record number (MRN); the patient's last name; the patient's first name; the patient's date of birth; the patient's gender; the ethnic origin of the patient; and the age of the patient in years, months and days. The MRN is a unique patient identifier number assigned by the hospital to each patient on record. All of a patient's medical records are referenced by this unique number each time the patient visits the hospital.

The Medical History Tab

The medical history tab 302 presents information relating to various aspects of the patient's medical history. The illustrated medical history tab 302 presents seven information windows, including previous visits 318, procedures 320, scheduled visits 322, diagnoses 324, medications 326, complications 328, and allergies 330 information windows.

The previous visits information window 318 presents a list and brief description of all prior activity that the selected patient has had with the hospital. The illustrated previous visits information window 318 includes one row of information for each visit or activity, wherein the rows are divided into columns corresponding to a date of the visit 332; status 334, or type of visit; and reason 336 for the visit. An exemplary list of types of visits that may be included in the status column 334 includes inpatient (INP), outpatient (OUT), emergency room (ER), and diagnostic transfer activities (DXTXR).

Figure 12:
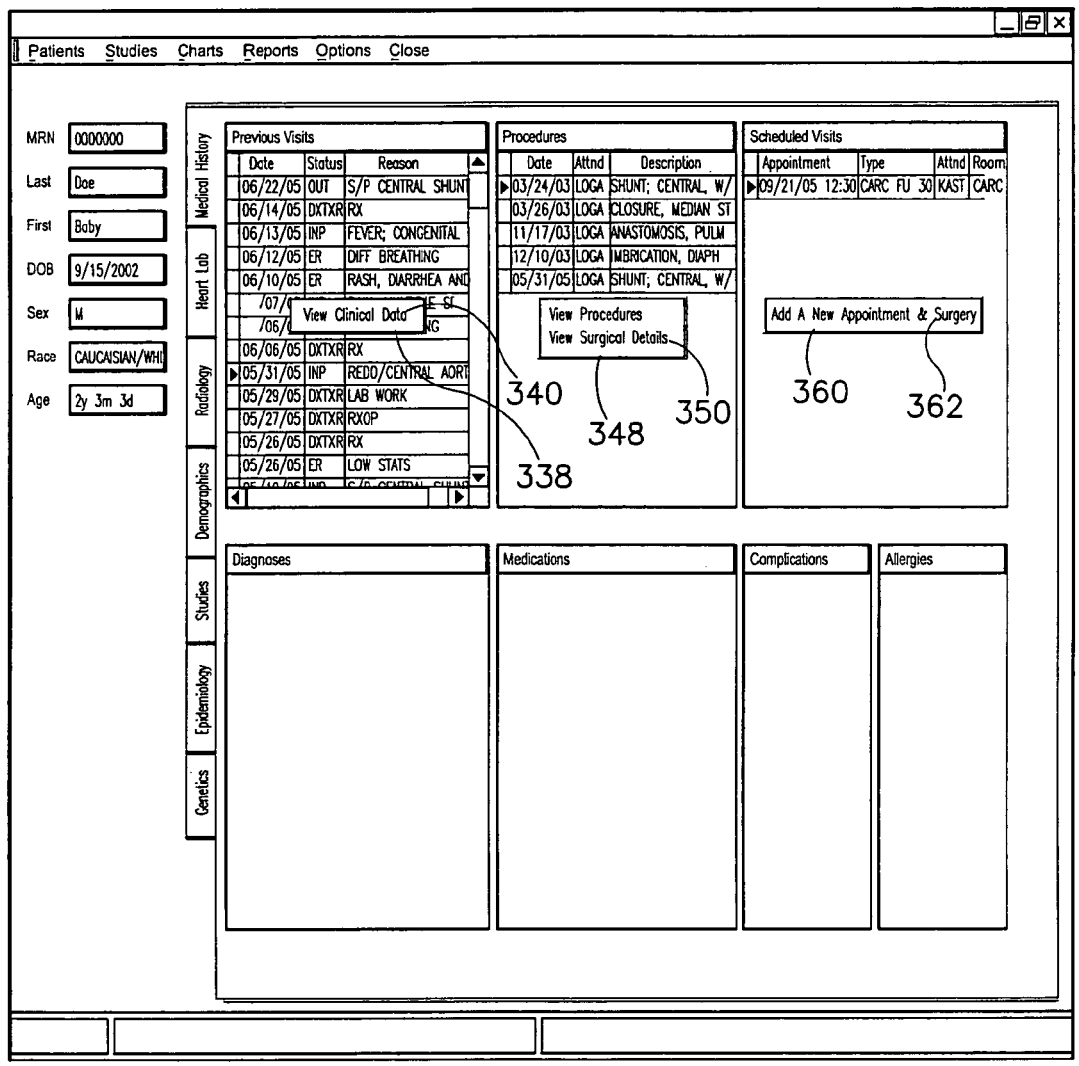
FIG. 12 is the user interface of FIG. 11 illustrated with context menus that are associated with various information windows of the user interface.

A previous visits context menu 338 is illustrated in FIG. 12, which includes only a single menu item 340 labeled "view visit details." The view visit details context menu item 340 is specific to an activity or visit, therefore the user must select a visit or activity prior to activating the context menu 338 and selecting this menu item. The visit or activity is selected by using a pointing device to select a small box to left of the visit or activity, as explained above in relation to the department view user interface 34. When the user selects the view visit details menu item 340 the program automatically opens the visit view for the selected patient. Any clinical information associated with this visit will be displayed in the visit view. The visit view is described in greater detail below.

The procedures information window 320 presents a list and brief description of all prior procedures that the patient has had at the hospital. There is one row of data in this window for each separate procedure that the patient has had, even if there are multiple procedures during one patient visit. The rows are divided into columns corresponding to date of the procedure 342; attending surgeon 344; and procedure 346, which indicates the primary procedure associated with this surgery. A procedures information window context menu 348 is illustrated in FIG. 12, wherein the menu 348 presents a single item 350 labeled "view surgical data." When the user selects the view surgical data 350 menu item the program launches the operative tab of the visit view associated with the selected procedure. As explained below, the operative tab presents information associated with the procedure.

Figure 13:
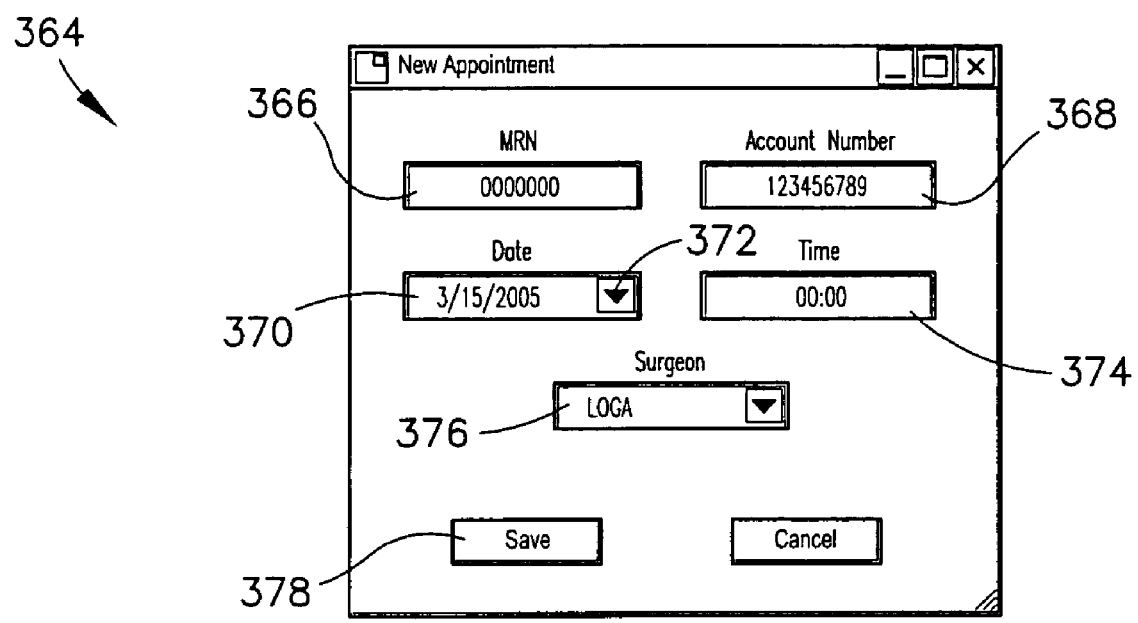
FIG. 13 is a new-appointment form presented by the computer when the user selects an "add new appointment and surgery" menu item from a context menu associated with a scheduled visits information window of the interface of FIG. 3.

The scheduled visits information window 322 presents a list of future visits that are scheduled for the patient. There is one row of data in this window for each scheduled visit, wherein the rows are divided into columns representing appointment 352, which is the date and time of the scheduled visit; type of visit 354; attending physician 356, which includes an attending physician identifier who the visit is scheduled with; and room 358 where the visit is scheduled. A scheduled visits information window context menu 360 includes a single item 362 labeled "add a new appointment and surgery." When the user selects the add a new appointment and surgery menu item 362, the program presents a new appointment form 364 illustrated in FIG. 13.

The new appointment form 364 presents various data fields through which the user submits information relating to a new appointment or new surgery. An MRN data field 366 contains the medical record number of the patient associated with the appointment. An account number data field 368 receives an account number associated with the visit, and a date of the appointment or surgery data field 370 receives the scheduled date. The date presented in the date field 370 is the present date by default, and the user may select another date using a drop-down menu activator 372. A time data field 374 receives the time of the appointment, and a surgeon data field 376 enables the user to choose a surgeon performing the procedure.

When the user selects a save button 378, the program schedules the appointment or surgery by saving the information to the database 20e and creates an empty surgery record to be completed at a later time. A confirmation message is then presented to the user, and the appointment immediately appears in the scheduled visits information window 322. The scheduled appointment is also accessible via other views and/or interfaces. For example, when the surgeon logs into the program and launches the department view (described above), the scheduled appointment will appear in the procedures activity window 38 when the surgeon selects the date of the scheduled appointment from the first date selector 52.

The diagnoses information window 324 presents a list of all previous diagnoses for the patient. The medications information window 326 presents a list of all medications that the patient is currently taking. The complications information window 328 presents a list of all previous or current complications associated with the patient. The allergies information window 330 presents a list of all known allergies associated with the patient. Thus, using the various information windows of the medical history tab 302, the user can quickly and easily view patient medical information that is pertinent to diagnosing illnesses, prescribing medications, and so forth.

The Heart Lab Tab

Figure 14:
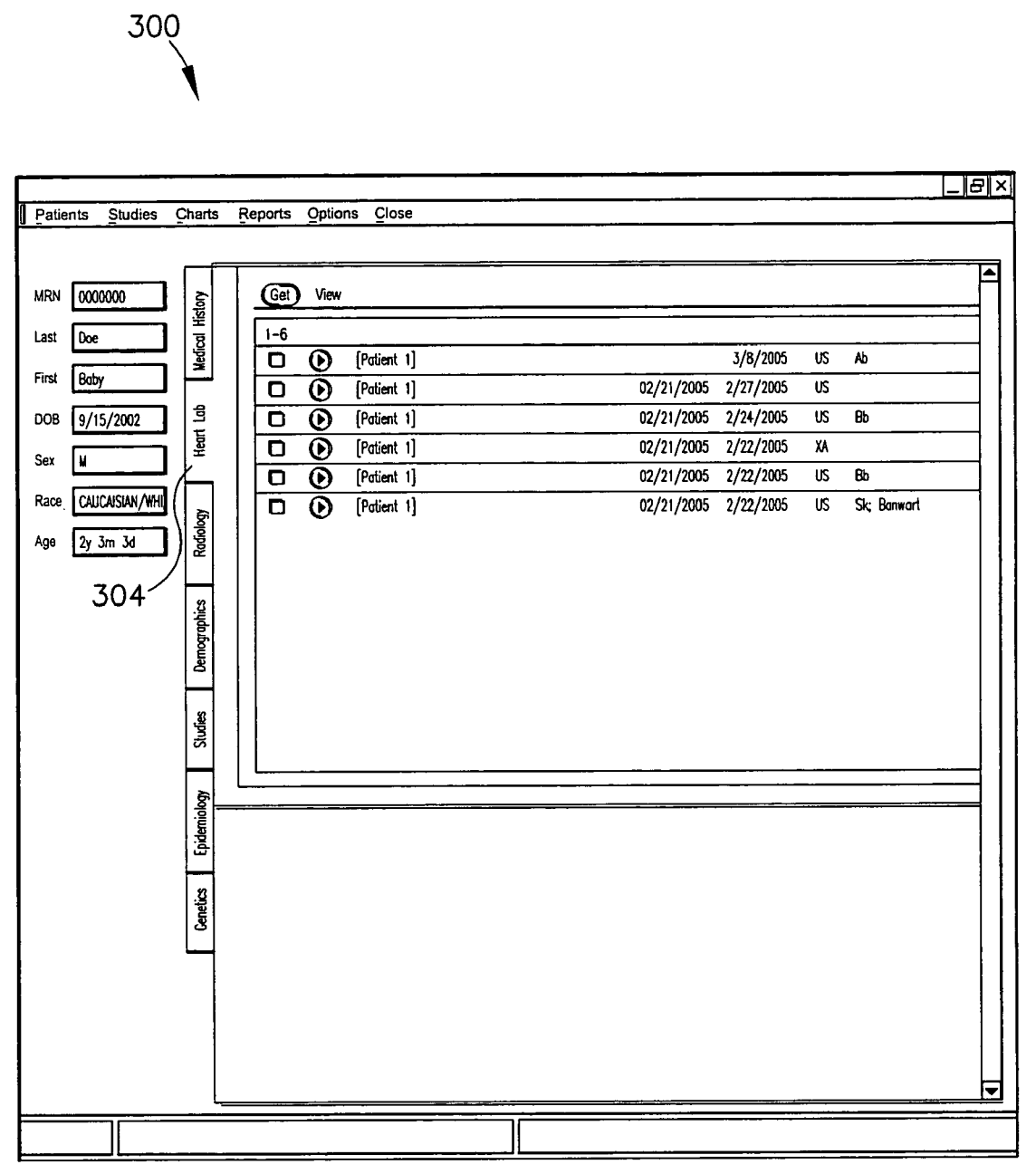

The heart lab tab 304 is illustrated in FIG. 14 and enables the user to view medical images associated with the patient. When the heart lab tab 304 is selected, the program automatically requests updated images from another hospital department. In one embodiment, the program automatically communicates with the hospital cardiology imaging system 20c to acquire any catheterization or echo image studies that have been performed on the patient. The cardiology imaging system 20c provides a list of all stored imaging studies for the patient, as illustrated in the interface window of FIG. 14.

The interface between the computer 10 implementing the present invention and the cardiology imaging system 20c may include a web client window and an active-x control located in an imaging tab frame. When the heart lab tab 304 is selected, the program sends a username, password, and medical record number to the web-based cardiology imaging system 20c. The cardiology imaging system responds by opening a web session to the program and displaying all of the studies for the selected medical record number. The imaging system web session is then displayed in a web client of the heart lab tab 304. The user then has all the functionality of the cardiology imaging system in the web client window of the heart lab tab 304.

Figure 15:
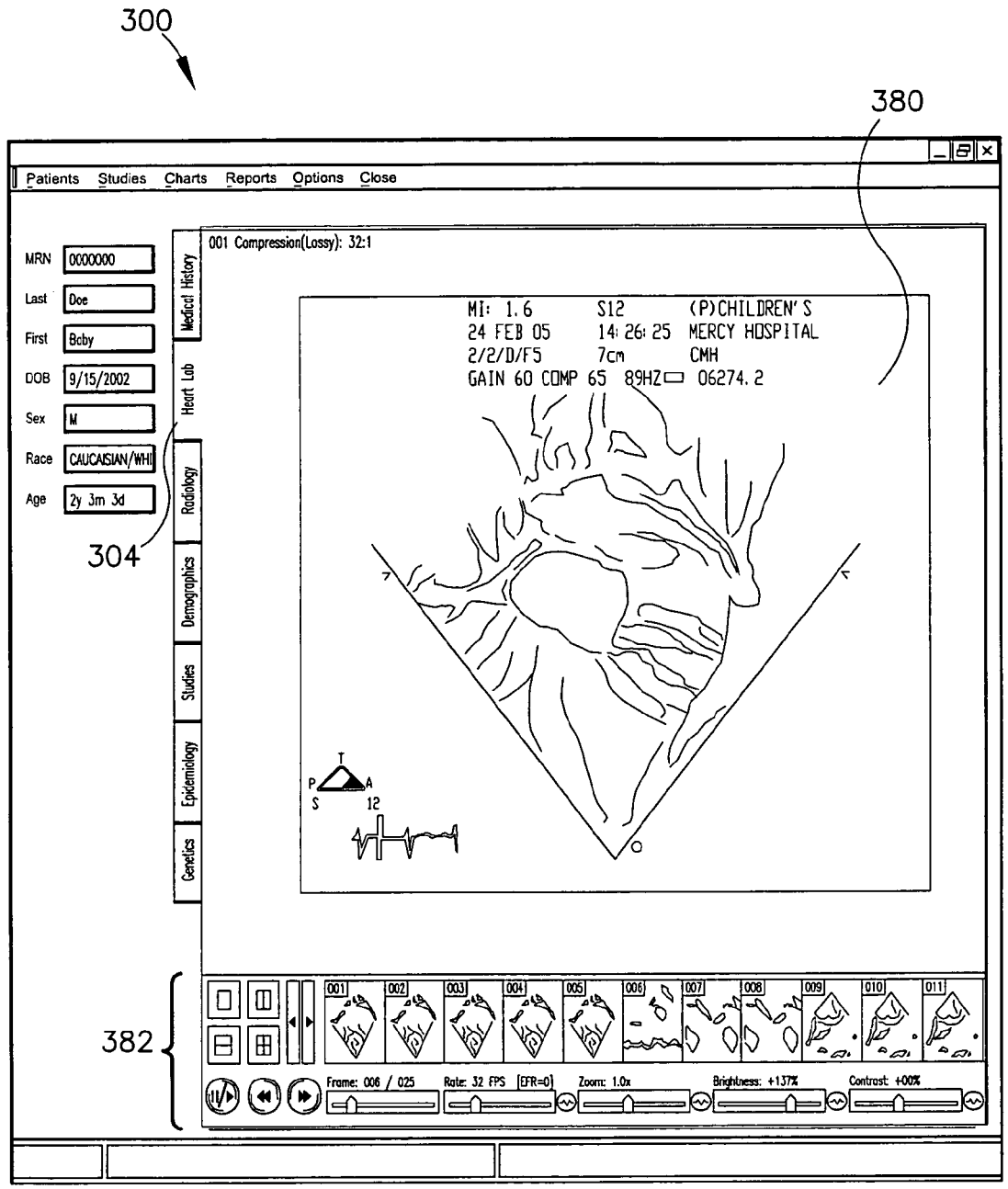
FIG. 15 is an echocardiogram web interface presented as part of the heart lab tab of FIG. 14.

An exemplary echocardiogram 380 communicated to and presented by the heart lab tab 304 is illustrated in FIG. 15. A control box 382 created by the echocardiogram software presents a series of controls that enable the user to choose between several images and manipulate the image 380 currently displayed. These controls will be readily recognized by those skilled in the art and therefore will not be described in detail here.

The Radiology Tab

The radiology tab 306 is illustrated in FIG. 16. The radiology tab 306 is similar to the heart lab tab 304 in that it enables the user to view medical images associated with the patient. When the user selects the radiology tab 306, the program automatically requests updated images from the hospital radiology imaging system 20b to acquire any film, echo, CT, or other image studies that have been performed on the patient. The radiology imaging system 20b will respond back with a list of all stored radiology studies for that patient, as shown in FIG. 16.

Figure 17:
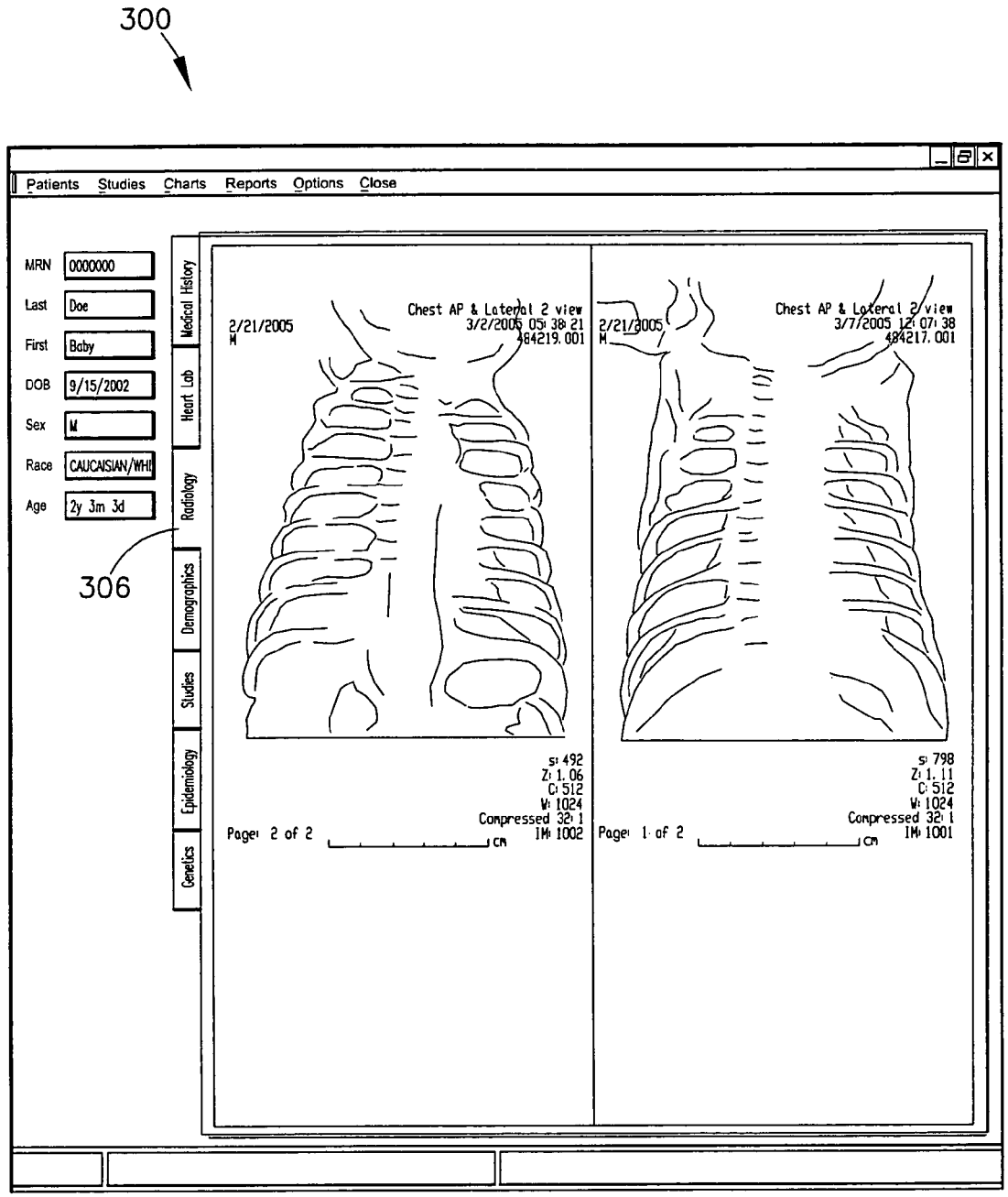
FIG. 17 is an exemplary radiology web interface presented as part of the radiology tab of FIG. 16.

The interface between the program and the radiology imaging system 20b is a web client window and an active-x control located in a radiology tab frame. When the radiology tab 306 is selected, the program sends a username, password, and medical record number to the web-based radiology imaging system. The radiology imaging system 20b responds by opening a web session to the program and displaying all studies for the selected medical record number. The radiology imaging system web session is then displayed in the web client of the radiology tab 306. The user then has all the functionality of the radiology web-based imaging system in the web client window of the radiology tab 306. An exemplary radiology web session is illustrated in FIG. 17, wherein two images are presented concurrently.

The Demographics Tab

Figure 18:
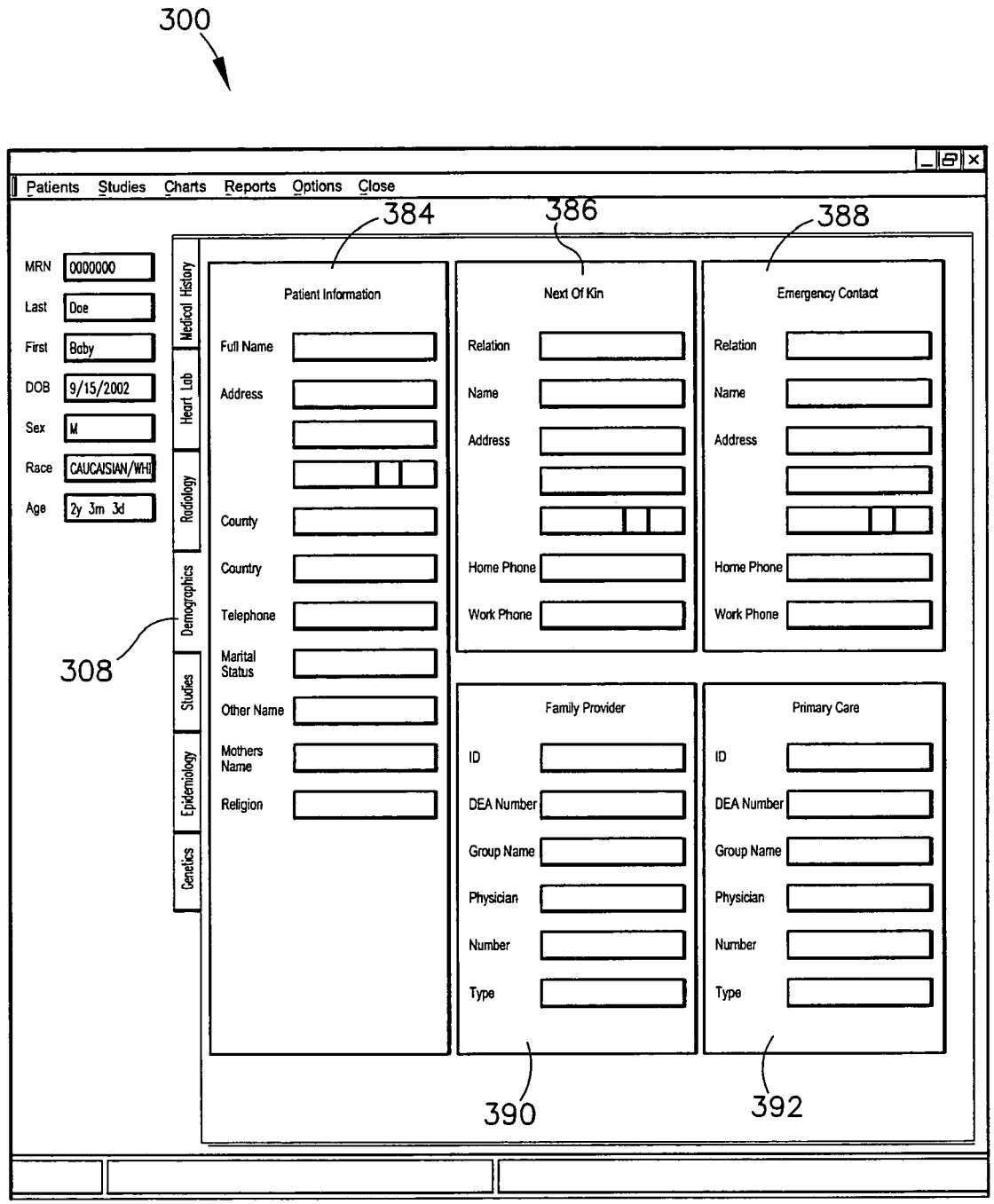
FIG. 18 is an exemplary demographics tab of the user interface of FIG. 11.

The demographics tab 308 is illustrated in FIG. 18 and presents general, family, and provider information associated with the patient. The demographic information is presented in various user interface sections relating to patient information 384, next of kin information 386, emergency contact information 388, family provider information 390, and primary care physician information 392. The program automatically retrieves the information in each of these sections from the HIS 20a when a patient is submitted to the program. The program also automatically updates the demographic information with any changes made to the HIS 20a at pre-determined times, such as on the day before a scheduled appointment and on the day after a scheduled appointment.

The Studies Tab

Figure 19:
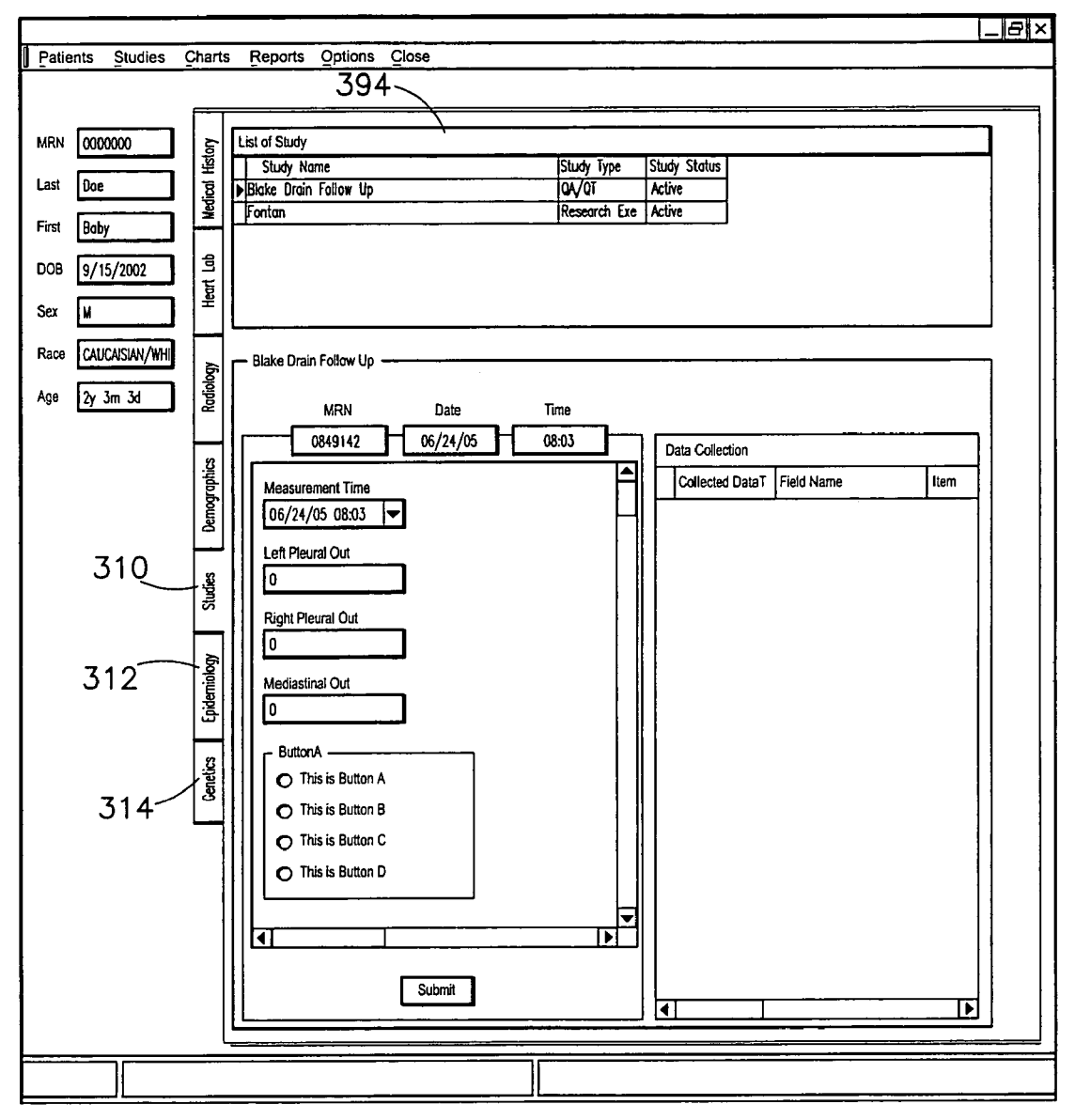

The studies tab 310, illustrated in FIG. 19, presents information about studies the patient is currently enrolled in. The tab 310 allows the user to view, submit, and modify study when the user selects that study from a list 394 of studies.

The Epidemiology and Genetics Tabs

The epidemiology tab 312 and the genetics tab 314 present epidemiological information and genetic information, respectively, pertaining to the selected patient. This information may be presented in much the same form as the medical history and demographics information discussed above.

The Visit View

Referring to FIG. 20, the visit view presents a top-level interface 400 that enables physicians, nurses, clinical caregivers and other users to view detailed information associated with a hospital visit of a particular patient. The illustrated visit view interface 400 includes various information tabs, wherein each tab relates to a particular type of information. In the illustrated interface 400, selecting a tab presents an interface element with various information windows. The illustrated tabs include diagnoses 402, heart lab 404, radiology 406, pre-operative 408, operative 410, post-operative 412, reports 414, discharge 416, and follow up 418. The top-level interface 400 also presents a plurality of patient identifier fields 420 that provide identification information about the current patient. The patient identifier fields 420 are substantially identical to the patient identifier fields 316 that are presented as part of the patient view, described above.

The Diagnoses Tab

The diagnoses tab 402 presents information about one or more diagnoses of a patient during a visit.

The Heart Lab and Radiology Tabs

The heart lab tab 404 and the radiology tab 406 are substantially identical to the heart lab tab 304 and the radiology tab 306 presented as part of the patient view, described above. Therefore, these tabs will not be described in detail here.

The Pre-Operative Tab

The pre-operative tab 408 includes pre-operative medical information for the selected patient. The pre-operative tab 408 includes a pre-op review section and a details section. The pre-op review section includes the complete pre-operative data sheet for the selected patient, while the details section includes more detailed pre-operative data.

The Operative Tab

The operative tab 410 is illustrated in FIG. 20 and presents information relating to surgeries performed during the selected patient's visit. The surgical information is divided into several tabs nested within the operative tab 410, wherein the nested tabs are located along a top of the operative tab and include a general information tab 422, a surgical details tab 424, a valves and homografts tab 426, a perfusion tab 428, and an anesthesiology tab 430.

The general information tab 422 presents a list of surgeries in a top portion 432 of the tab 422, wherein the list includes various pieces of information associated with each surgery. The illustrated list of surgeries includes a date 434 of the surgery, attending physician 436, surgery type 438, current procedure terminology (CPT) 440, and a description 442 of the primary procedure for each surgery. When a particular surgery is highlighted, such as when the user selects the surgery with an input device, various data fields in a lower section 444 of the tab 422 are updated to reflect the selected surgery.

The data fields of the lower section 444 of the general information tab 422 include MRN 446, account number 448, and date 450 the patient was admitted for the surgery. A surgery data section 452, surgical consultation data section 454, and pre-op testing data section 456 each include date, time and location fields. An attending physician data field 458 indicates the patient's attending physician, and a surgery type data field 460 indicates the type of surgery that was performed on the patient. A cardiologist data field 462 indicates the patient's cardiologist, and a procedure sequence data field 464 indicates a sequence associated with the procedure, such as initial, staged, repeat, chest closure, and so forth. Patient age 466, weight 468, and height 470 data fields present the indicated patient information. A prior total CV surgeries data field 472 indicates the total number of cardiovascular surgeries this patient has had, while a prior open CV surgeries data field 474 indicates the number of open cardiovascular surgeries this patient has had.

A patient origin data field 476 indicates where the patient went to surgery from, such as pediatric intensive care unit, same day surgery (SDS), hospital bed, and so forth. A scheduling status data field 478 indicates how the surgery was scheduled, such as elective, urgent, emergent, and so forth. A body surface area data field 478 provides a calculation of the patient's body surface area based on the patient's height and weight. An initial indications data field 480 lists pre-operative patient diagnoses. An antenatal diagnosis checkbox 482 indicates whether the procedure related to fetal diagnosis, and a TEE required checkbox 484 indicates whether a transesophogeal echo was required.

Figure 21:
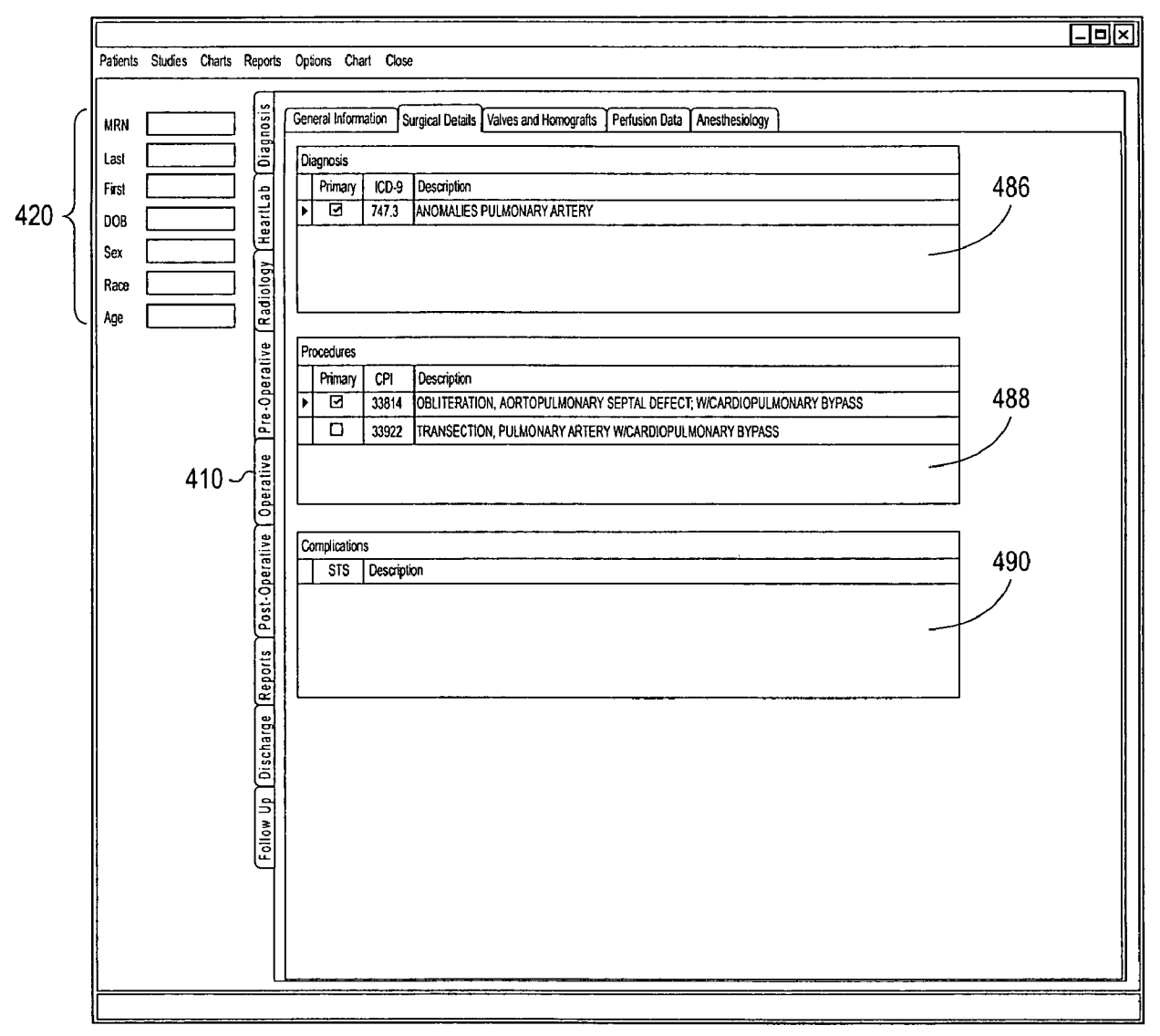

The surgical details tab 424 presents information relating to the diagnoses, procedures, and complications associated with the surgery that is selected from the general information tab 422. As illustrated in FIG. 21, the surgical details tab 424 is divided into three sections. A first section 486 is dedicated to diagnoses, a second section 488 is dedicated to procedures, and a third section 490 is dedicated to complications. Each section contains a context menu item which allows the user to enter primary and secondary surgical diagnoses, procedures, and complications.

The valves and homografts tab 426 presents information related to any valves, homografts, or both used during the surgery that is selected from the general information tab 422. The perfusion data tab 428 presents perfusion data collected during the surgery that is selected from the general information tab 422. The anesthesiology tab 430 presents anesthesiology information collected during the surgery that is selected from the general information tab 422.

The Post-Operative Tab

Figure 22:
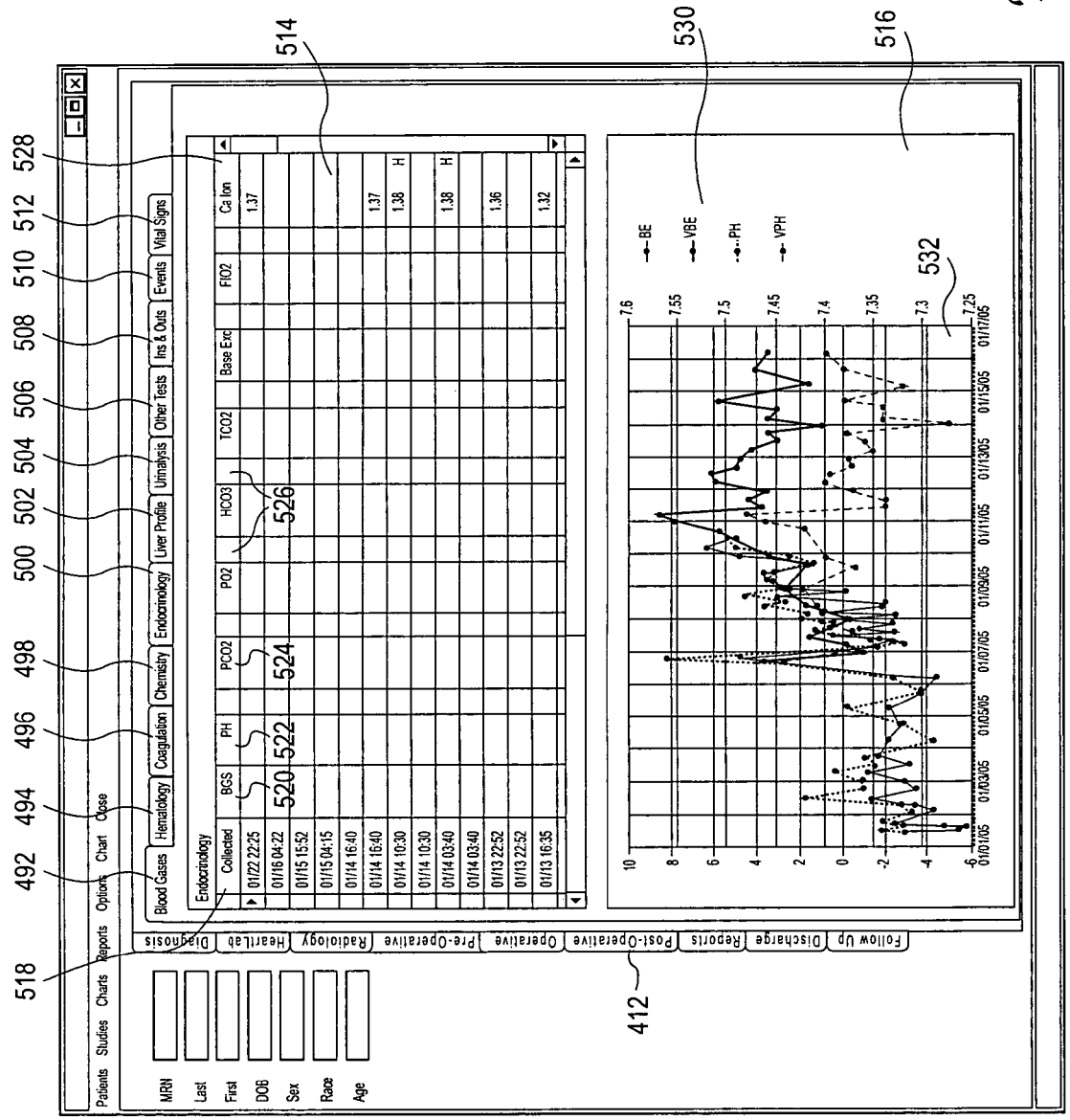
FIG. 22 is the interface of FIG. 20 illustrating a blood gases element of a post-operative tab of the interface.

The post-operative tab 412 is illustrated in FIG. 22 and presents information relating to the patient's status after the surgery. The post-operative tab 412 includes a series of nested tabs arranged horizontally near a top of the tab 412. The nested tabs include blood gases 492, hematology 494, coagulation 496, chemistry 498, endocrinology 450, liver profile 452, urinalysis 454, other tests 456, ins and outs 458, events 460, and vital signs 462.

The blood gases tab 491 presents laboratory information pertaining to the patient's blood gases. The blood gases tab 492 is divided into two areas: a top area presents a blood gases lab result table 514, and a bottom area presents a blood gases chart 516.

The blood gases result table 514 lists all of the blood gas laboratory results for the selected patient over a predetermined period of time. The length, beginning date, and ending date of the predetermined period of time depends on how the visit view was invoked. If the user invoked the visit view by selecting a current clinical data context menu item from the department view, for example, the predetermined period of time is the user-defined "lookback" period that ends with today's date and begins a user-determined number of days prior to today's date. Alternatively, if the user invoked the visit view by selecting a previous visit from the patient view and then selected the view clinical data menu item 340, the predetermined period of time corresponds to that visit so that the information includes all of the lab results collected during the visit.

The blood gases lab result table 514 lists all lab results in reverse chronological order, so that the most recent lab result is always at the top of the list. Each blood gas result occupies a separate row of the table, and each row is divided into columns. A first column 518 of each row, denoted "collected," specifies the date and time that the sample was collected from the patient. Subsequent columns present specific lab results, such as BGS 520, PH 522, PCO2 524, and so forth. The lab results can include numeric or textual information. To the right of some of the lab result columns is an unmarked status column 526 for displaying an indication from the laboratory of the status of the result in the corresponding results column. If a particular lab result is within a normal range, the corresponding status column is left unmarked. Alternatively, the status column may be marked CL, L, H, or CH to indicate that the lab result is critically low, low, high, or critically high, respectively.

An exemplary use of the status column is illustrated in connection with a calcium ion lab results column 528. In the illustration, the result of a first blood test performed on January 14 was 1.38, the result of a second blood test performed on January 14 was 1.38, and the result of a third blood test performed on January 14 was 1.37. Because the 1.37 result is within the normal range, the status column box corresponding to the first test remains unmarked. Furthermore, the 1.38 results are high, therefore the status column boxes corresponding to the second and third results are each marked "H," indicating that the result is high. A user can thus quickly and easily determine which results are normal and which results present potential challenges. An exemplary list of blood gases that are tested is illustrated in the table of FIG. 23.

The blood gas chart 516 is presented in the blood gases tab 492 concurrently with the blood gases lab result table 514. The chart 516 presents graphical information associated with the lab results from multiple tests plotted over time. The illustrated chart 516 plots the values of four blood gas tests across multiple test dates beginning on Jan. 1, 2005 and ending on Jan. 17, 2005. As illustrated in a key 530 to the right of a graph 532 of the chart 516, the chart 516 plots the values of base excess (BE), venous base excess (VBE), PH, and venous PH. Each of the plots is placed on the same graph 532, therefore each is presented in a different color. The key 530 indicates which color each graph is plotted in by illustrating the line next to each label in the corresponding color.

The chart 516 is built by first going through every value in each laboratory test result set and converting it to a numeric value. If a particular data point value cannot be converted to a numeric value, it is removed from the dataset of that lab result series. During this process, the earliest and latest collection times of all four series are also determined. These two times form the range of the horizontal axis (time) scale of the graph 532. The range of the left vertical axis is determined by the minimum and maximum values of all BE and VBE data, and the range of the right vertical axis is determined by the minimum and maximum values of all PH and VPH data. The left and right vertical axes are automatically ranged for each respective minimum and maximum value, so there is not necessarily a "zero" value along the vertical axis for either range.

The values for each measurement are then placed in their proper location within the horizontal (time) and vertical (value) boundaries of the graph 532. All consecutive data points are then connected for a particular lab value, beginning at the earliest value along the horizontal (time) axis for that lab result and ending with the latest time value for that test result. The lines connecting two consecutive lab results are for reference only, and do not necessarily represent any measurements between those two discreet data points. It is also important to note that the connecting line segments begin with the first lab result for that test type and end with the last lab result for that test type. Therefore lines will not begin before the first actual data point or extend beyond the last data point for a particular lab series.

The hematology tab 494 is illustrated in FIG. 24 and presents a patient's hematological laboratory information. The hematology tab 494 is divided into two areas: an upper area presents a hematology lab result table 534, and a lower area presents a hematology chart 536. The hematology lab result table 534 is substantially identical in form and function to the blood gases result table 514 described above, except that the hematology lab result table includes laboratory test results pertaining to hematology, such as white blood count, red blood count, hemoglobin, and so forth. A table of hematology data is illustrated in FIG. 25.

The hematology chart 536 is similar in form and function to the blood gases chart 516 described above. The hematology chart 536 plots color-coded values for hemoglobin (Hgb), white blood count (WBC), and platelets. The chart is built by first finding the earliest and latest collection times of the three values. These two times form the range of the horizontal axis (time) scale. The range of the left vertical axis is determined by the minimum and maximum values of the Hgb and WBC data, and the range of the right vertical axis is determined by the minimum and maximum values of all platelets data. The left and right vertical axis values are automatically ranged for each respective minimum and maximum value, so there is not necessarily a "zero" value for either range. The values for each measurement are then placed in their proper location within the horizontal and vertical boundaries of the chart, and consecutive data points are connected for particular lab value.

Figure 26:
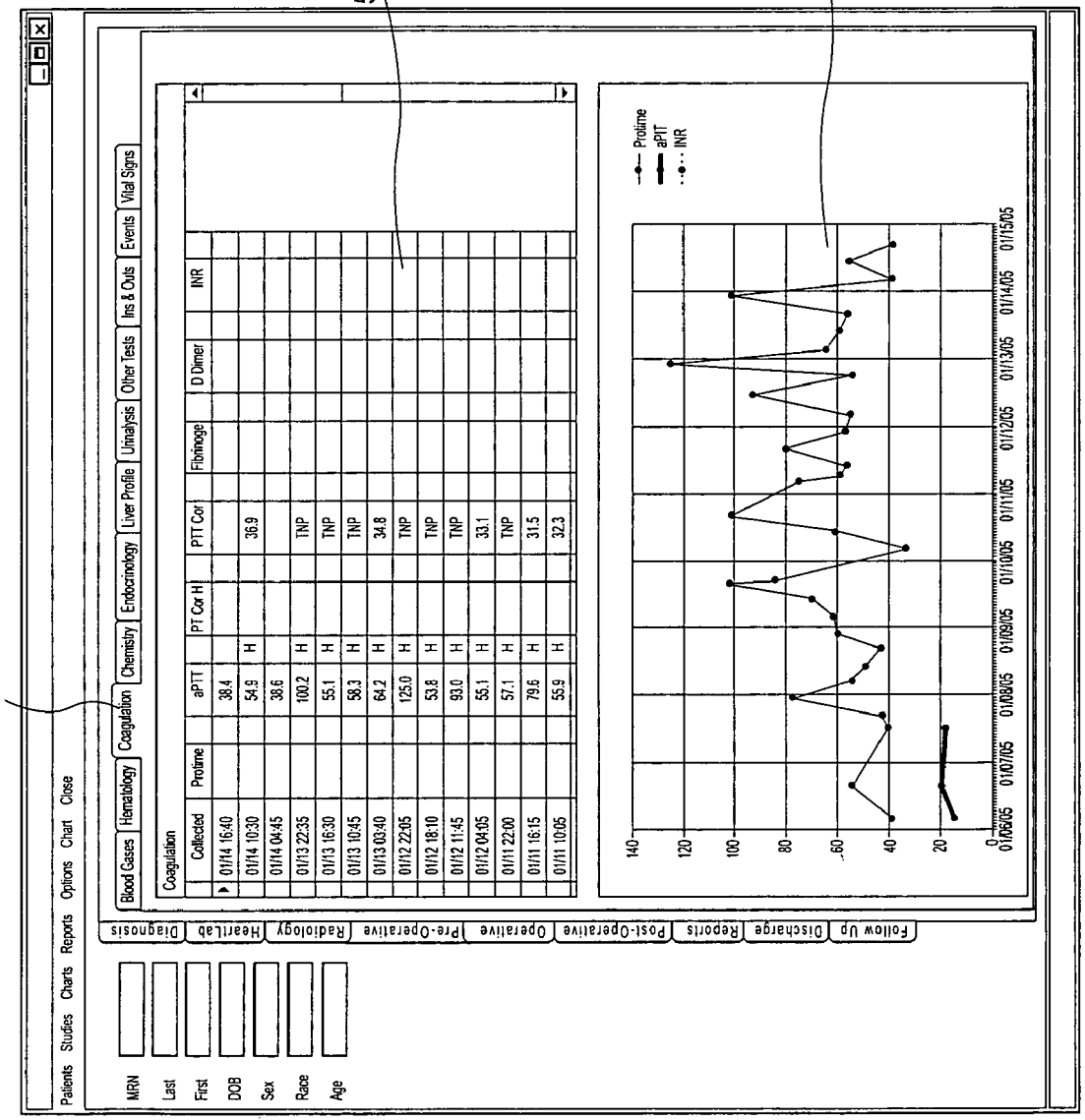
FIG. 26 is the interface of FIG. 22 illustrating a coagulation element of the post-operative tab.

The coagulation tab 496 is illustrated in FIG. 26 and presents a patient's coagulation information. The coagulation tab 496 is divided into two areas: an upper area presents a coagulation lab result table 538, and a lower area presents a coagulation chart 540. The coagulation lab result table 538 is substantially identical in form and function to the blood gases result table 514 described above, except that the coagulation lab result table 538 includes laboratory test results pertaining to coagulation. A table of coagulation data is illustrated in FIG. 27.

The coagulation chart 540 is similar in form and function to the blood gases chart 516 described above. The coagulation chart 540 plots color-coded values for Protime, aPTT, and INR. The chart is built by first finding the earliest and latest collection times of the three values. These two times form the range of the horizontal axis (time) scale. The range of the left vertical axis is determined by the minimum and maximum values of the Protime and aPTT data, and the range of the right vertical axis is determined by the minimum and maximum values of all INR data. The left and right vertical axis values are automatically ranged for each respective minimum and maximum value, so there is not necessarily a "zero" value for either range. The values for each measurement are then placed in their proper location within the horizontal and vertical boundaries of the chart, and consecutive data points are connected for particular lab value, as explained above in relation to the blood gases tab 492.

Figure 28:
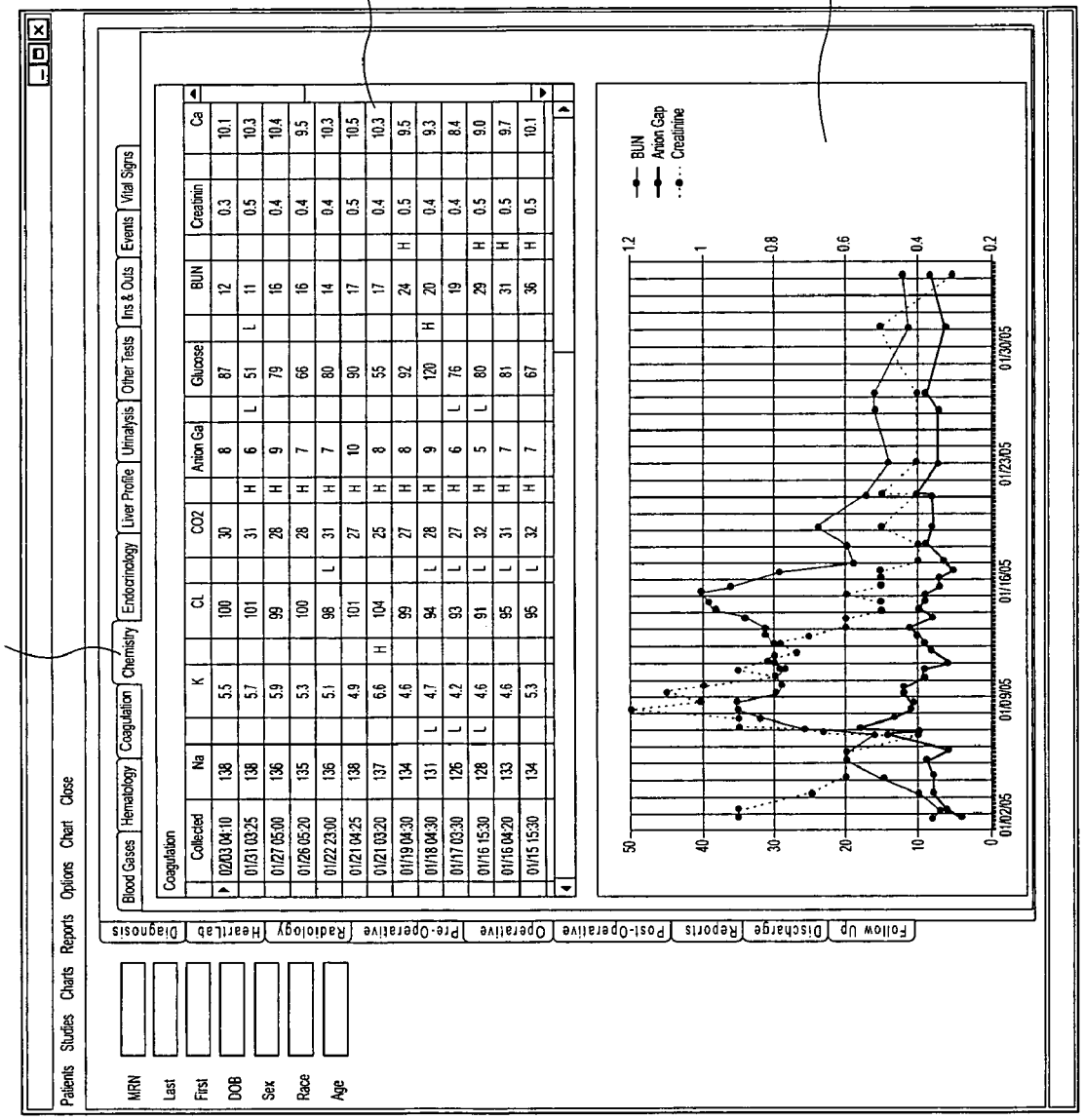
FIG. 28 is the interface of FIG. 22 illustrating a chemistry element of the post-operative tab.

The chemistry tab 498 is illustrated in FIG. 28 and presents chemistry laboratory test results associated with the selected patient. The chemistry tab 498 is divided into two areas: an upper area presents a chemistry lab result table 542, and a lower area presents a chemistry chart 544. The chemistry lab result table 542 is substantially identical in form and function to the blood gases result table 514 described above, except that the chemistry lab result table 542 includes chemistry laboratory test results, such as sodium, potassium, and so forth. A table of chemistry data is illustrated in FIG. 29.

The chemistry chart 544 is similar in form and function to the blood gases chart 516 described above. The chemistry chart 544 plots color-coded values for BUN, Anion Gap, and Creatinine. The chart is built by first finding the earliest and latest collection times of the three values. These two times form the range of the horizontal axis (time) scale. The range of the left vertical axis is determined by the minimum and maximum values of the BUN and Anion Gap data, and the range of the right vertical axis is determined by the minimum and maximum values of all Creatinine data. The left and right vertical axis values are automatically ranged for each respective minimum and maximum value, so there is not necessarily a "zero" value for either range. The values for each measurement are then placed in their proper location within the horizontal and vertical boundaries of the chart, and consecutive data points are connected for particular lab value, as explained above in relation to the blood gases tab 492.

The endocrinology tab 500 is illustrated in FIG. 30 and presents a patient's endocrinology laboratory test results. The endocrinology tab 500 includes an endocrinology lab result table 546 that is substantially identical in form and function to the blood gases result table 514 described above, except that the endocrinology lab result table 546 includes endocrinology laboratory test results. The illustrated endocrinology lab result table includes results for T4, TSH, and free T4.

The liver profile tab 502 is illustrated in FIG. 31 and presents a patient's liver profile laboratory test results. The liver profile tab 502 presents a liver profile lab result table 548. The liver profile lab result table 548 is substantially identical in form and function to the blood gases result table 514 described above, except that the liver profile lab result table 548 includes liver profile laboratory test results, such as T Prot, T Bili, and so forth. A table of exemplary liver profile lab result data is illustrated in FIG. 32.

Figure 33:
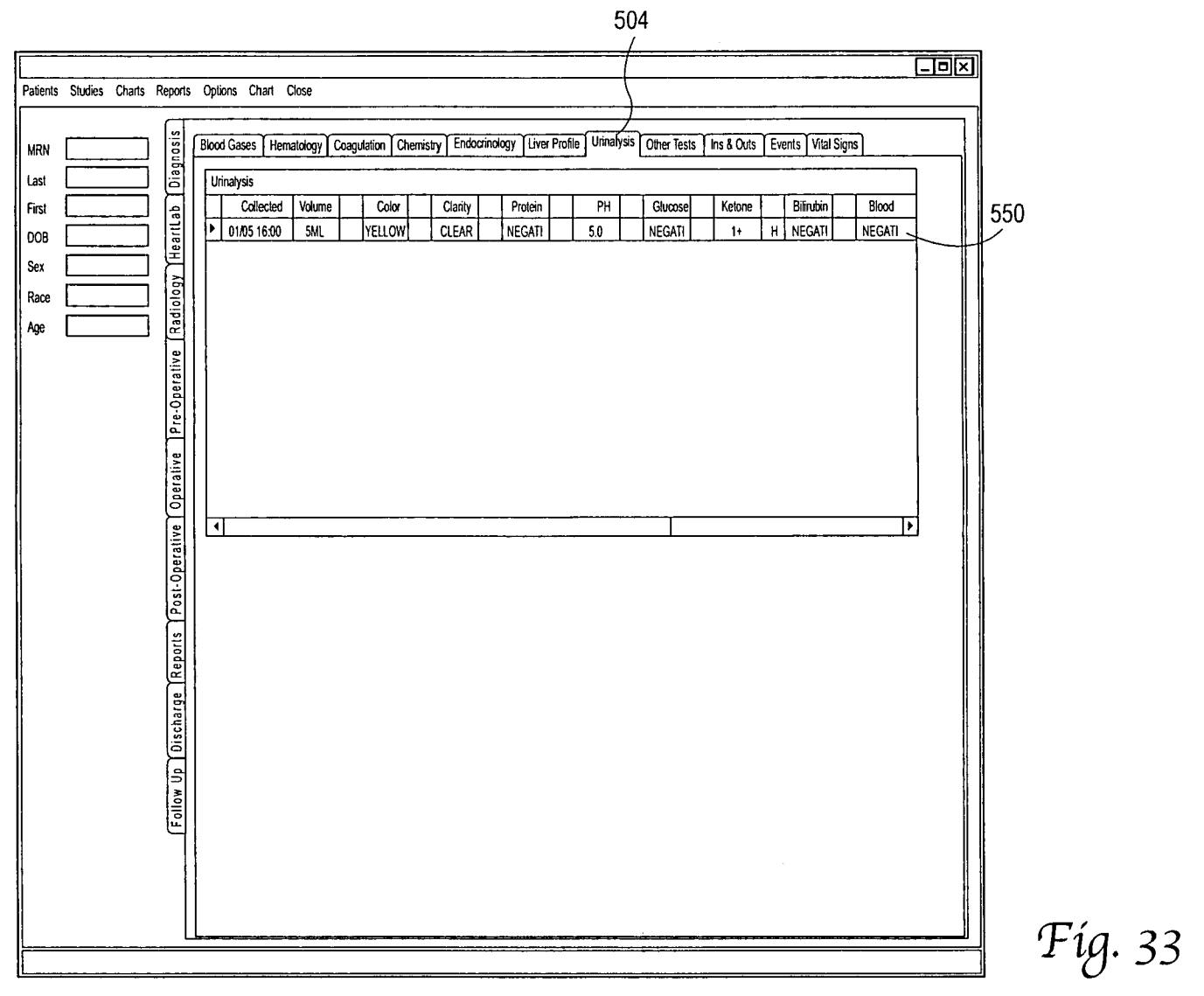

The urinalysis tab 504 is illustrated in FIG. 33 and presents a patient's urinalysis laboratory test results. The urinalysis tab 504 presents a urinalysis lab result table 550. The urinalysis lab result table 550 is substantially identical in form and function to the blood gases result table 514 described above, except that the urinalysis lab result table 550 includes urinalysis laboratory test results, such as volume, color, clarity, and so forth. A table of exemplary urinalysis lab result data is illustrated in FIG. 34.

The other tests tab 506 is illustrated in FIG. 35 and presents a patient's laboratory test results that are not included in one of the previously-defined laboratory groups. The other tests tab 506 presents a lab result table 552. The other tests lab result table 552 is substantially identical in form and function to the blood gases result table 514 described above, except that the other tests lab result table 552 includes laboratory test result information that is not limited to a particular type or category of test. The illustrated other tests lab result table 552 includes a collected column for indicating a date the laboratory test information was collected; a category column for indicating a category of the test being performed; a result type column for indicating a specific name of the test being performed; a result column for indicating a result, or value, of the test being performed; status column for indicating whether the test result is normal or abnormal; a units column for indicating the unit of measure of the test result; and a normal range column for indicating a normal range of the test result for this patient. The status column may include indicators such as H, CH, L, and CL corresponding to high, critically high, low, and critically low, respectively. If a box of the status column is empty, the corresponding test result was normal.

Figure 36:
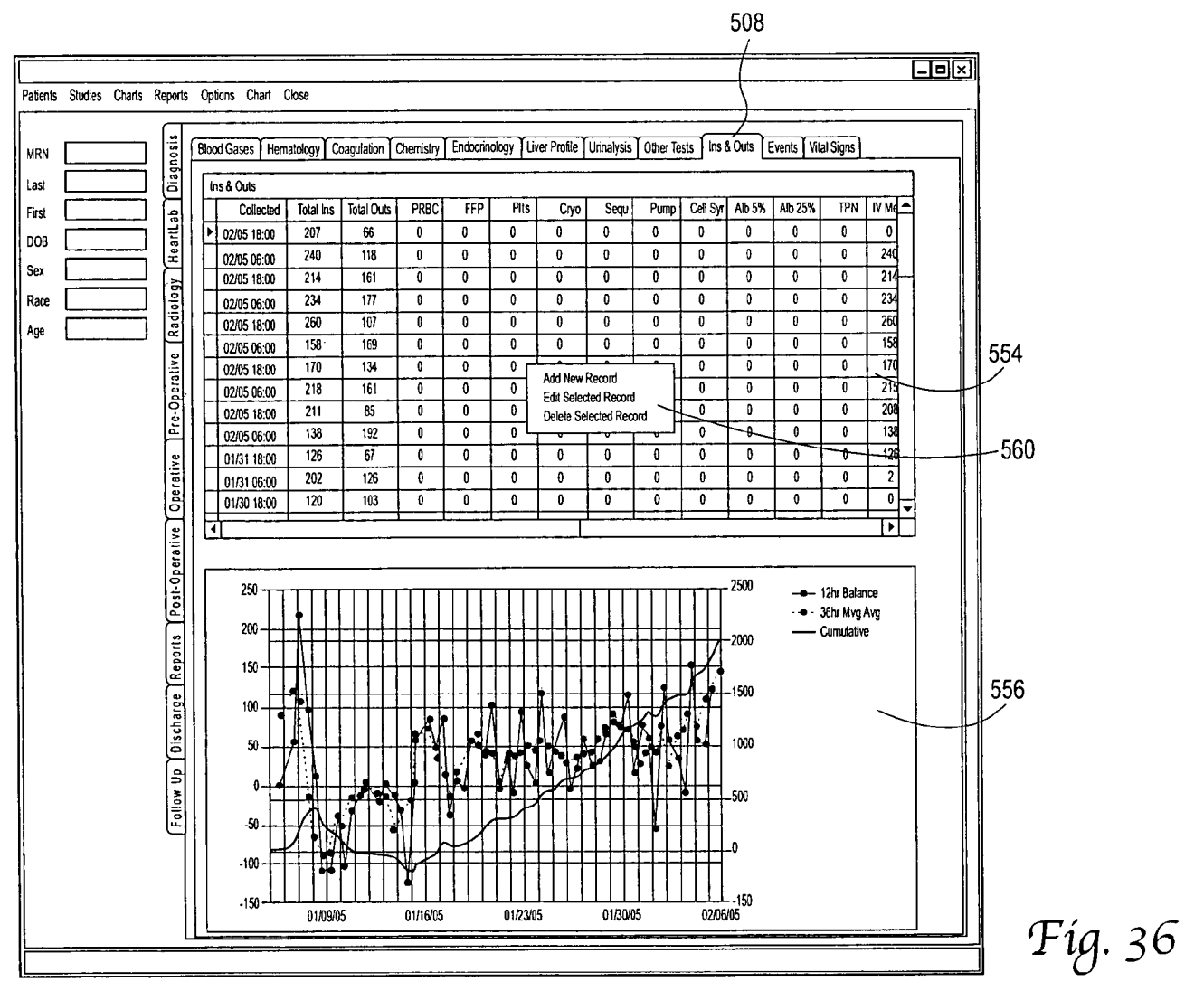

The ins and outs tab 508 is illustrated in FIG. 36 and presents information about all intakes by the selected patient and outputs from that patient over a particular period of time. The information typically relates to a twelve-hour period and the accumulated amounts are recorded on the patient's flow sheet. Intakes may include blood products, intravenous medications and fluids, and feeding intakes. Typical outputs include chest tube drainage and urine. The ins and outs tab 508 is divided into two areas: an upper area presents an ins and outs result table 554, and a lower area presents an ins and outs chart 556. The ins and outs result table 554 is similar in form and function to the blood gases result table 514 described above, except that the ins and outs result table 554 includes the intakes and outputs information described above and generally does not include a status column.

The table of FIG. 37 lists various values that may appear in the lab results table 554. Some of the values listed in FIG. 37 are not visible in the table 554 because they are in columns that are beyond the scope of the chart window. It will be appreciated that the columns that are not visible are substantially identical in form to those that are visible, and may be accessed by manipulating a scroll bar located near a bottom of the chart window. Each cumulative intake and output entry is on a separate row of the table 554, and the collected column of each row specifies the ending date and time that the entry represents.

The ins and outs chart 556 is similar in form and function to the blood gases chart 516 described above. The ins and outs chart 556 plots color-coded values for a twelve-hour balance, a thirty-six hour moving average, and a cumulative value. The twelve-hour balance represents total intake less total output for the twelve-hour period as recorded on the nursing flow sheet. The thirty-six hour moving average represents the average of three consecutive twelve-hour balances, typically the current twelve-hour balance and the next two. The thirty-six hour moving average tends to smooth out the more drastic fluctuations of the twelve-hour balance, and show a more accurate trend of ins and outs balances. The cumulative value represents a running total of all twelve-hour balances over time, both positive and negative, beginning at zero.

The ins and outs chart 556 is built by first finding the earliest and latest collection times of the twelve-hour balance values. These two times form the range of the horizontal axis (time) scale. The twelve-hour balance data is then sequenced from earliest to latest and the thirty-six hour moving average and cumulative values are calculated. The range of the left vertical axis is determined by the minimum and maximum values of all twelve-hour balance and thirty-six hour moving average data, and the range of the right vertical axis is determined by the minimum and maximum values of all cumulative data.

The left and right vertical axis values are automatically ranged for each respective minimum and maximum value. The values for each measurement are then placed in their proper location within the horizontal (time) and vertical (value) boundaries of the chart. All consecutive data points are then connected for a particular data series, beginning at the earliest value along the horizontal axis for that series and ending with the latest horizontal axis value for that series. The lines connecting two consecutive data points are for reference only, and do not necessarily represent any measurements between those two discreet data points.

Figure 44:
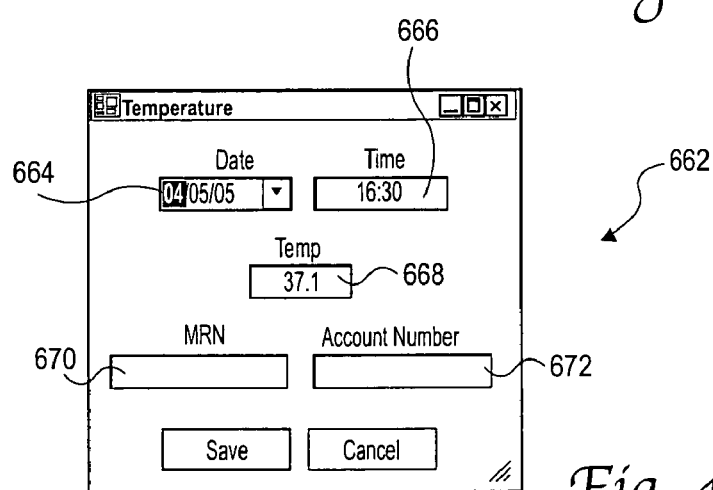
FIG. 44 is an exemplary data entry form for submitting patient body temperature information associated with the vital signs element of FIG. 41.

The ins and outs tab 508 also has an associated ins and outs context menu 560, illustrated in FIG. 44, that is presented in response to a pre-determined user input, such as depressing a mouse button. The context menu 560 includes three menu items: add new record, edit selected record, and delete selected record. When the user selects the add new record context menu item, the program presents a blank ins and outs entry form 558, illustrated in FIG. 38.

The form 558 presents a date field 562 that represents the ending date of the period for which the ins and outs are being entered. The value in the date field defaults to the current date, but the user may change the date in this field by selecting the drop-down menu button and choosing another date from the drop-down menu. A time field 564 represents the ending time of the period for which the ins and outs are being entered. The time field 564 may also default to a particular time, such as 06:00 or 18:00, which correspond to nursing flow sheet cut-off times. The default value may be, for example, the closest previous cut-off time, but can be any time submitted in the twenty-four hour (00:00) format. The "Accumulated Until" radio buttons 566,568 are associated with the time field and allow the user to change the value to the time field to either 6:00 a.m. (06:00) or 6:00 p.m. (18:00).

The cumulative intake 570 and cumulative output 572 fields are read-only fields that maintain running totals of all intake 574 fields and all output 576 fields, respectively. The intake 574 fields and the output 576 fields receive data from the user relating to each of the topics listed in FIG. 37. A medical record number (MRN) field 578 defaults to the MRN of the current patient, but may be changed by the user. An account number field 580 defaults to the account number of the current visit, but may also be changed by the user. When a new record has been created and saved, the program automatically and immediately updates the ins and outs results table 554 and the ins and outs chart 556 to reflect the new information.

The edit selected record menu item of the context menu 560 is a record-specific menu item, therefore the user must select a specific row within the ins and outs result table 554 prior to activating the context menu 560 and selecting this menu item. Once this item is selected, the program presents the ins and outs entry form 558 containing information from the selected row. The user may then change the values in editable fields and save the new information by selecting the save button. Once a record has been edited and saved, the program automatically and immediately updates the ins and outs results table 554 and the ins and outs chart 556 to reflect the new information.

The delete selected record menu item of the context menu 560 is a record-specific menu item, therefore the user must select a specific row within the ins and outs result table 554 prior to activating the context menu 560 and selecting this menu item. When the user selects the delete selected record menu item, the program presents a message asking the user to confirm the deletion of the selected record. If the user submits a positive response to the confirmation request, the program automatically deletes the corresponding ins and outs data and updates the ins and outs results table 554 and the ins and outs chart 556 to reflect the change.

Figure 39:
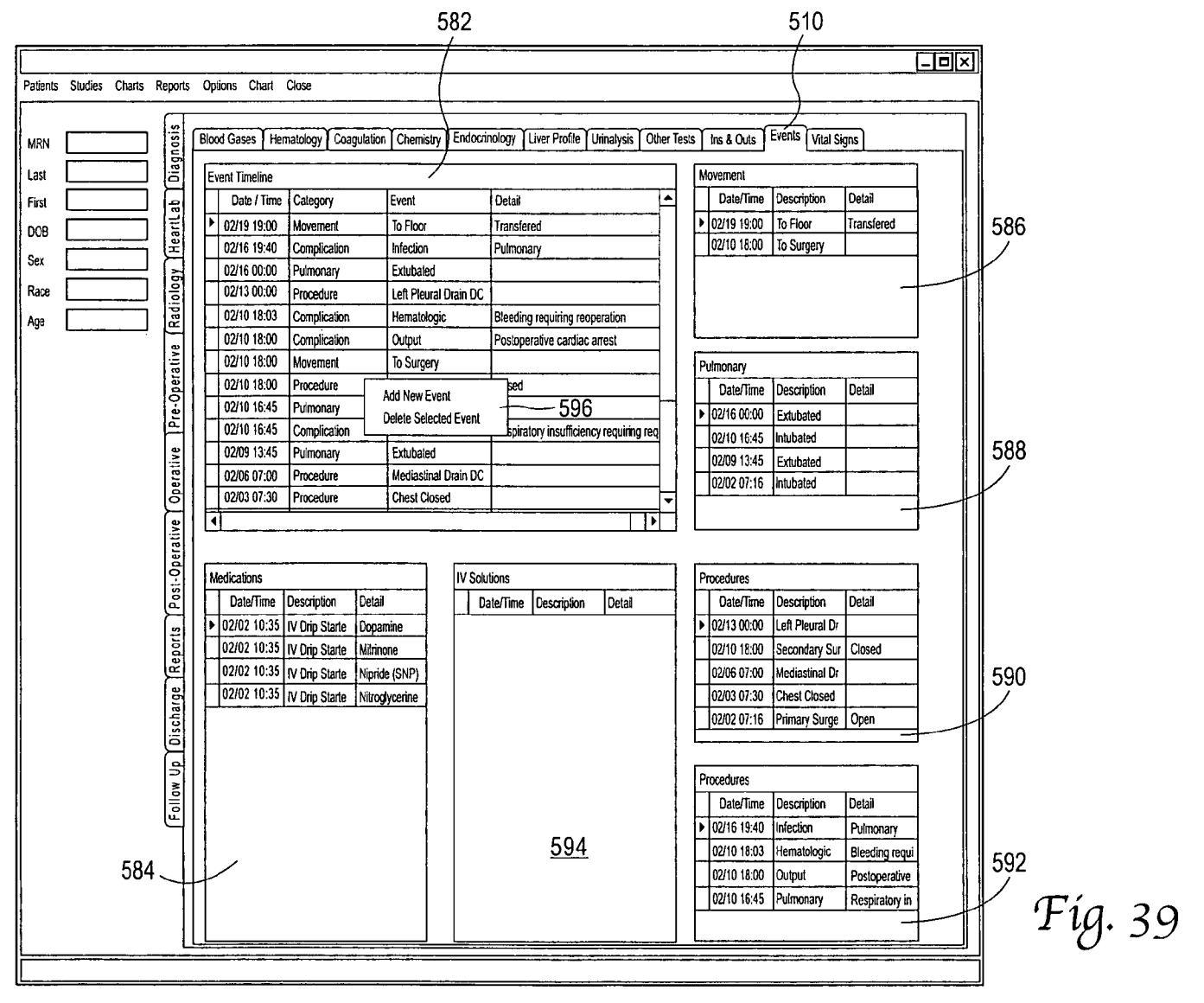

The events tab 510 is illustrated in FIG. 39 and generally presents event information relating to the selected patient. The illustrated events tab 510 presents an event timeline table 582 and a plurality of event category tables. The event category tables include medications 584, movements 586, pulmonary 588, procedures 590, complications 592, and IV solutions 594.

The event timeline table 582 lists all of the events that have occurred for the selected patient over a predetermined period of time in reverse chronological order. The length, beginning date, and ending date of the predetermined period of time depends on how the visit view was invoked. If the user invoked the visit view by selecting a current clinical data context menu item from the department view, for example, the predetermined period of time is the user-defined "lookback" period that ends with today's date and begins a user-determined number of days prior to today's date. Alternatively, if the user invoked the visit view by selecting a previous visit from the patient view and then selected the view clinical data 340 menu item, the predetermined period of time corresponds to that visit so that the information includes all of the lab results collected during the visit.

Each row of the event timeline table 582 corresponds to an event, and the rows are divided up into columns of information. A date/time column indicates a date and time of the event; a category column indicates a type of the event, wherein the event type corresponds to one of the event category tables; an event column presents the main description of the event; and a detail column presents more detailed information about the event, if required.

Figures 38, 40:
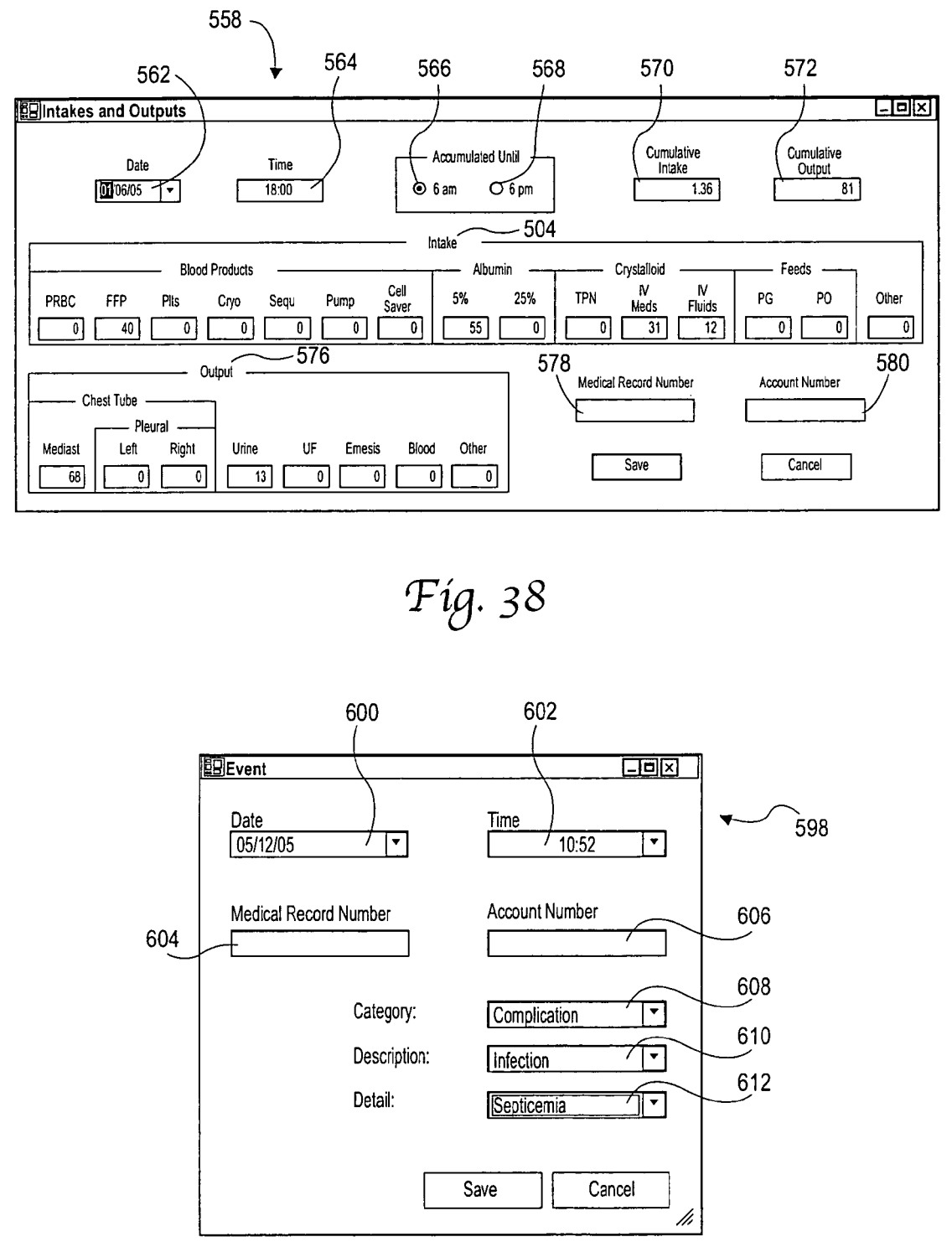

Events are added to and removed from the event timeline table 582 via a context menu 596 associated with the table 582. An add new event context menu item enables the user to enter a new event of any category into the event timeline table 582 and the appropriate event category table. When the user selects this context menu item, the program presents the event entry form 598 as illustrated in FIG. 40. A date field 600 of the form 598 defaults to the current date, but the user may change the date by selecting a drop-down menu button to activate a drop-down menu and choosing a date from the menu. A time field 602 defaults to the present time, but the user may change the time to any (valid) time. A medical record number (MRN) field 604 defaults to the MRN of the current patient, and an account number field 606 defaults to the account number of the current visit.

A category drop-down menu 608 enables the user to select a category for the event, wherein each available category corresponds to one of the event category tables. Once the user selects a category from the category drop-down menu 608, the program presents an event description 610 drop-down menu. The description drop-down menu 610 presents various descriptions corresponding to the selected category. Once the user selects a description of the event, the program presents a detail drop-down menu 612 if there are details associated with the description chosen by the user. If there are not details associated with the description chosen by the user, the program activates a save button so that the user can save the new event information. The program also activates the save button when the user selects detail information from the detail drop-down menu 612.

Selecting the delete selected event menu item of the context menu 596 causes the program to remove the selected event from the patient's record. The program also automatically removes the row of the event timeline table 582 and one of the event category tables corresponding to the event.

Once an event is entered into the event timeline table 582, the program automatically associates the event with one of the five event category tables, depending on which category the user selects in the add new event form 598 when initially submitting event information. As explained below in greater detail, specific events can be plotted in any of the charts described above concurrently with lab result information.

Figure 41:
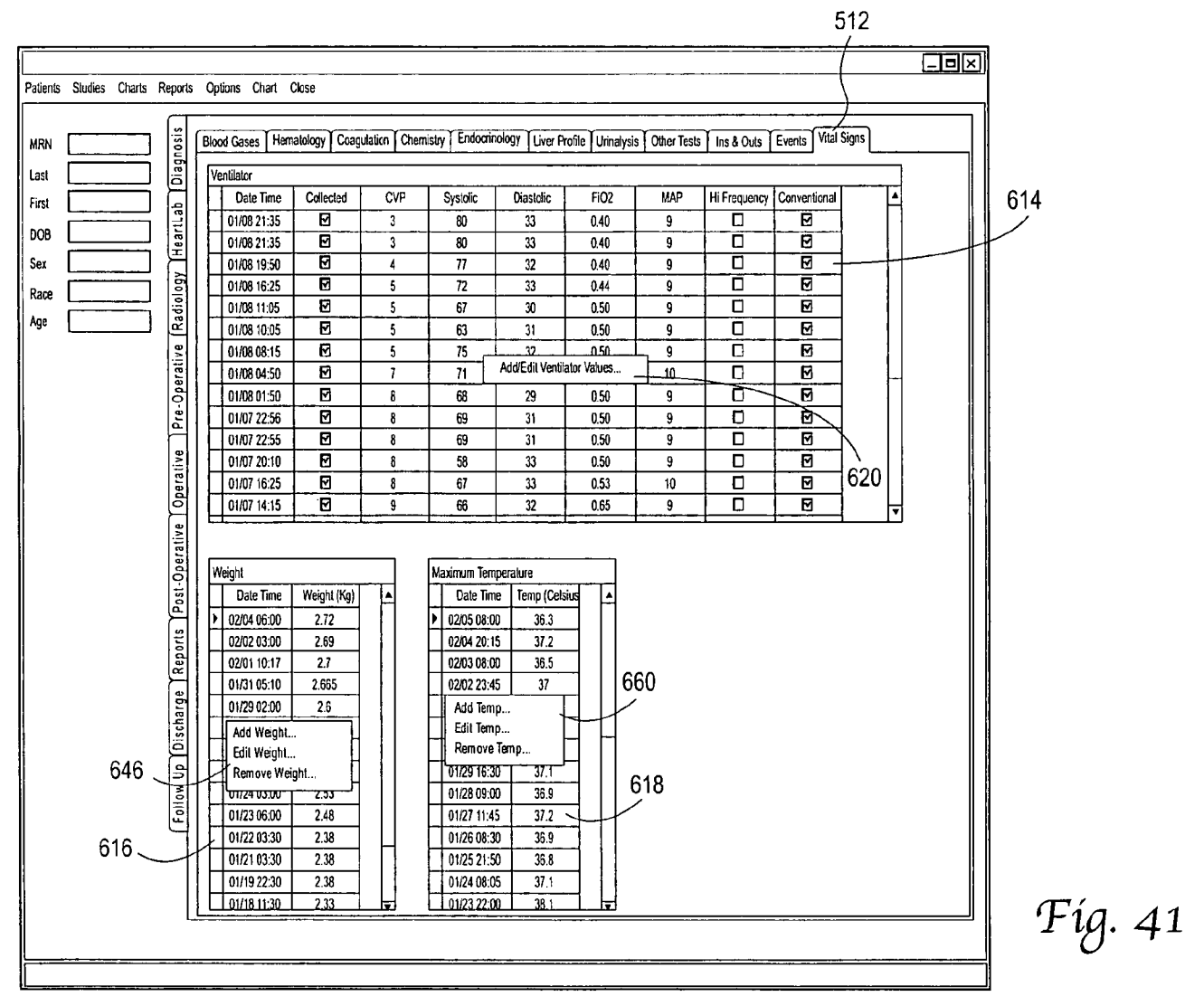

The vital signs tab 512 is illustrated in FIG. 41. The tab 512 presents three tables, including a ventilator table 614, a weight table 616, and a maximum temperature table 618. The ventilator table 614 displays information associated with ventilator settings and measurements when a patient is on the ventilator. Ventilator settings are always recorded along with a particular blood gas sample, therefore the program generates a new row in the ventilator table 614 whenever new blood gas lab results are submitted to the program.

There is one row of information in the ventilator table 614 for each blood gas lab result received, wherein the information includes all ventilator settings and measurements that occur for a specific patient and the rows are presented in reverse chronological order. The rows are divided into columns including a date/time column that indicates the date and time of the blood gas sample and associated ventilator reading; a collected column that identifies whether the ventilator value has been entered, has been verified to contain no valid data, or has been verified and entered; a CBP column; a systolic column for indicating a systolic blood pressure reading; a diastolic column for indicating a diastolic blood pressure reading; an FiO2 column; an MAP column for indicating a mean airway pressure; a hi frequency column for indicating that the ventilator is set to a high frequency mode; and a convention column for indicating that the ventilator is set to a convention frequency mode.

Figure 42:
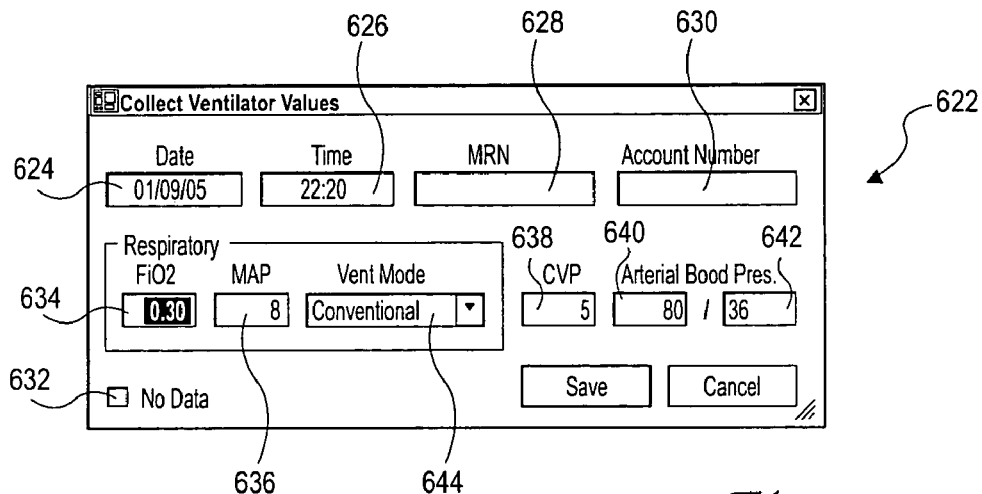
FIG. 42 is an exemplary data entry form for submitting ventilatory information associated with the vital signs element of FIG. 41.

The user adds, edits, and deletes information from the ventilator table 614 using a ventilator context menu 620. The add/edit ventilator settings context menu item enables the user to add ventilator settings and measurements to a row of the ventilator table 614 selected by the user. When the user selects a row of the table 614, that row is entirely highlighted in blue. When the user activates the context menu 620 and selects the add/edit ventilator values menu item, the program presents a collect ventilator values entry form 622, as illustrated in FIG. 42. The program presents the form 622 with data fields corresponding to date 624, time 626, MRN 628, and account number 630, wherein these data fields are pre-filled with information for the selected patient, visit, and ventilator row date and time. Furthermore, those fields are read-only and cannot be modified by the user.

If there is no ventilator data associated with a blood gas lab result, the user checks a no data checkbox 632. This will indicate that the blood gas lab result has been verified to have no associated ventilator data, as opposed to a blood gas lab result which hasn't had the ventilator data entered yet.

The user enters information into FiO2 634, MAP 636, CVP 638, and arterial blood pressure systolic 640 and diastolic 642 fields directly from the flow sheet data for the selected ventilator entry. The user indicates a vent mode from the vent mode drop-down menu 644 according to the ventilator mode at the time the entry is recorded. The program saves the data to the ventilator table 614 row when the user selects the save button, or discards the data when the user selects the cancel button.

The weight table 616 lists all weights recording during a particular patient visit. There is one row of information in the weight table 616 for each recorded weight, and each row is divided into columns of information. A date/time column indicates a date and time that the weight was measured, while a weight column provides the measured weight in kilograms. The table includes all weight measurements that occur for a specific patient in reverse chronological order.

Figure 43:
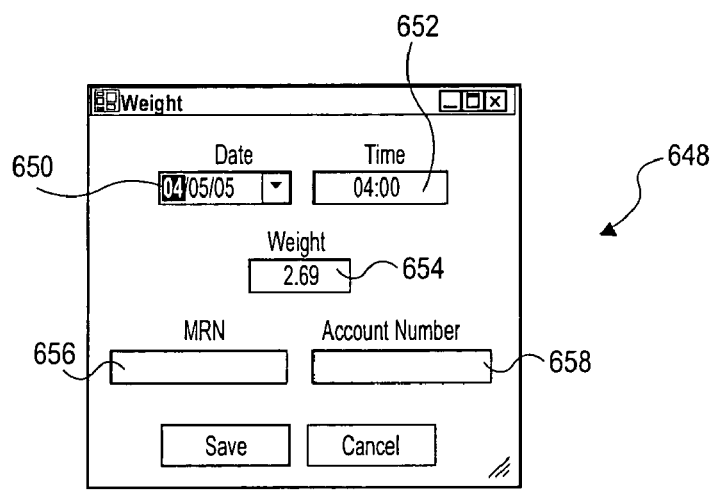
FIG. 43 is an exemplary data entry form for submitting patient weight information associated with the vital signs element of FIG. 41.

A weight table context menu 646 presents three context menu items, including add weight, edit weight, and remove weight menu items. The add weight context menu item enables the user to enter a new weight measurement to the weight table 616. When the user selects this menu item, the program presents the weight entry form 648 illustrated in FIG. 43. A date field 650 defaults to the current date, and the user may choose a date by selecting the drop-down menu button associated with the date field 650 and choosing a date from the drop-down menu. A time field 652 defaults to the current time, and the user may enter any (properly formatted) time value. A weight field 654 is left blank for the user to fill in, and an MRN field 656 is filled in by the program with the medical record number of the current patient. The MRN field is read-only and thus cannot be modified by the user. An account number field 658 is also read-only, and contains the account number of the currently-selected visit. When the user has completed the form 648, he or she saves the information by selecting the save button or discards the information by selecting the cancel button. There is typically one weight recorded for a twenty-four hour period, although the program enables the user to submit patient weight information at any frequency.

The edit weight menu item of the weight context menu 646 enables the user to change a previously submitted weight measurement. This menu item is row specific, so the user must select a specific row of the weight tab 616 before activating the context menu 646 and choosing this item. When the user has selected a row and chosen the edit weight context menu item, the program presents the weight entry form 648, described above, populated with the data from the selected row of the weight table 616. The user can then modify one or more of the date 650, time 652, and weight 654 fields and save or discard the information as explained above.

The remove weight menu item of the weight context menu 646 enables the user to remove a previously submitted weight record from the weight table 616. This menu item is row specific, so the user must choose a row of the table 616 before activating the context menu 646 and choosing this item. When the user selects a row and chooses the remove weight menu item, the program requests a confirmation from the user in a conventional manner and removes the row of information from the table 616 if the user confirms the removal request.

The maximum temperature table 618 lists all patient temperatures recorded during a particular patient visit in reverse chronological order. There is one row of information in the table 618 for each recorded temperature, and each row is divided into several columns. A date/time column provides the date and time the temperature was measured, and a temperature column indicates a measured temperature in degrees Celsius.

A maximum temperature table context menu 660 presents three context menu items, including add temperature, edit temperature, and remove temperature menu items. The add temperature context menu item enables the user to enter a new temperature measurement to the maximum temperature table 618. When the user selects this menu item, the program presents the temperature entry form 662 illustrated in FIG. 44. A date field 664 defaults to the current date, and the user may choose a date by selecting a drop-down menu and choosing a date from the drop-down menu. A time field 666 defaults to the current time, and the user may enter any (properly formatted) time value. A temperature field 668 is left blank for the user to fill in, and an MRN field 670 is filled in by the program with the medical record number of the current patient. The MRN field 670 is read-only and thus cannot be modified by the user. An account number field 672 is also read-only, and contains the account number of the currently-selected visit. When the user has completed the form 662, he or she saves the information by selecting the save button or discards the information by selecting the cancel button. Typically the highest temperature for a twenty-four hour period is recorded, although the program enables the user to submit patient temperature information at any frequency.

The edit temperature item of the maximum temperature context menu 660 enables the user to change a previously submitted temperature measurement. This menu item is row specific, so the user must select a specific row of the maximum temperature table 618 before activating the context menu 660 and choosing this item. When the user has selected a row and chosen the edit temperature context menu item, the program presents the temperature entry form 662, described above, populated with the data from the selected row of the maximum temperature table 618. The user can then modify one or more of the date 664, time 666, and temperature 668 fields and save or discard the information as explained above.

The remove temperature item of the maximum temperature context menu 660 enables the user to remove a previously submitted temperature record from the maximum temperature table 618. This menu item is row specific, so the user must choose a row of the table 618 before activating the context menu 660 and choosing this item. When the user selects a row and chooses the remove temperature menu item, the program requests a confirmation from the user in a conventional manner and removes the row of information from the table 618 upon receiving a user confirmation.

The Reports Tab

Figure 45:
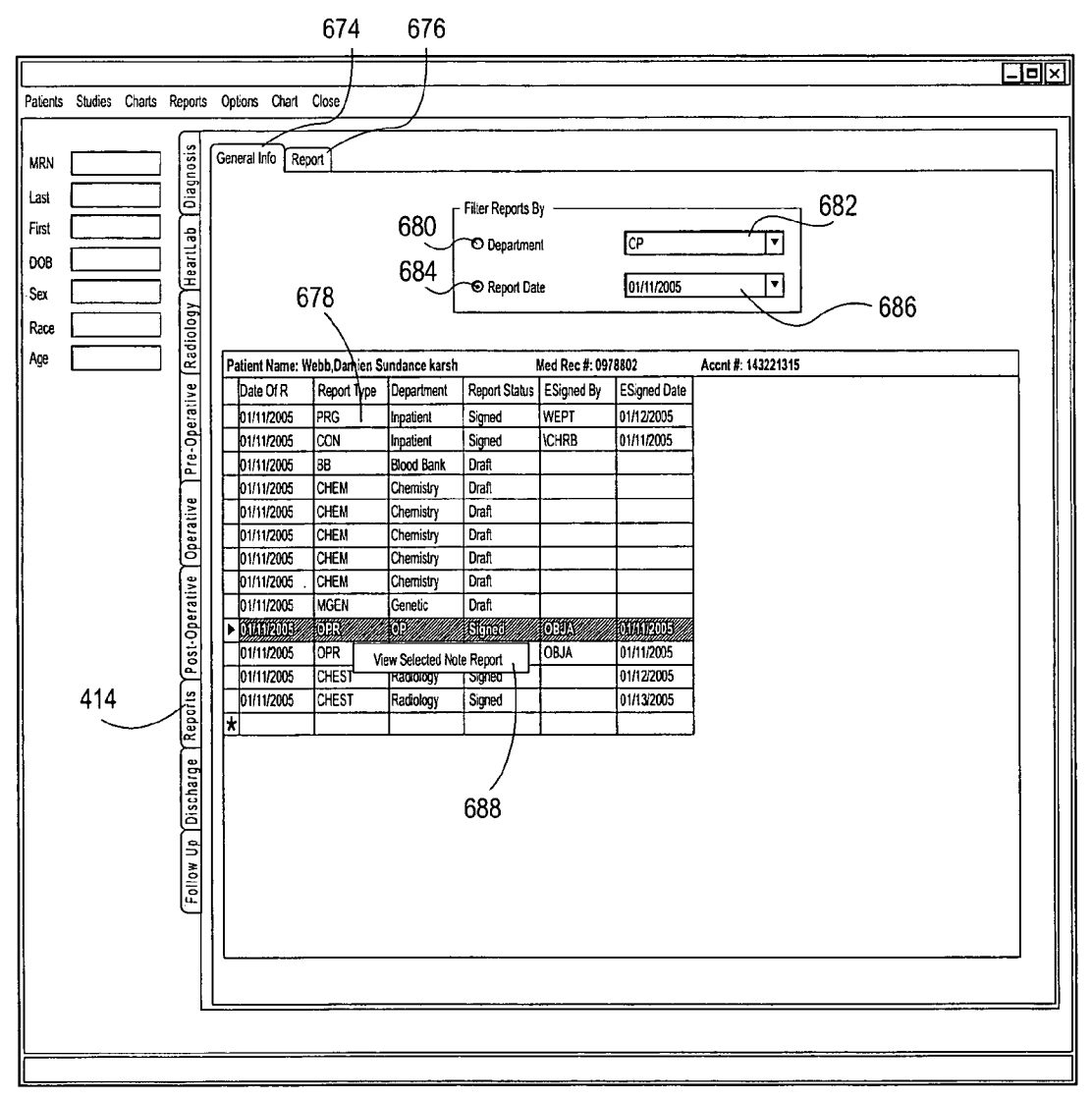

The reports tab 414 is illustrated in FIG. 45 and contains a list of reports from various departments associated with the selected visit and patient. These reports are typically text-based electronic documents and clinical evaluations. The reports are stored in the hospital information system (HIS), and the program enables the user to select and view the documents via a user interface generated by the program. The reports tab 414 presents two nested tabs, including a general information tab 674 and a report tab 676.

The general information tab 674 includes a table 678 of reports that can be displayed according to department or report date. When the user selects a department radio button 680 an associated drop-down menu 682 provides a list of all departments that have provided one or more reports for the selected patient's visit. When the user selects a department from the department drop-down menu 682, the table 678 displays a list of all reports provided by the selected department during the patient's visit.

Figure 46:
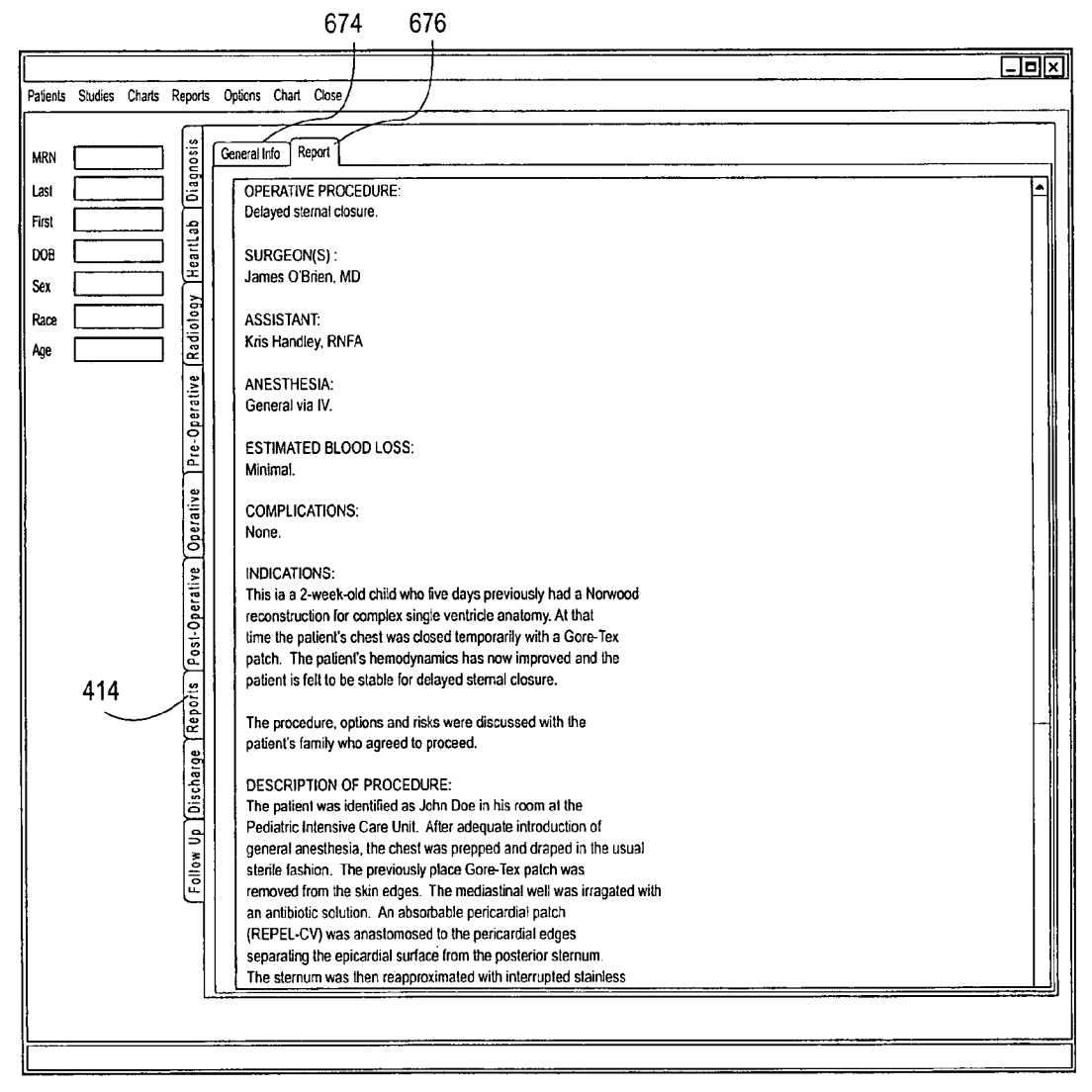

When the user selects a report date radio button 684, an associated drop-down menu 686 provides a list of all dates in which reports were generated. When the user selects a particular date from the date drop-down menu 686, the table 678 displays a list of all reports provided on the selected date. The user views a particular report by selecting the report from the list of reports in the table 678, activating a context menu 688, and selecting a view selected report menu item. This causes the reports tab 414 to switch to the nested report tab 676 which displays the selected report, as illustrated in FIG. 46.

The Discharge and Follow Up Tabs

The discharge tab 416 presents patient information associated with the discharge of the patient from the hospital, and the follow up tab presents patient information associated with follow up visits or contacts with the patient. The information in these tabs may be presented in a manner similar to that of the tabs described above.

The Research View

Figure 47:
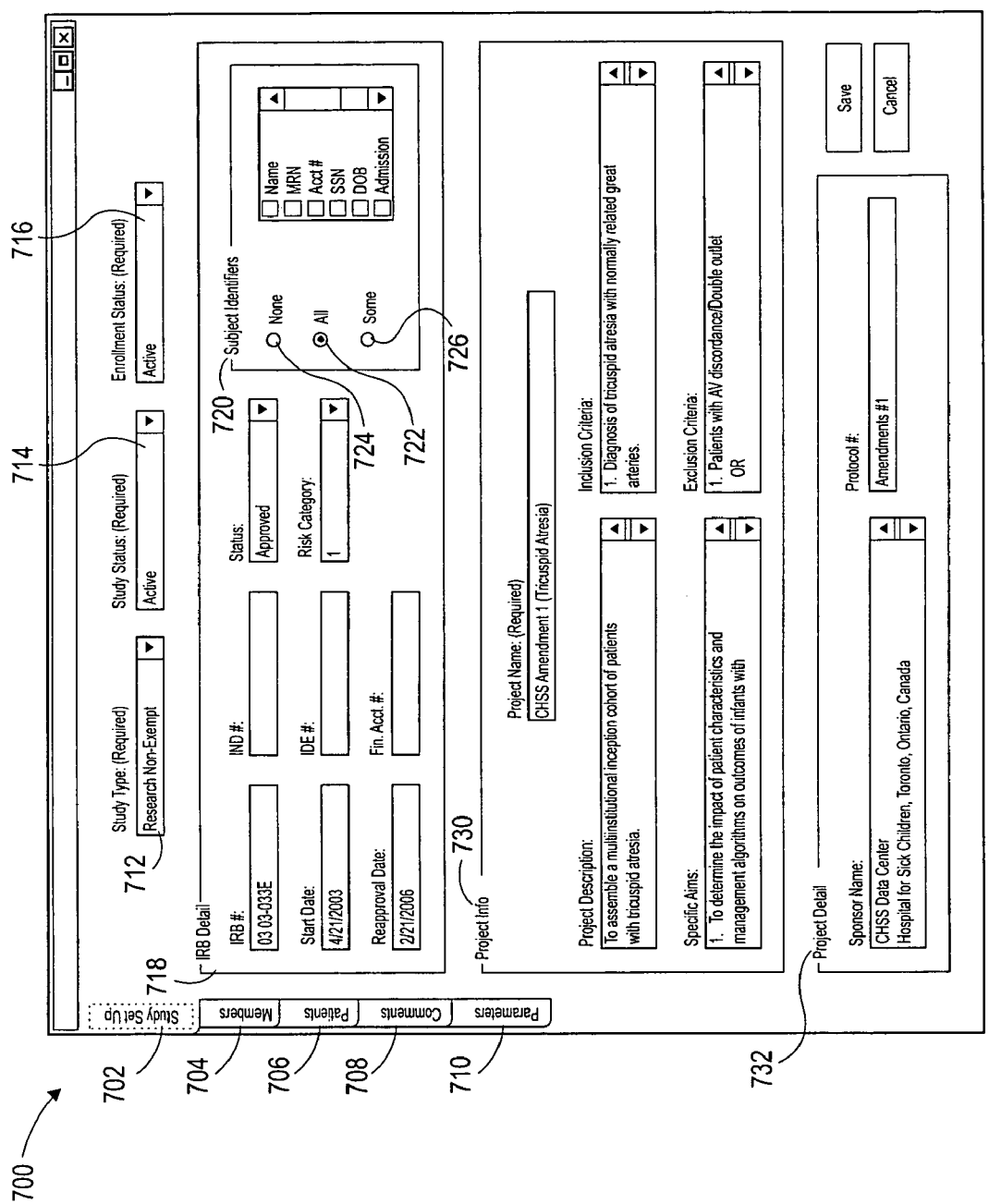
FIG. 47 is an exemplary top-level user interface associated with a research view of the present invention and illustrating a study setup tab of the interface.

Referring to FIG. 47, the research view presents a top-level interface 700 that enables users to set up and manage research studies. The interface 700 allows only users with the role of system administrator to enter or change data associated with the management of research studies. Each member of a study, however, is allowed to submit information pertaining to that study. The interface 700 is launched when the user selects an add new study menu item of the study menu, as explained below. The illustrated research view interface 700 includes various tabs, wherein each tab relates to a separate interface element. The tabs include study setup 702, members 704, patients 706, comments 708, and parameters 710 tabs.

The study setup tab 702 is illustrated in FIG. 47 and presents a research form for setting up a new research study. A new research study must be set up and saved before research team members can be added, patients can be enrolled, or any other detailed information can be submitted about the study. The study setup tab 702 provides general information about the study. A study type drop-down menu 712 presents various study type options, including quality assurance/quality improvement (QA/QI), clinical program, research exempt, and research non-exempt menu items. A study status drop-down menu 714 presents various study status options, including active, inactive, pending, and closed menu items. An enrollment status drop-down menu 716 presents various enrollment options, including active, inactive, and closed. The study type 712, study status 714, and enrollment status 716 drop-down menus are required data fields, therefore the user must choose an item from each of these menus to set up a new study.

A section labeled "IRB Detail" 718 includes various data fields for receiving institutional review board (IRB) information if the research study has IRB approval. Within the IRB detail section 718 is a subject identifiers section 720 which defines what patient-specific information can be provided on reports. If all patient information can be provided, the user selects an "All" radio button 722. If no patient information can be provided, the use selects a "None" radio button 724. If only certain pieces of patient information can be provided, the user selects a "Some" radio button 726 and then checks the specific pieces of information that will be provided in a list 728 of possible pieces of information. A section titled "Project Info" 730 and a section titled "Project Detail" 732 each include various data fields for receiving information specific to the project. The user stores the submitted information and closes the window by selecting the save button, or discards the information and closes the window by selecting the cancel button.

Figure 48:
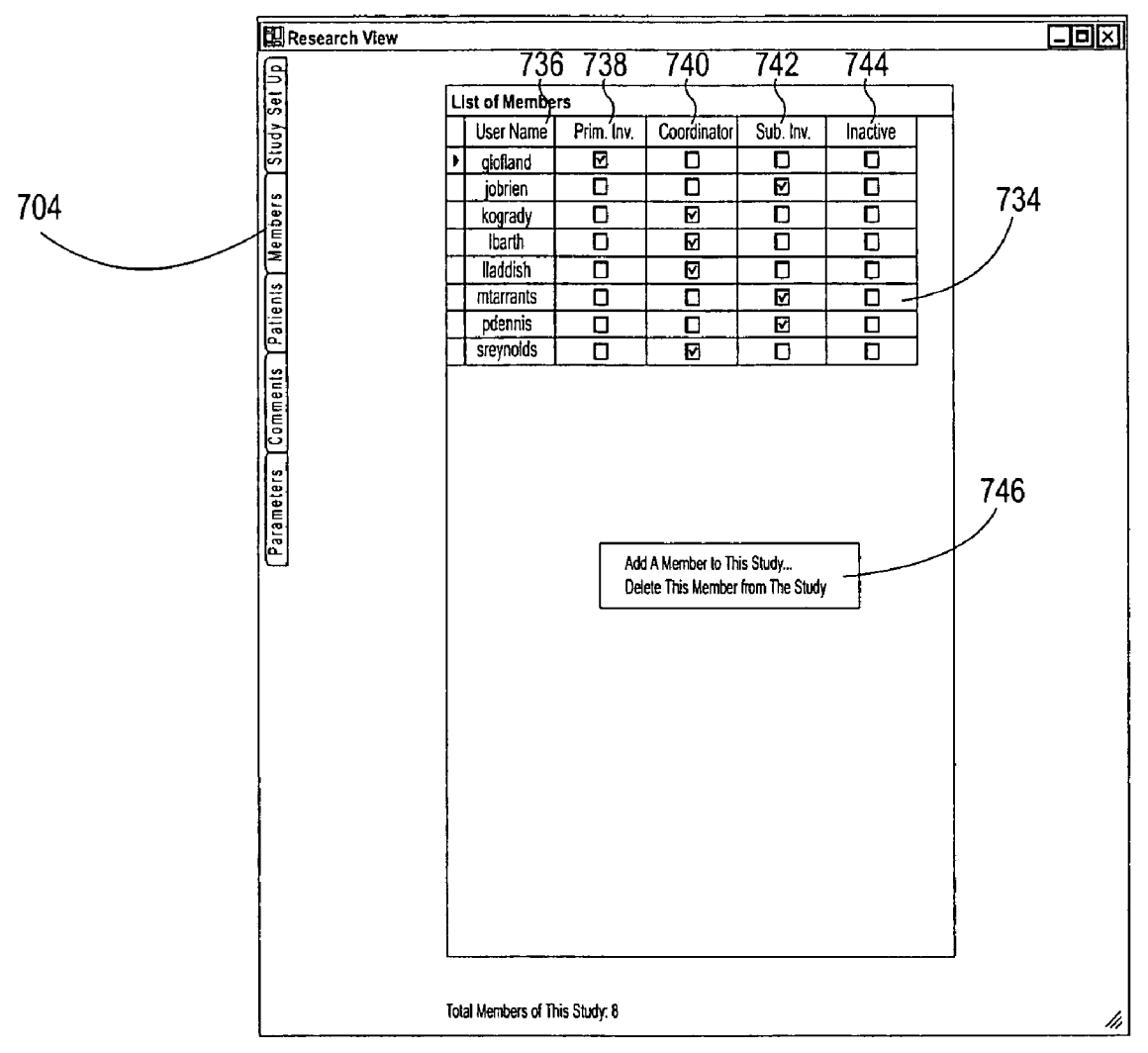

The members tab 704 is illustrated in FIG. 48, wherein the tab generally presents a list of members of a study and enables the user to add and remove study members. Only designated members of a study may view study information or enter patient study data. Users must have a system user account and must be added to the study by a system administrator to become members of a selected study. As illustrated in FIG. 48, the members tab 704 presents a table 734 of members of the study along with various pieces of information pertaining to each member. A user name column 736 presents the study member's name; a primary investigator column 738 presents a checkbox that is checked if the member is a primary investigator of the study; a coordinator column 740 presents a checkbox that is checked if the member is a study coordinator; a sub-investigator column 742 presents a checkbox that is checked if the member is a study sub-investigator; and an inactive column 744 presents a checkbox that is checked if the member is no longer an active member of the study.

Figure 49:
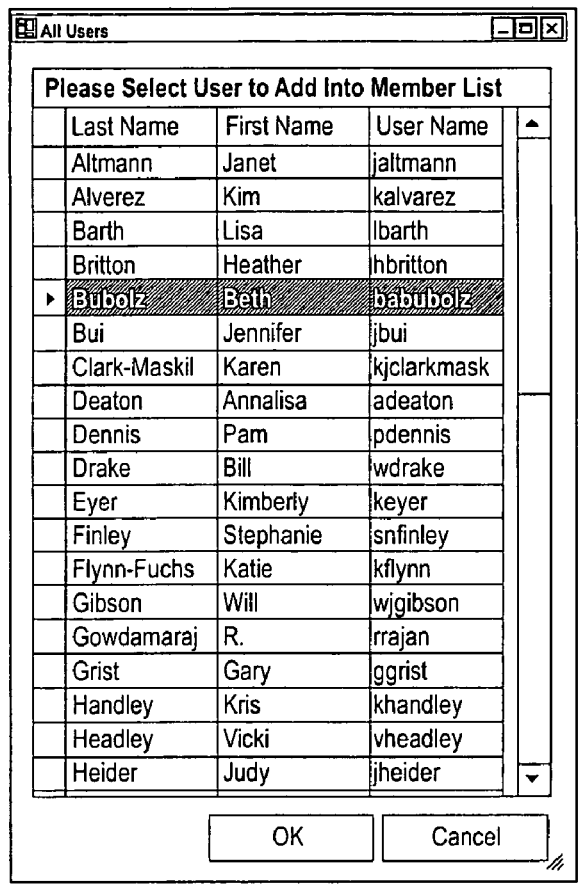
FIG. 49 is an exemplary data entry form for selecting a member to add to a list of study members of the members tab of FIG. 47.

A context menu 746 is associated with the table 734 and includes two menu items: an "Add A Member to This Study" menu item and a "Delete This Member from the Study" menu item. When the user selects the "Add A Member to This Study" menu item the program presents a new study member form 748 illustrated in FIG. 49. Using the form 748, the user scrolls through a list of system users and adds a user to the study by selecting the user and then selecting an ok button. Newly-added study members are given the default role of sub-investigator, but the user can change the member's role by selecting another role from the possible check boxes in the table 734 of study members.

To delete a member from the list of study members, the user must first select the member from the table 734 of study members and then activate the context menu 746. When the context menu 746 appears, the user selects the "Delete This Member from the Study" menu item. The program requests a confirmation from the user in a traditional manner, and when the user confirms the request the program removes the selected member from the study and from the study members table 734. If the user desires to maintain a record that a particular member was part of the study at one time, the user checks the appropriate box in the inactive column 744 as opposed to deleting the member entirely from the study.

Figure 50:
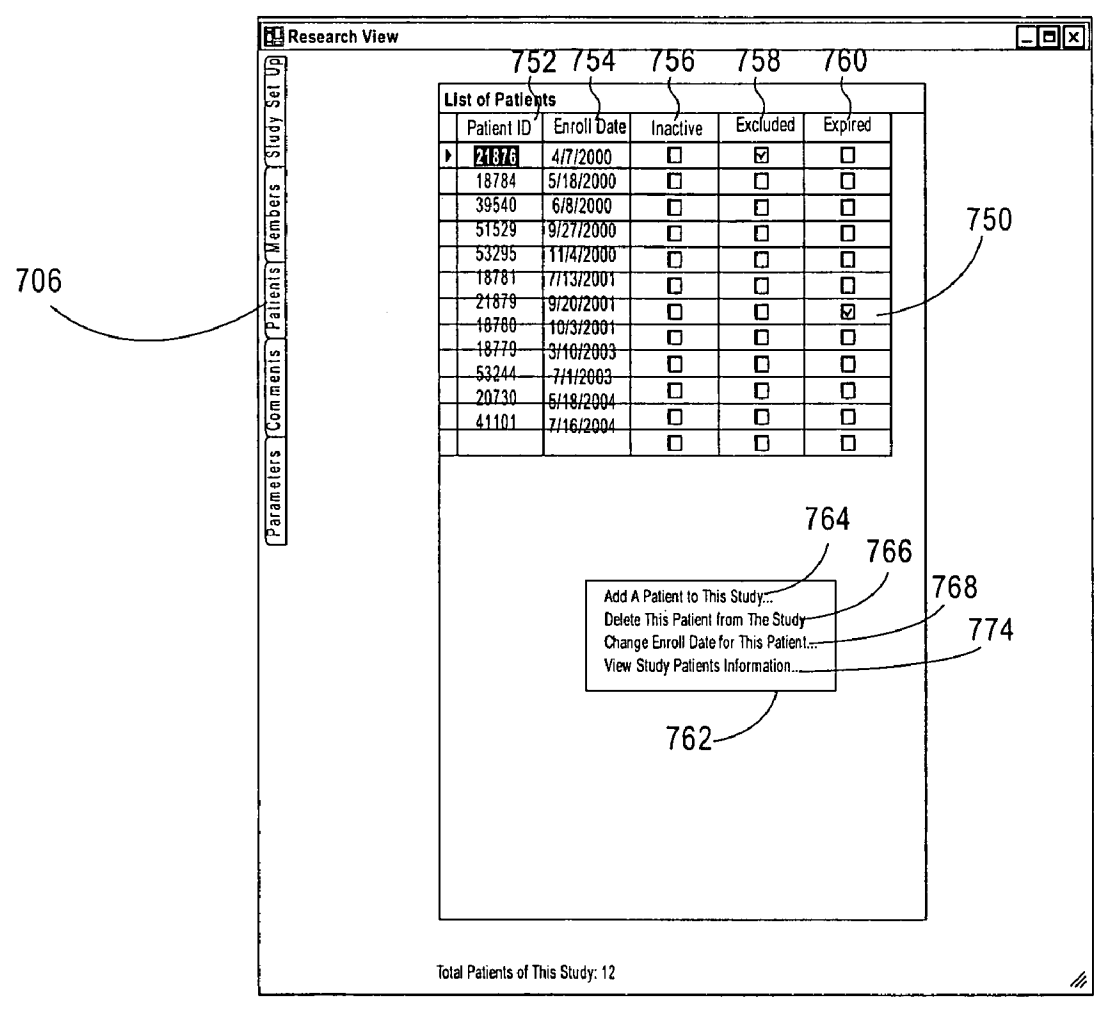

The patients tab 706 is illustrated in FIG. 50, wherein the patients tab 706 generally enables the user to add and remove patients from a study, and to update study patient information. The tab 706 presents a study patients table 750 with one or more rows of information, wherein each row includes information about a particular patient. Once a patient is added to a study, that patient is assigned a non-traceable patient identification number 752. The program only allows a system administrator to refer back to a study patient's identification information, such as name and medical record number, after enrollment in a research study. In addition to the identification number 752, each row of patient information includes an enrollment date 754, which is the date the patient was enrolled in the study; an inactive checkbox 756, which is checked if the patient is no longer active in the study; an excluded checkbox 758, which is checked if the patient has been excluded from the study after enrollment; and an expired checkbox 760, which is checked if the patient has expired after enrollment in the study.

A patients context menu 762 presents four menu items that are related to the study patients table 750, and generally enable the user to enroll patients in and remove patients from the study, change patients' enrollment date, and view patient identifiable information.

Figure 57:
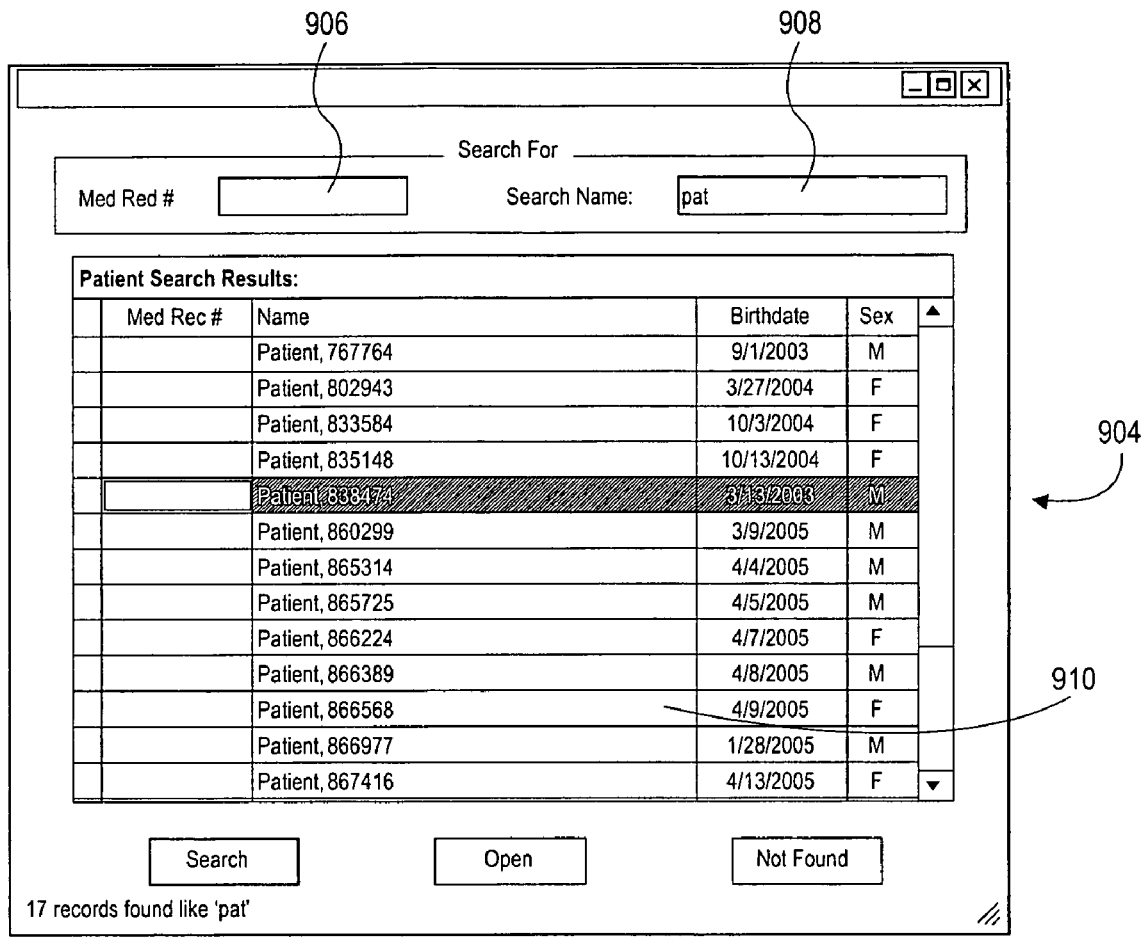
FIG. 57 is an exemplary patient search form invoked via the toolbar of FIG. 56.

An "Add A Patient To This Study" menu item 764 enables the user to enroll a patient in a research study. When the user selects this menu item 764, the program presents a patient search form as illustrated in FIG. 57. The patient search form receives one or more search parameters from the user and performs a search of the entire patient database according to the one or more parameters. The user selects' a patient from a list of patients, then selects an open button to enroll the selected patient to the study. When the user selects a patient, the program assigns the non-traceable identification number 752 to the patient. Once the patient is enrolled in the program, the user can change the patient's status by selecting one of the status checkboxes 756,758,760. The patient search form may also be launched from the menu toolbar 56, as explained below.

A "Delete This Patient From The Study" menu item 766 enables the user to remove a patient from the research study. The user must select a patient listed in the study patient table 750 before activating the context menu 766 and selecting this menu item 766. When the user requests that a specific patient be removed from the research study, the program presents a confirmation request (not shown) in a conventional manner. If the user confirms the removal action, the program removes the patient from the study and from the study patients table 750. If the user desires to maintain a record that a patient was previously an active study member, the user selects an appropriate status checkbox 756,758,760 as opposed to removing the patient from the study.

Figure 51:
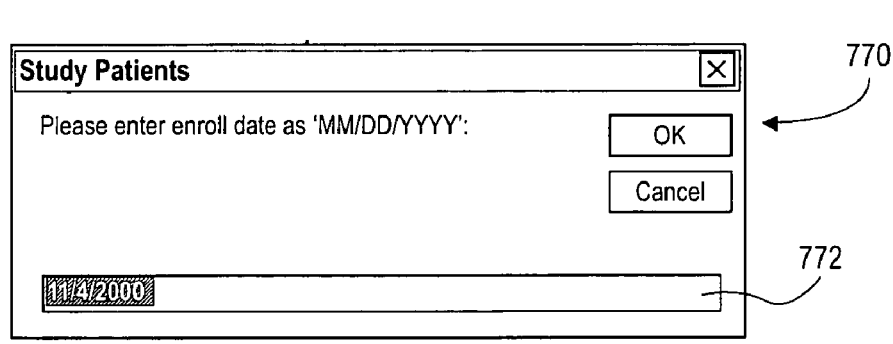
FIG. 51 is an exemplary data entry form for submitting patient enrollment date information associated with the patients tab of FIG. 50.

A "Change Enroll Date for This Patient" menu item 768 enables the user to change the date on which patients are enrolled in the study. When the user selects this menu item 768, the program presents a change enrollment date form 770 as illustrated in FIG. 51. The user changes the patient's enrollment date by entering a new date in a date field 772 and selecting the okay button. The enrollment date of the selected patient is then updated in the study patients table 750.

A "View Study Patient Information" menu item 774 enables the user to view identification information of study patient. As explained above, when a patient is enrolled in a study the program assigns the patient a non-traceable identification number 752 for privacy purposes. When the user selects the "View Study Patient Information" menu item 774 the program retrieves and presents the patient's actual identification information. This is the only way for the user to trace a patient identification number 752 to a particular patient. When the user selects this menu item 774, the program presents a study patient information form 776 as illustrated in FIG. 52. The form 776 associates the anonymous identification number 752 of each patient enrolled in the study with the patient's actual medical record number 778, name 780, and study enrollment date 782. The program allows only users with the role of system administrator to select this menu item 774 and view the form 776.

Figure 53:
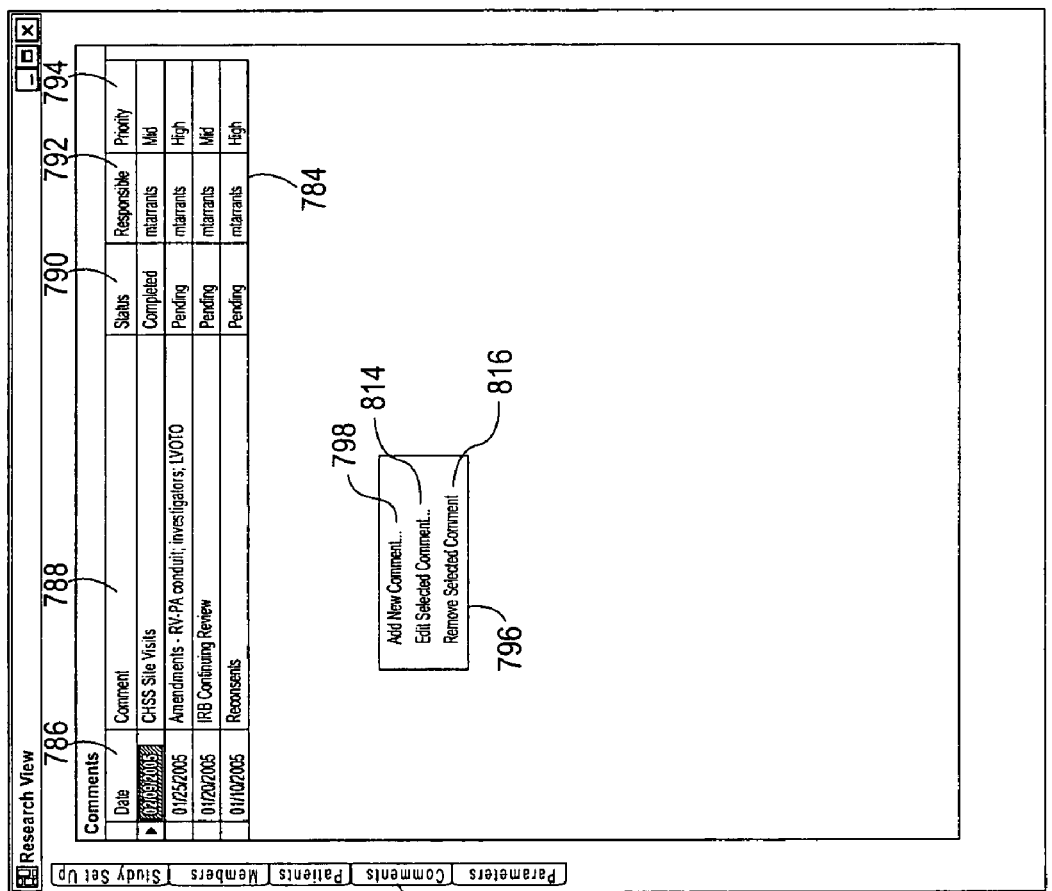
FIG. 53 is the interface of FIG. 47 illustrating a comments tab of the interface.

The comments tab 708 is illustrated in FIG. 53, wherein the tab 708 generally receives, logs, and tracks action items, issues, and responsibilities associated with a study. The tab 708 presents a comment table 784 with several rows of information, wherein each row relates to a particular comment and includes various columns of information. A date column 786 indicates the date on which the study comment was logged; a comment column 788 presents a description of the study comment or item; a status column 780 provides a status of the comment or item such as completed, pending or on hold; a responsible column 782 provides the name of the user designated as primarily responsible for the comment or item; and a priority column 784 lists the relative priority of the comment or item, such as low, mid, or high.

Figure 54:
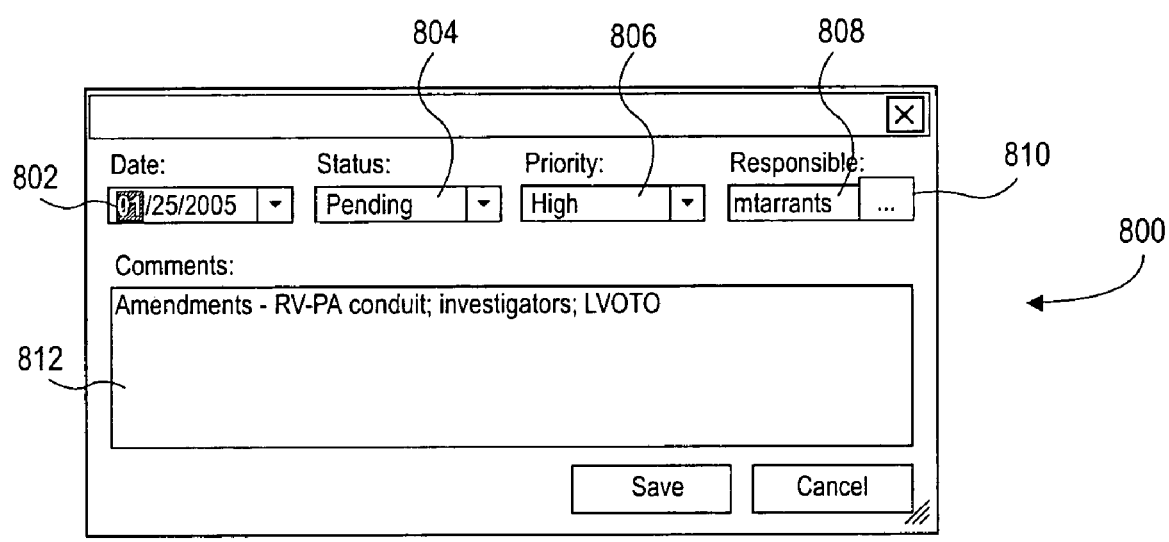
FIG. 54 is an exemplary form for submitting comment information associated with the comments tab of FIG. 53.

A study comments context menu 796 generally enables users to add new comments, edit existing comments, and remove comments. When the user selects an "Add New Comment" menu item 798 the program presents a new comment form 800 as illustrated in FIG. 54. The new comment form 800 presents several data fields for receiving detailed information about the comment from the user. A date drop-down menu 802 indicates a date on which the comment was logged or the issue was submitted by the user, wherein the user may type the date directly into the menu field or choose a date from a drop-down menu. The user chooses a status of the comment or issue by selecting a status option from a status drop-down menu 804, wherein the menu items (not shown) include completed, pending, and on-hold. The user indicates a priority of the comment or issue by selecting a priority option from a priority drop-down menu 806, wherein priority options include low, mid, and high.

A responsible drop-down menu 808 of the new comment form 800 enables the user to indicate a user who is primarily responsible for the comment or issue. The user may do so in either of two ways: first, the user may type the name of a user directly into the field; second, the user may select the button 810 labeled " . . . " to invoke the form 748 illustrated in FIG. 49 and choose a user via the form 748. In the comments field 812 the user types any comment, issue, status description, etcetera. This entry is displayed as the comment 788 in the study comments table 784. The user closes the form and stores the form data by selecting the save button, or closes the form without saving any of the information by selecting the cancel button.

When the user selects the "Edit Selected Comment" menu item 814 the program presents the new comment form 800 illustrated in FIG. 54 and described above. Before selecting this menu item 814, however, the user must select a row of information in the study comments table 784. The program presents the form 800 populated with comment information from the selected row. The user may then update any of the fields of the form 800 and store the saved information by selecting the save button.

A "Remove Selected Comment" menu item 816 enables the user to delete an entire row of information from the study comments table 784. To delete a row of information from the table 784, the user selects the row, activates the context menu 784, and selects this menu item 816. When the user requests that a specific row of information be removed from the table 784, the program presents a confirmation request (not shown) in a conventional manner. If the user confirms the removal action, the program removes the row of information from the table 816.

Figure 55:
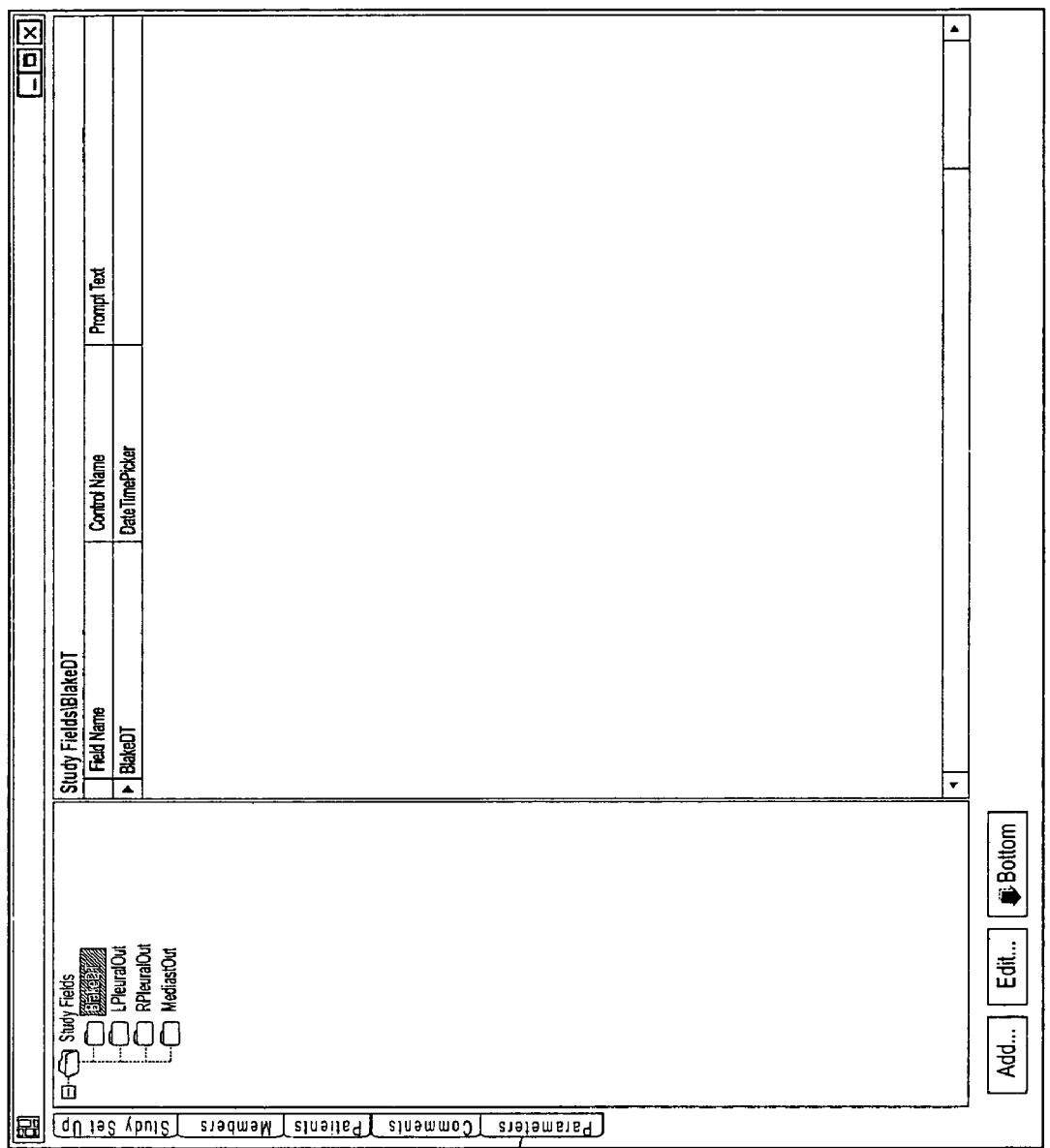
FIG. 55 is the interface of FIG. 47 illustrating a parameters tab of the interface.

The parameters tab 710 is illustrated in FIG. 55 and enables the user to configure research study specific information for entry into the program's database. Research studies often require special information to be recorded that is not part of the research dataset described above. An example of such information is specific family medical history information or other data that is required for the research study but that is not part of the patient's normal medical information. The parameters tab 710 enables users to build a custom form for a study and define the data fields, controls, and questions that will appear on the form. This custom form can then be accessed via the studies tab 310 of the patient view interface 310.

The Menu Toolbar

Figure 56:
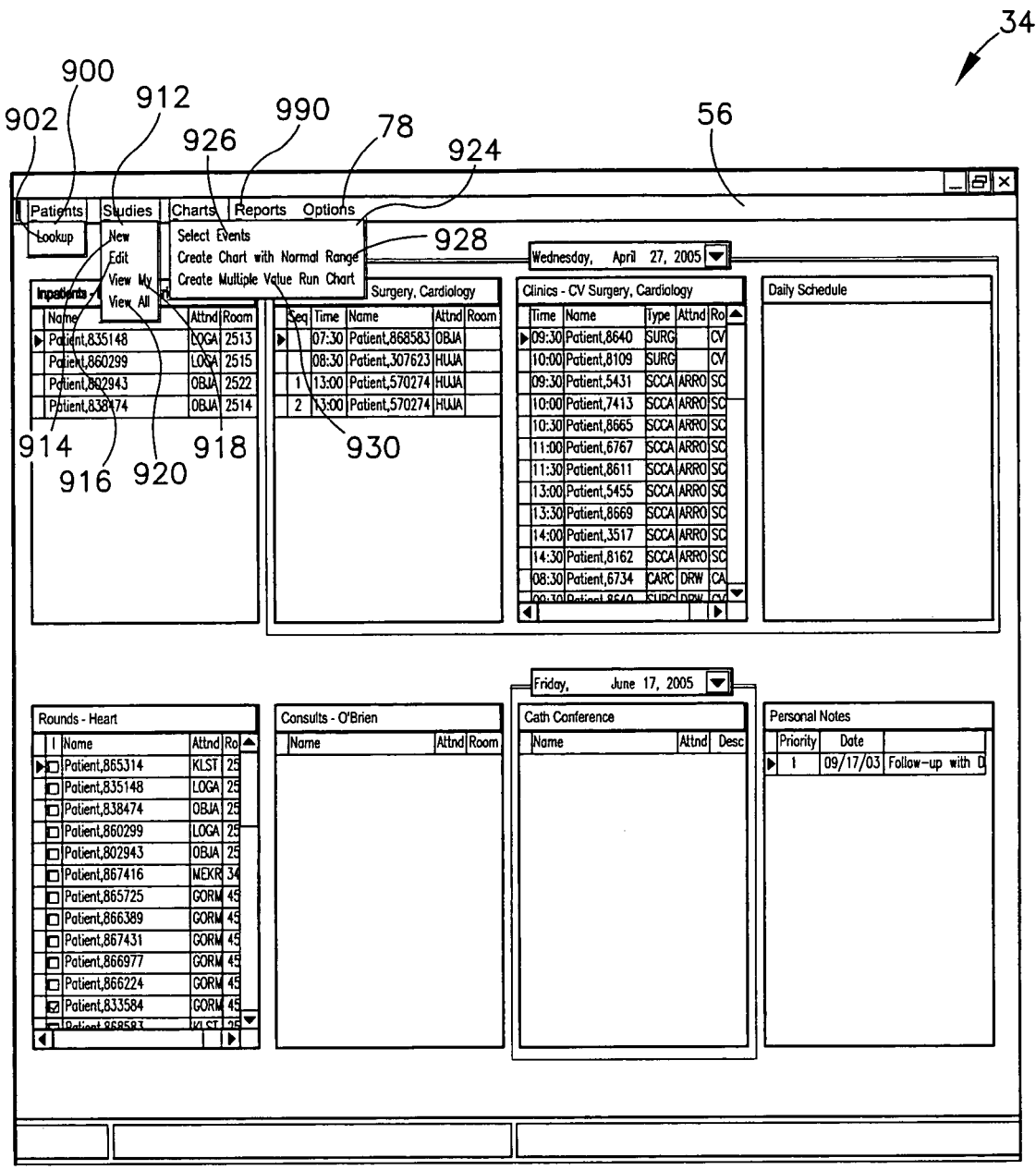
FIG. 56 is the interface of FIG. 3 illustrating various menus of a interface toolbar.

The menu toolbar 56 is presented as part of one or more of the views described above and generally presents the same set of menus in each view. The menu toolbar is presented as part of the department view interface 34, the patient view interface 300, and the visit view interface 400. Particular reference will be made to the menu toolbar 56 as illustrated in FIG. 56 as part of the department view interface 34, with the understanding that when presented as part of other interfaces, the toolbar performs substantially the same function.

The patient menu 900 of the menu toolbar 56 includes a patient lookup 902 menu item. When the user selects the patient lookup menu item 902 the program presents a patient search form 904 as illustrated in FIG. 57. The patient search form 904 enables the user to search for a patient or group of patients according to one or more search parameters, select a patient, and open the patient view for the selected patient. The illustrated form 904 includes two search parameters fields: medical record number 906 and patient name 908. The user may submit a portion of a name, such as the first one, two, or three letters of the last name, and program will retrieve all patients who last names begin with the submitted letter or letters. If the user submits both a medical record number and a search name, the program will only search for the patient medical record number.

The form 904 presents search results in the form of a search result table 910 comprising one or more rows of patient information. Each row pertains to a single patient, and the rows are divided into columns for the patient's medical record number, name, birth date, and sex. A search button initiates a search of the program database according to one or both of the search parameters 906,908; an open button opens the patient view of a patient selected from the patient search results table 910; and a not found button opens an HIS search form (not shown), which allows the user to search the HIS 20b for information about the patient. If the patient is found in the HIS 20b, the user then has the option to view visits, verify that the patient is the one being sought, and extract patient information from the HIS 20b to the local database 20e.

The studies menu 912 of the menu toolbar 56 is associated with the research view, described above. The studies menu presents four menu items, including new study 914, edit study 916, view my studies 918, and view all studies 920.

The add new study menu item 914 can be selected only by a user with the role of system administrator. When the user selects this menu item, the program presents a blank new research form 700, illustrated in FIG. 47. The process of setting up a new research study using the form 700 is described in detail above.

Figure 58:
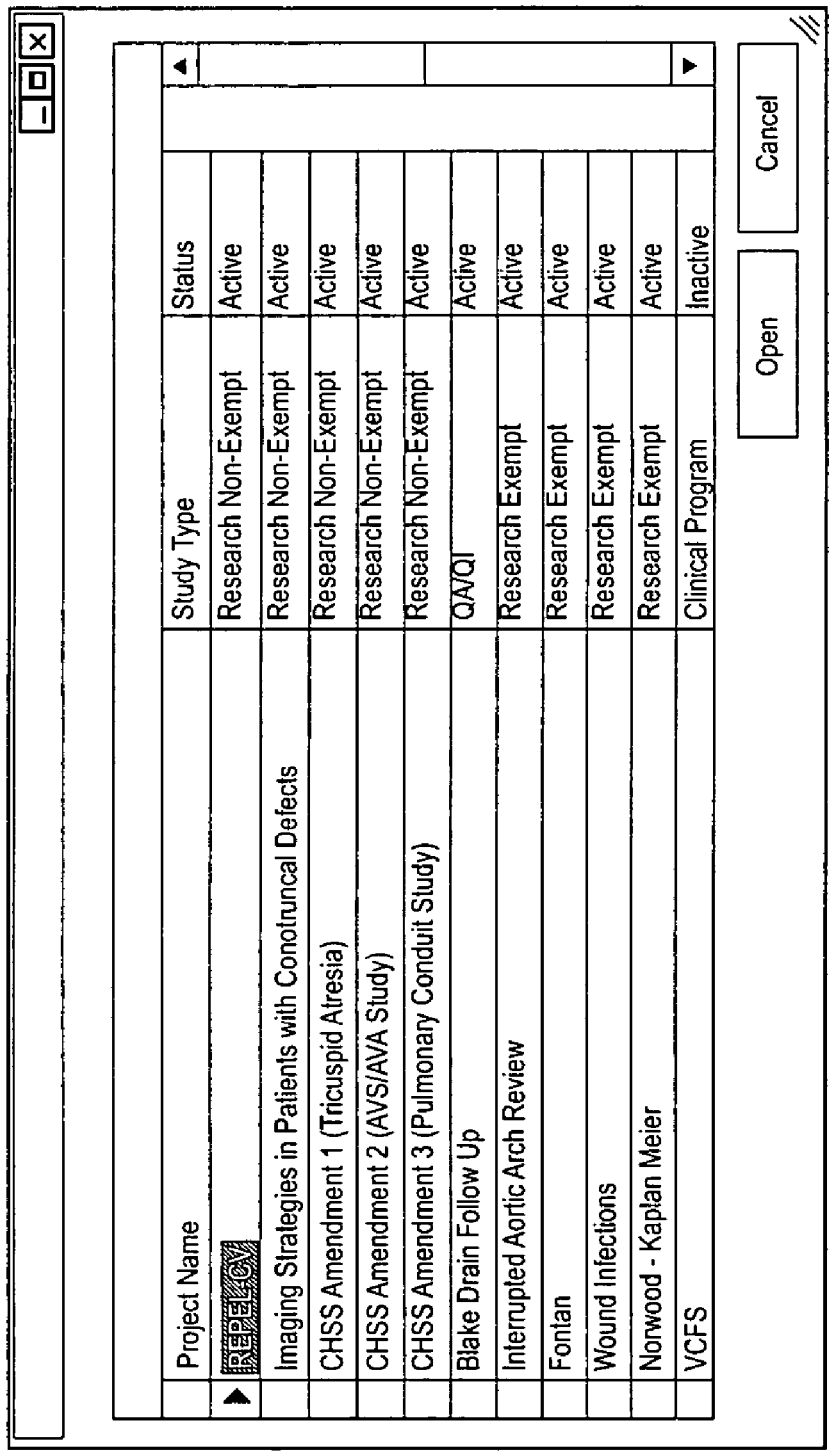
FIG. 58 is an exemplary patient studies form invoked via the toolbar of FIG. 56, wherein the form presents a list of patient studies.

The edit study menu item 916 also can only be selected by a user with the role of system administrator. When the user selects this menu item 916, the program presents a study list form 922 as illustrated in FIG. 58. The user selects a study from the list of studies presented in the form 922, and selects an open button to display the research study form 700. The user can then edit study information via the research study form 700.

The view my studies menu item 918 can be selected by any user, and causes the program to present the study list form 922 illustrated in FIG. 58. However, when the user invokes the study list form 922 via the view my studies menu item 918, the form 922 only includes studies of which the user is a member. The user can then select a particular study and select the open button to invoke the research study form 700 to view information relating to the study. The study information will be read-only, such that the user will not be able to modify information contained therein.

The view all studies menu item 920 can be selected by any user and causes the program to present the study list form 922 illustrated in FIG. 58, wherein the form 922 presents a list of all research studies, irrespective of the user's membership in any study. When the study list form 922 is invoked via the view all studies menu item 920, the user cannot retrieve any further information about a particular study, but is limited only to viewing the list of studies presented in the form 922.

The charts menu 924 of the menu toolbar 56 enables the user to create charts of various pieces of information that are used by physicians and other care givers to correlate and evaluate leading indicators, events, interventions, and results. This is accomplished by charting events and interventions on the same graphs as indicators and results are charted. The charts menu 924 includes menu items select events to chart 926, create chart with normal range 928, and create multiple value run chart 930.

Figure 59:
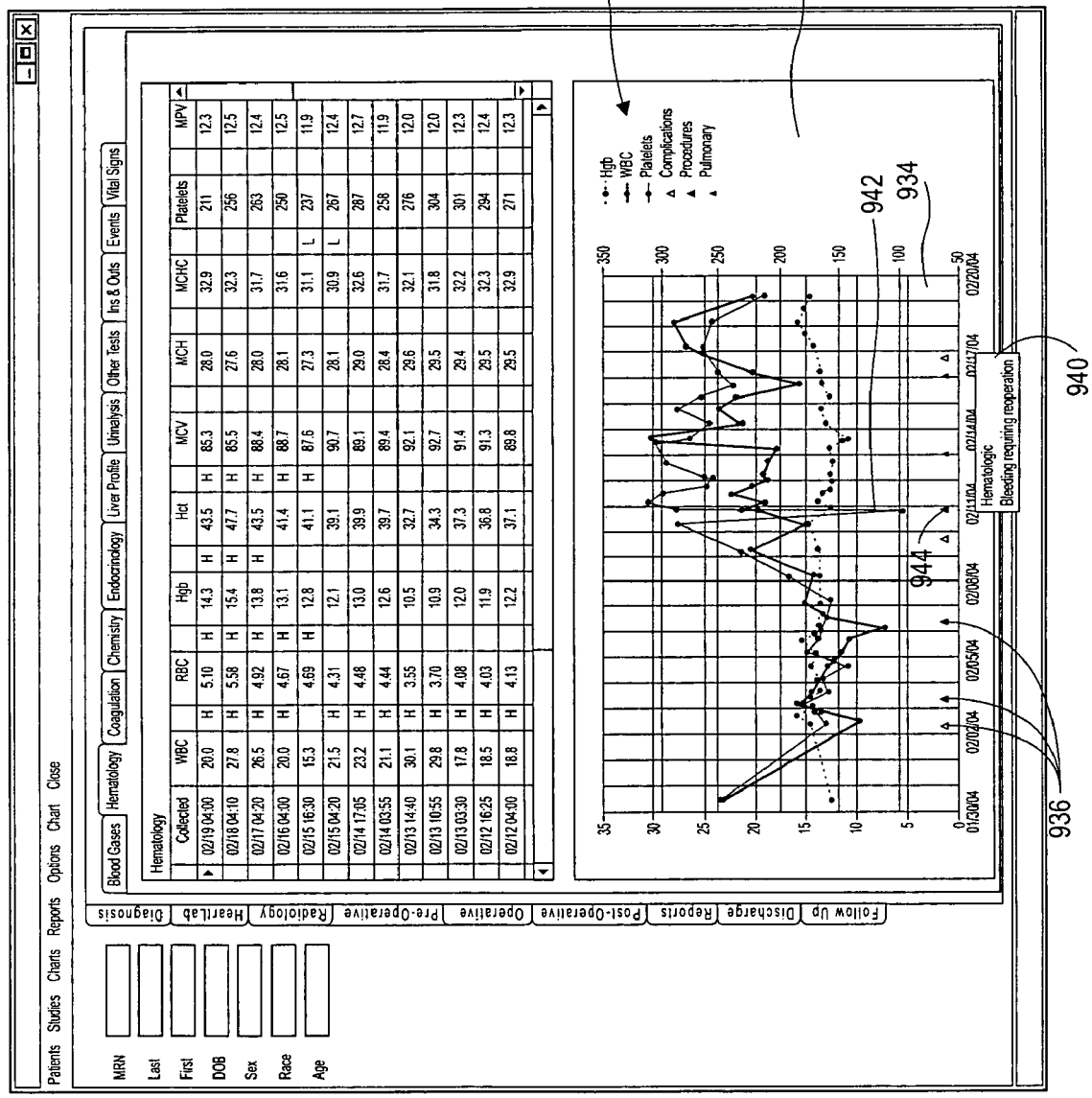
FIG. 59 is the hematology element of FIG. 24 illustrating a laboratory results chart that simultaneously presents event indicators and laboratory result graphs.

The select events to chart menu item 926 enables the user to select one or more events from a plurality of events to chart on a graph concurrently with one or more indicators or results. FIG. 59 provides an exemplary chart 932 with complications, procedures and pulmonary events charted on the same graph 934 as hematology lab results. Various milestone points 936 are plotted along the bottom of the graph 934, wherein the milestone points 936 are preferably presented in different colors. A legend 938 within the chart 932 defines these points to be complications, procedures, and pulmonary events according to color. Each milestone point 936 represents an exact time that a corresponding event occurred relative to the hematology lab results. Thus, a user can quickly and easily correlate a particular hematology lab result—or a group of results—to a particular complication, procedure, or both.

The chart 932 also enables the user to quickly review the details of each complication, procedure and pulmonary event represented by the milestone points 936. The user does this by placing an on-screen pointer or cursor over a particular milestone 936, wherein the program displays a description 940 of the event. In the illustrated example, the user can quickly and easily infer that there is a relationship between a sudden drop in platelets 942 and the hematological event 944 of bleeding requiring operation.

Figure 60:
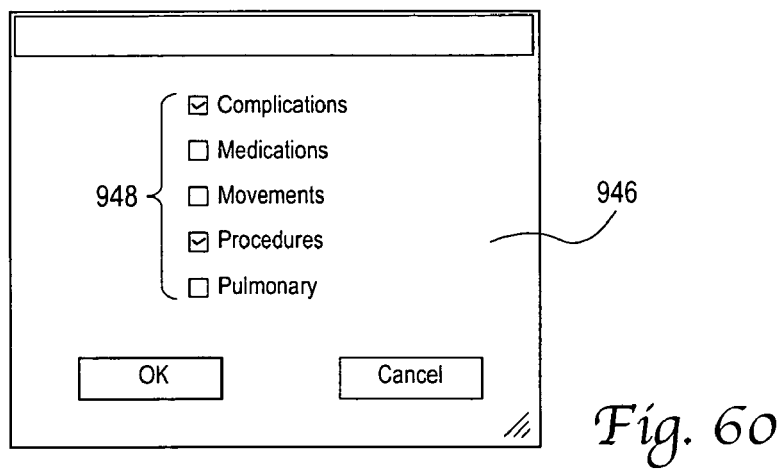
FIG. 60 is an exemplary form for submitting event information associated with the chart of FIG. 59.

When the user selects the select events to chart menu item 926 the program presents a select events to chart form 946, illustrated in FIG. 60. The events that will be charted correspond to the selected categories for a patient as described above in relation to the events nested tab 510 of the post operative tab 412 of the visit view interface 400, as illustrated in FIG. 39. The user selects one or more of the event categories from the form 946 to include in the chart 932 and selects an okay button to apply the selection or selections. Events from the selected event categories 948 are then charted in all graphs that the program presents. The user may discontinue this function by selecting the select events to chart menu item 926 and deselecting any event categories 948 that were previously selected.

Figure 61:
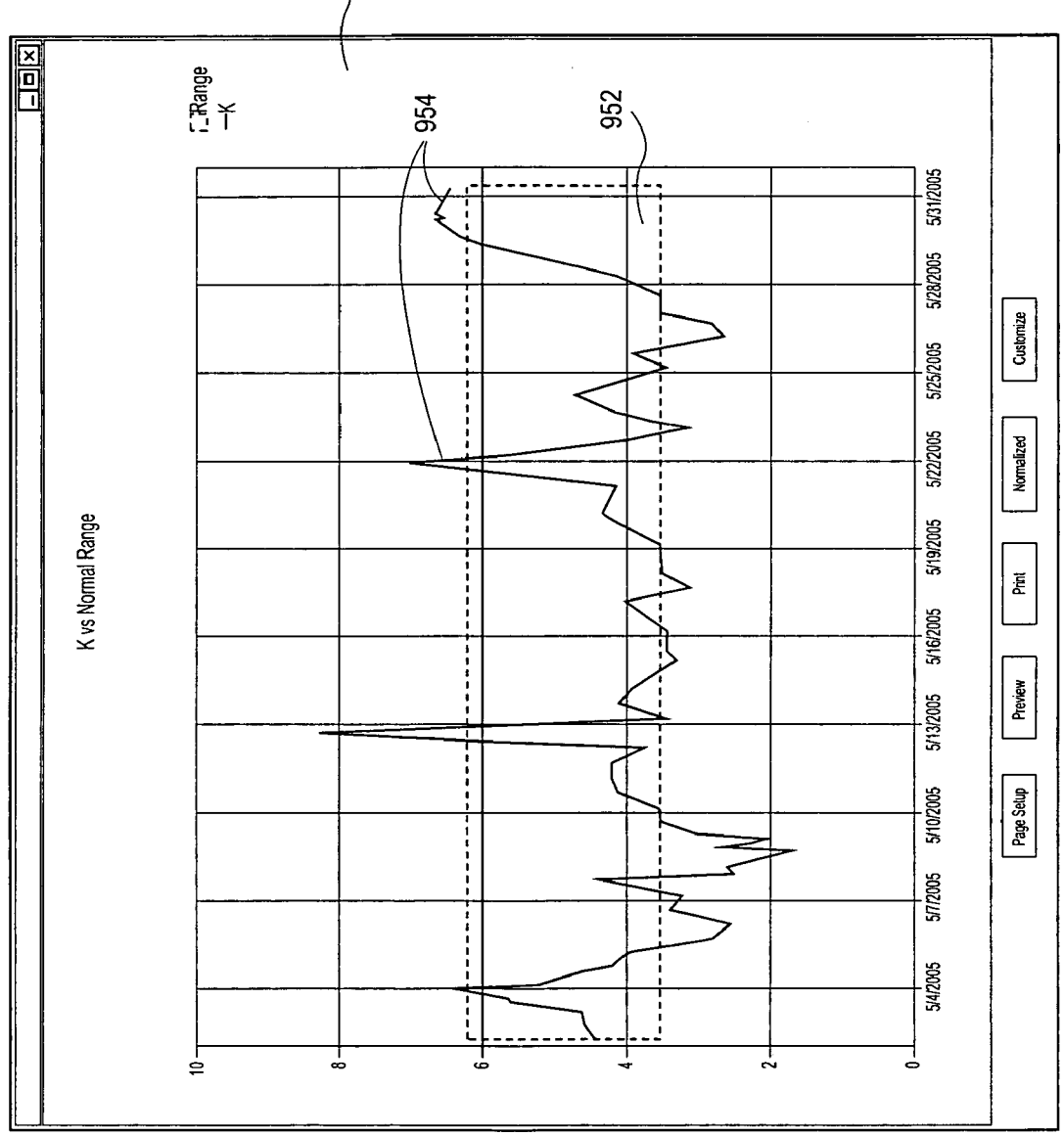
FIG. 61 is an exemplary chart with a normal range indicator.

The create chart with normal range menu item 928 enables the user to compare a patient's laboratory test results to normal test values. Many laboratory results are communicated from the laboratory with values that the laboratory considers to be normal ranges for a particular patient's age, weight, and other factors—collectively referred to herein as the patient profile. The program is operable to graph each numeric laboratory result type that is returned with the normal range when the user selects the create chart with normal range menu item 928. An exemplary chart 950 with a normal range indicator 952 is illustrated in FIG. 61. The chart 950 depicts the patient's blood chemistry potassium level (K) against the normal range as determined by the lab for patients with similar characteristics. The normal range indicator 952 is a shaded region that enables the user to quickly and easily compare the patient's actual measured potassium level 954 with the normal range over a period of time, such that a physician can quickly determine when and by how much the patient's potassium level was abnormally high and abnormally low. Events and interventions, as described above, can also be plotted in a normal range chart.

Figure 62:
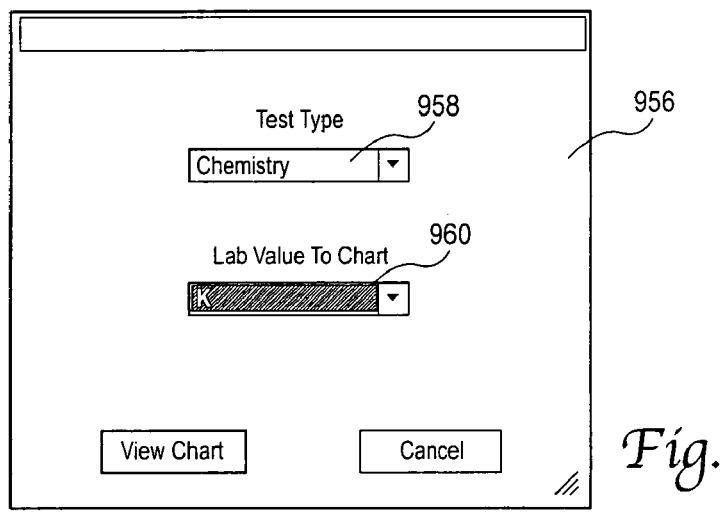
FIG. 62 is an exemplary form for submitting test type and lab value information associated with the chart of FIG. 61.

When the user selects the create chart with normal range menu item 928, the program presents a range chart selection form 956 as illustrated in FIG. 62. The user selects a type of test from a test type drop-down menu 958, which limits the options in a lab value to chart drop-down menu 960 to only those associated with the selected test type. The user then selects the lab value to be charted from the lab value to chart drop-down menu 960. The program then generates a chart, such as chart 950, with the selected test result in normal range.

A table of numeric lab tests is presented in FIG. 63, wherein each lab test is associated with a test type 962, a first indicator 964 indicating whether a range chart may be generated for the test, and a second indicator 966 indicating whether a multiple value run chart may be generated for the test.

Figure 64:
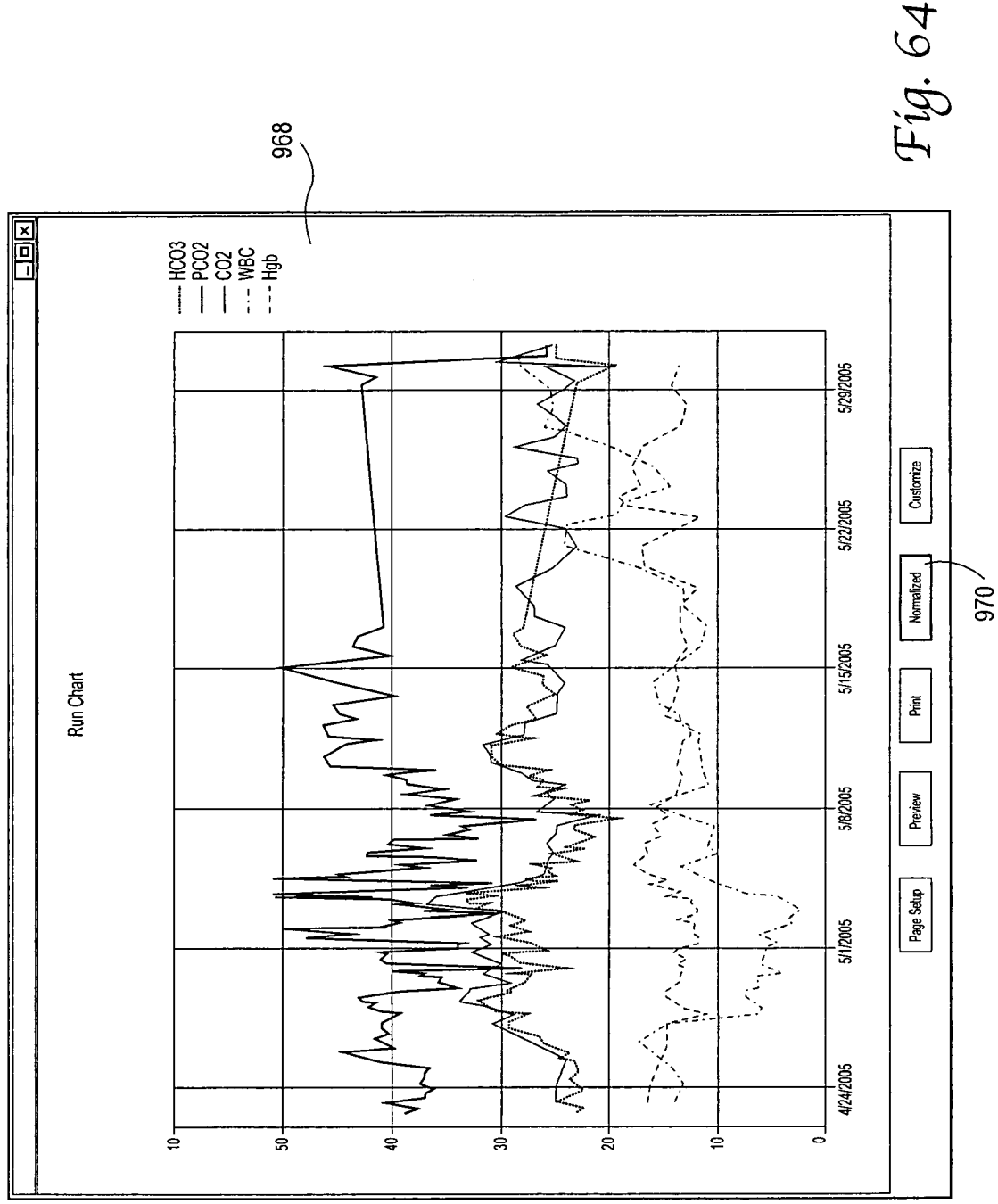
FIG. 64 is an exemplary run chart illustrating various laboratory test results plotted before normalization.

A multiple value run chart plots lab results of different types on a single graph. An exemplary multiple value run chart 968 is illustrated in FIG. 64, which simultaneously plots two blood gas lab results—HCO3 and PCO2, one chemistry lab result—CO2, and two hematology test results—WBC and Hgb. The program can include any numeric lab result in a multiple value run chart, and can simultaneously plot up to five lab results of different lab types.

Figure 65:
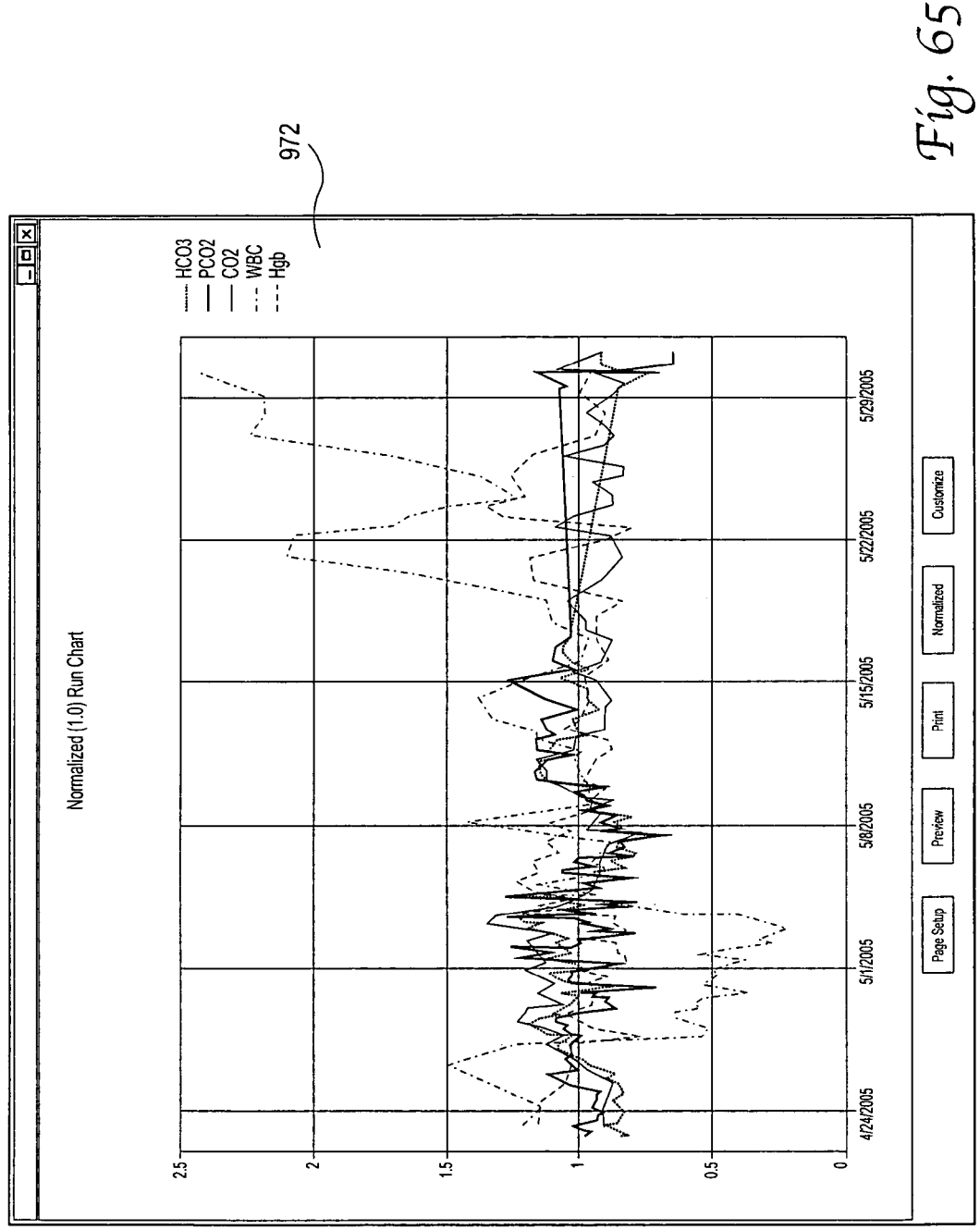
FIG. 65 is the run chart of FIG. 64 illustrating the laboratory test results plotted after normalization.

A normalize button 970 below the chart 968 enables the user to normalize the plotted values to more easily depict relationships between lab results. When the user selects the normalize button 970 the program eliminates disparities between lab test values by recalculating each as a relative change around a value of one. This result is illustrated in FIG. 65. The normalized chart 972 is especially helpful for simultaneously plotting lab values that are quite different, such as ph results, where a normal result may be 7.4, but a platelet result is typically around 300. Events and interventions, explained above, can also be displayed simultaneously in a normalized chart.

Figure 66:
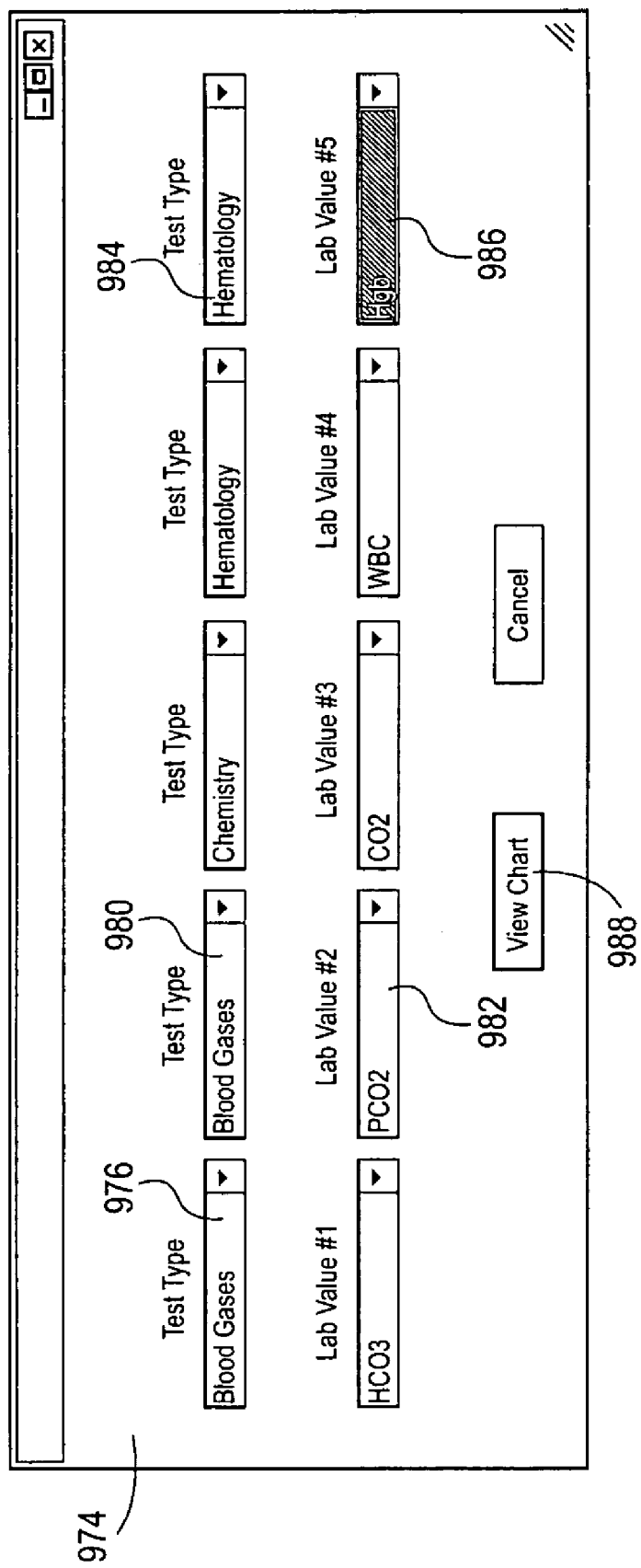
FIG. 66 is an exemplary form for submitting test type and lab value information associated with the chart of FIG. 65.

When the user selects a create multiple value run chart menu item 930, the program presents a run chart selection form 974 illustrated in FIG. 66. To chart up to five lab results on a single graph, the user selects a first test type from a first test type drop down menu 976 and a corresponding lab result from a first lab value drop-down menu 978; a second type from a second test type drop down menu 980 and a corresponding lab result from a second lab value drop-down menu 982; and so forth up to a fifth type from a fifth test type drop down menu 984 and a corresponding lab result from a fifth lab value drop-down menu 986. Once the user has selected two or more test types and lab values, he or she selects a view chart button 988 to cause the program to present the chart including the selected test results.

Figure 9:
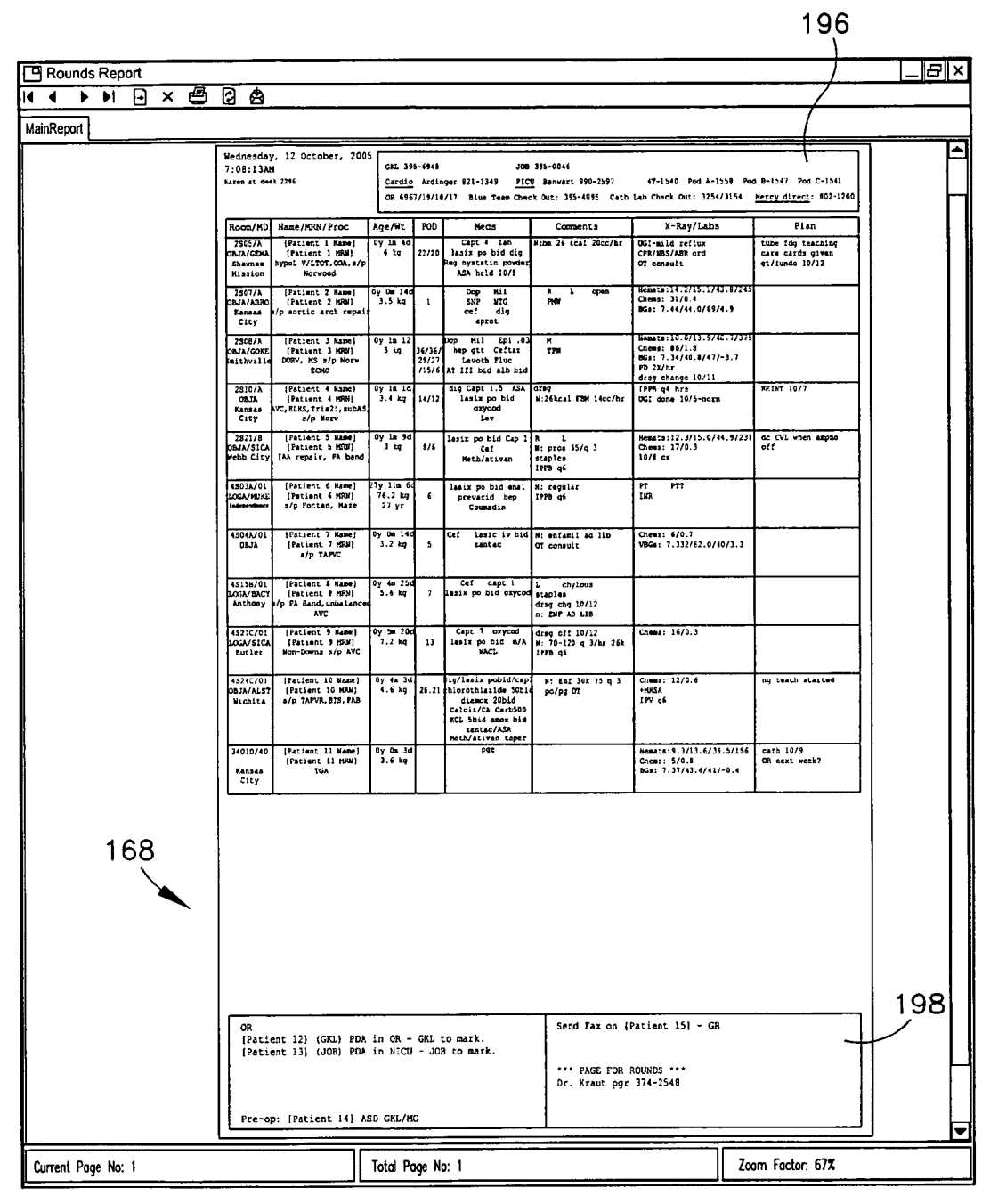

The reports menu 990 presents one or more reports menu items (not shown) that, when selected, generated reports relating to the other aspects of the program such as, for example, the rounds report 168 illustrated in FIG. 9.

Figure 67:
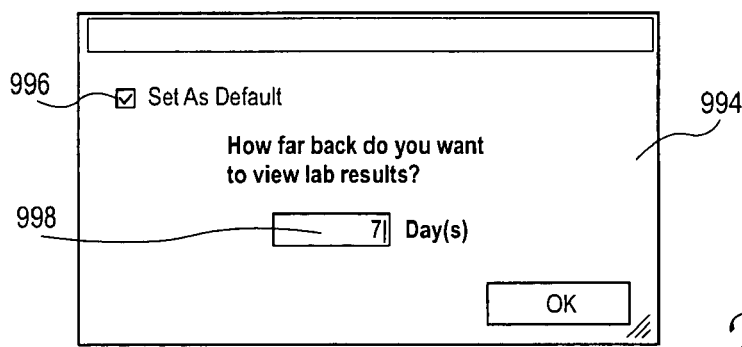
FIG. 67 is an exemplary form for submitting time period information associated with data retrieval functions of the program.

The options menu item 78 enables the user to choose one or more options associated with program, such as the lab lookback period. When the user chooses a lab lookback period menu item 992 of the options menu 78, the program generates a lab lookback form 994 as illustrated in FIG. 67. The form 994 allows the user to determine the number of days back labs are viewed when any view current clinical data items are selected: A default lookback period is seven days, but the user can change the lookback period to any integer value. If the user selects a set as default checkbox 996, the value currently listed in the lookback data field 998 becomes the default lookback period. If the set as default checkbox 996 is not selected, the lookback value 998 is only used for the current session.

Having thus described the preferred embodiment of the invention, what is claimed as new and desired to be protected by Letters Patent includes the following:

1. A computer-readable medium encoded with a computer program for organizing and presenting information relating to medical research studies, the computer program including:
    a study setup code segment for presenting a user interface that receives new study information from a user and sets up the new study in a computer system, wherein the new study information includes study type, study status, enrollment status, IIRB information, a project description, project goals, inclusion criteria, and exclusion criteria;
    a members code segment for adding members to a study, removing members from the study, and indicating a role for each member, wherein member roles are chosen from the group consisting of primary investigator, study coordinator, sub-investigator, and inactive;
    a patients code segment for adding new patients to a study, presenting study patient information for review, removing patients from the study, and indicating a status of each patient, wherein each patient's status is chosen from the group consisting of inactive, excluded, and expired, and wherein each patient is assigned an nontraceable patient identification number and identified by the identification number in study;
    a study comments code segment for receiving comments from members of the study, storing the comments, editing the comments, and presenting the comments for review, wherein each comment is assigned a receiving date, a status, a responsible member, and a priority;
    a study parameters code segment for configuring data to be stored in a database associated with the research study;
    a view user studies code segment for determining a current program user presenting for review a list of all studies that the user is a member of, and presenting detailed information relating to a study selected by the user from the list of studies; and a view all studies code segment for presenting for review a list of all studies maintained by the program and preventing the user from viewing detailed information relating to a study.

2. The computer-readable medium as set forth in claim 1, wherein the computer program further comprises an events code segment for receiving event information from the user, wherein the event information includes a date of the event.

3. The computer-readable medium as set forth in claim 2, wherein the computer program further comprises a laboratory communications code segment for maintaining a communications link with a laboratory information system and for electronically receiving a laboratory test result from a laboratory information system, wherein the test result includes a date of the test and a value of the result.

4. The computer-readable medium as set forth in claim 2, wherein the computer program further comprises a chart code segment for creating a laboratory test results chart, wherein the chart includes a visual indication of the value of the test result and a visual indication of the date of the event relative to the date of the test.

* * * * *